US011524082B2

(12) United States Patent
Low et al.

(10) Patent No.: US 11,524,082 B2
(45) Date of Patent: Dec. 13, 2022

(54) FBSA-BASED THERAPEUTIC AND RADIOIMAGING CONJUGATES TARGETING CARBONIC ANHYDRASE POSITIVE CANCERS

(71) Applicant: PURDUE RESEARCH FOUNDATION, West Lafayette, IN (US)

(72) Inventors: Philip S. Low, West Lafayette, IN (US); Isaac J. Marks, West Lafayette, IN (US); Spencer Gardeen, Bloomington, MN (US); Sumith A. Kularatne, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 138 days.

(21) Appl. No.: 16/640,539

(22) PCT Filed: Aug. 21, 2018

(86) PCT No.: PCT/US2018/047297
§ 371 (c)(1),
(2) Date: Feb. 20, 2020

(87) PCT Pub. No.: WO2019/040474
PCT Pub. Date: Feb. 28, 2019

(65) Prior Publication Data
US 2020/0353108 A1    Nov. 12, 2020

Related U.S. Application Data

(60) Provisional application No. 62/548,670, filed on Aug. 22, 2017.

(51) Int. Cl.
*A61K 51/04* (2006.01)
*A61B 90/00* (2016.01)
*A61K 47/54* (2017.01)
*A61P 35/00* (2006.01)
*A61B 5/00* (2006.01)
*A61K 31/395* (2006.01)
*A61K 31/454* (2006.01)
*A61K 31/537* (2006.01)
*A61K 49/00* (2006.01)

(52) U.S. Cl.
CPC ........ *A61K 51/0497* (2013.01); *A61B 5/0071* (2013.01); *A61B 90/39* (2016.02); *A61K 31/395* (2013.01); *A61K 31/454* (2013.01); *A61K 31/537* (2013.01); *A61K 47/54* (2017.08); *A61K 47/542* (2017.08); *A61K 47/545* (2017.08); *A61K 49/0043* (2013.01); *A61K 49/0052* (2013.01); *A61P 35/00* (2018.01); *A61B 2090/3904* (2016.02); *A61B 2090/3933* (2016.02); *A61B 2090/3941* (2016.02)

(58) Field of Classification Search
CPC .............. A61K 51/0497; A61K 31/395; A61K 31/454; A61K 31/537; A61K 47/54; A61K 47/542; A61K 47/545; A61K 49/0043; A61K 49/0052; A61K 51/04; A61K 51/0402; A61B 5/0071; A61B 90/39; A61B 2090/3904; A61B 2090/3933; A61B 2090/3941; A61P 35/00; C07D 255/02; C07D 311/80; C07D 405/10
See application file for complete search history.

(56) References Cited

U.S. PATENT DOCUMENTS 9,725,467 B2    8/2017    Matulis et al.

FOREIGN PATENT DOCUMENTS

| CA | 2938574 | 8/2015 |
|---|---|---|
| WO | 2014062044 A1 | 4/2014 |
| WO | 2017058370 A1 | 4/2017 |
| WO | 2017161197 A1 | 9/2017 |
| WO | 2018160622 A1 | 9/2018 |

OTHER PUBLICATIONS

Kazokaite, J. et al., "Fluorinated benzenesulfonamide anticancer inhibitors of carbonic anhydrase IX exhibit lower toxic effects on zebrafish embryonic development than ethoxzolamide," Drug and Chemical Toxicology., 2016, 40(3) pp. 309-19.
Juozapaitiene, V. et al., "Purification, enzymatic activity and inhibitor discovery for recombinant human carbonic anhydrase XIV," Journal of Biotechnology, Elsevier, Amsterdam NL, 2016, vol. 240, pp. 31-42.
Zubriene, A. et al., "Intrinsic Thermodynamics and Structures of 2,4- and 3,4- Substituted Fluorinated Benzenesulfonamides Binding to Carbonic Anhydrases," CHEMMEDCHEM, 2016, 12(2) pp. 161-176.
Smirnoviene, J. et al., "Picomolar inhibitors of carbonic anhydrase: Importance of inhibition and binding assays," Analytical Biochemistry, 2017, vol. 522, pp. 61-72.
Janoniene, A. et al., "A Versatile Carbonic Anhydrase IX Targeting Ligand-Functionalized Porous Silicon Nanoplatform for Dual Hypoxia Cancer Therapy and Imaging," ACS Appl. Mater. Interfaces, 2017, vol. 9, pp. 13976-87.

(Continued)

*Primary Examiner* — Robert S Cabral
(74) *Attorney, Agent, or Firm* — Barnes & Thornburg LLP

(57) ABSTRACT

The present disclosure relates to compositions and methods of carbonic anhydrase IX inhibitors. The present disclosure also relates to targeting conjugates of carbonic anhydrase IX inhibitors. The present disclosure also relates to the use of targeting conjugates of carbonic anhydrase IX inhibitors in methods of treating disease and for imaging of disease.

19 Claims, 15 Drawing Sheets

(56) References Cited

OTHER PUBLICATIONS

Zhang, H. et al., "Microfluidic Encapsulation of Prickly Zinc-Doped Copper Oxide Nanoparticles with VD1142 Modifier Spermine Acetalated Dextran for Efficient Cancer Therapy," Advanced Healthcare Materials, 2017, 6(11) 13 pages.
Dudutiene, V. et al., "Discovery and Characterization of Novel Selective Inhibitors of Carbonic Anhydrase IX," Journal of Medicinal Chemistry, 2014, vol. 57, pp. 9435-9446.
Supplementary European Search Report prepared for EP 18849342, dated Mar. 12, 2021.
Dudutiene, V. et al., "Functionalization of Fluorinated Benzenesulfonamides and Their Inhibitory Properties toward Carbonic Anhydrases," CHEMMEDCHEM, 2015, 10(4) pp. 662-687.
PCT Search Report and Written Opinion prepared for PCT/US2018/047297, dated Dec. 4, 2018.
Talibov, Vladimir O., et al., "Kinetically Selective Inhibitors of Human Carbonic Anhydrase Isozymes I, II, VII, IX, XII, and XIII," Jan. 25, 2016, Journal of Medicinal Chemistry, vol. 59, No. 5, pp. 2083-2093.

FBSA-BASED THERAPEUTIC AND RADIOIMAGING CONJUGATES TARGETING CARBONIC ANHYDRASE POSITIVE CANCERS

CROSS REFERENCE TO RELATED APPLICATIONS

This application is a national stage entry under 35 USC § 371 of PCT International Application Number PCT/US2018/047297, filed Aug. 21, 2018, which claims priority under 35 U.S.C. § 119(e) to U.S. Provisional Application No. 62/548,670 filed Aug. 22, 2017, the disclosures of which are incorporated herein by reference in their entirety.

FIELD

The present disclosure relates to compositions and methods of carbonic anhydrase IX inhibitors. The present disclosure also relates to targeting conjugates of carbonic anhydrase IX inhibitors. The present disclosure also relates to the use of targeting conjugates of carbonic anhydrase IX inhibitors in methods of treating disease and for imaging of disease.

BACKGROUND

The microenvironment can greatly affect the phenotype of cancer cells within a tumor. One such microenvironmental effect is hypoxia due to poorly formed vasculature present within tumors (See for example Noman M Z, Hasmim M, Messai Y, Terry S, Kieda C, Janji B, Chouaib S. Hypoxia: a key player in anti-tumor immune response. A review in the Theme: Cellular Responses to Hypoxia. *Am J Physiol Cell Physiol.* 2015, 309(1):C569-0579). Studies have shown that 1% to 1.5% of all genes are regulated by hypoxia (Harris A L. Hypoxia—a key regulatory factor in tumour growth. *Nat Rev Cancer.* 2002. 2(1):38-47). Not surprisingly then, hypoxic cancer cells can exhibit markedly different patterns of gene expression. These changes can lead to differences in sensitivity towards chemotherapeutics when in a hypoxic microenvironment which in turn can lead to increased aggressiveness and recurrence of the cancer (Yamada S, Utsunomiya T, Morine Y, Imura S, Ikemoto T, Arakawa Y, Kanamoto M, Iwahashi S, Saito Y, Takasu C, Ishikawa D, Shimada M. Expressions of hypoxia-inducible factor-1 and epithelial cell adhesion molecule are linked with aggressive local recurrence of hepatocellular).

Due to the effects of hypoxia, efforts have been made to identify cancer specific hypoxia markers to exploit for selective imaging. One such marker, carbonic anhydrase IX (also referred to herein as CA IX) is expressed via the activation of hypoxia-inducible factor-1 (HIF-1). CA IX is a member of a group of metalloproteins, usually containing Zinc that catalyze the reversible hydration of carbon dioxide $((CO_2+H_2O \leftrightarrow HCO_3^- +H^+)$. CAIX is among the most active CAs for the $CO_2$ hydration reaction, and contains four domains on the basis of sequence similarity: an N-terminal proteoglycan-like (PG) domain, a CA catalytic domain, a transmembrane segment (TM), and an intracytoplasmic (IC) portion. CA IX is expressed in many cancers including lung, colorectal, gastric, pancreatic, breast, cervical, bladder, ovarian, brain, head & neck and oral cavity cancers. Additionally, due to a mutation in the VHL gene that leads to constitutive HIF-1 activation, cancers such as clear cell carcinoma of the kidney have been shown to upregulate CA IX up to 150-fold over basal levels. In normal cells, however, CA IX is only expressed in epithelial cells of the stomach and gallbladder where it appears to be catalytically inactive.

As CA IX has been touted as an excellent target for the specific delivery of imaging agents, both small molecule- and antibody-conjugates have been created to image hypoxic tumors. For example, CA IX-specific ligands have been used to image moue xenograft models of colon, renal and cervical cancers. CA IX-specific antibodies have been used to image mouse xenograft models of clear cell renal, head & neck, colon and cervical cancers in addition to human patients with clear cell renal carcinomas.

Furthermore, while much effort has been made towards CA IX-targeted imaging agents, conversely, very little research has been conducted towards targeting therapeutics to CA IX expressing cancers. The few reports of CA IX-targeted therapies involve the use of anti-CA IX antibodies either directly labeled with a therapeutic radionuclide (Muselaers C H, Oosterwijk E, Bos D L, Oyen W J, Mulders P F, Boerman O C. Optimizing lutetium 177-anti-carbonic anhydrase IX radioimmunotherapy in an intraperitoneal clear cell renal cell carcinoma xenograft model. *Mol Imaging.* 2014. 13:1-7) or conjugated to drug containing liposomes (Wong B C, Zhang H, Qin L, Chen H, Fang C, Lu A, Yang Z. Carbonic anhydrase IX-directed immunoliposomes for targeted drug delivery to human lung cancer cells in vitro. *Drug Des Devel Ther.* 2014, 8:993-1001). To our knowledge, the efficacy of a small molecule CA IX ligand directly conjugated to a highly potent anti-cancer drug has not been reported in an in vivo mouse xenograft model.

While small molecule conjugates have primarily used PET and fluorescence to image hypoxic tumors, there is a need for the development of further selective imaging agents. Furthermore, there is an unmet need for the development of CA IX targeted therapeutics.

SUMMARY

In some embodiments, the disclosure provides a conjugate comprising a CA IX ligand covalently bound through a linker to at least one agent selected from the group consisting of a therapeutic agent and an imaging agent; or a pharmaceutically acceptable salt thereof. In some embodiments, the disclosure provides a conjugate comprising a CA IX ligand covalently bound to at least one agent selected from the group consisting of a therapeutic agent and an imaging agent; or a pharmaceutically acceptable salt thereof. In some embodiments, the disclosure provides a conjugate of the formula B-L-A, wherein B is a binding ligand of carbonic anhydrase IX, L is an optional linker, and A is a therapeutic agent or an imaging agent. In some aspects of these embodiments, the CA IX ligand is an aryl sulfonamide containing compound.

In other embodiments, the disclosure provide a method of imaging a population of cells in an subject, comprising
  a. administering to the subject an effective amount of a conjugate comprising a CA IX ligand covalently bound through a linker to at least one imaging agent; or a pharmaceutically acceptable salt thereof.

In other embodiments, the disclosure provide a method of imaging a population of cells in an subject, comprising
  a. administering to the subject an effective amount of a conjugate of the formula B-L-A, wherein B is a binding ligand of carbonic anhydrase IX, L is an optional linker, and A is an imaging agent. In some aspects of these embodiments, the CA IX ligand is an aryl sulfonamide containing compound. In some aspects of these embodiments, the CA IX ligand is of the formula

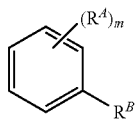

wherein $R^A$, $R^B$ and m are as defined herein.

In other embodiments, the present disclosure provides a composition comprising a conjugate as described herein, or a pharmaceutically acceptable salt thereof, and optionally at least one pharmaceutically acceptable excipient.

In other embodiments, the present disclosure provides a conjugate as described herein for use in a method of imaging a population of cells in a subject. In some aspects of these embodiments, the method comprises administering to the subject an amount of the conjugate effective for imaging the cells.

In other embodiments, the present disclosure provides a use of a conjugate as described herein in the preparation of a medicament useful for imaging a population of cells in a subject. In some aspects of these embodiments, the method comprises administering to the subject an amount of the conjugate effective for imaging the cells.

In other embodiments, the present disclosure provides a method of treating cancer in a subject, comprising, a. administering to the subject an effective amount of a conjugate described herein; or a pharmaceutically acceptable salt thereof. In other embodiments, the method further comprises, b. identifying a patient for treatment by imaging. In some aspects of these embodiments, the imaging comprises c. administering to the patient an effective amount of a conjugate wherein the agent is an imaging agent as described herein; and d. identifying the patient as having a CA IX expressing cancer. In some aspects of these embodiments, the cancer is selected from the group consisting of lung, colorectal, gastric, pancreatic, breast, cervical, bladder, ovarian, brain, head & neck, oral and kidney cancer.

In other embodiments, the present disclosure provides a conjugate as described herein for use in a method of treating cancer in a subject. In some aspects of these embodiments, the method comprises administering to the subject an amount of the conjugate effective for treating the cancer. In some aspects of these embodiments, the cancer is selected from the group consisting of lung, colorectal, gastric, pancreatic, breast, cervical, bladder, ovarian, brain, head & neck, oral and kidney cancer.

In other embodiments, the present disclosure provides a use of a conjugate as described herein in the preparation of a medicament useful for treating cancer in a subject. In some aspects of these embodiments, the method comprises administering to the subject an amount of the conjugate effective for treating the cells. In some aspects of these embodiments, the cancer is selected from the group consisting of lung, colorectal, gastric, pancreatic, breast, cervical, bladder, ovarian, brain, head & neck, oral and kidney cancer.

In some embodiments, the present disclosure provides a composition comprising a conjugate as described herein, or a pharmaceutically acceptable salt thereof, and optionally at least one pharmaceutically acceptable excipient.

In some embodiments, the present disclosure provides a method of imaging a population of cells in a subject, comprising a. administering to the subject a conjugate of the disclosure, or a pharmaceutically acceptable salt thereof, to provide the conjugate bound to cells expressing a CA IX protein; b. irradiating the conjugate bound to cells by irradiation with near-infrared wavelength light, and c. detecting light emitted from the cells at an emission wavelength.

In some embodiments, the present disclosure provides a method of imaging a population of cells in a subject, comprising a. administering to the subject a conjugate of the disclosure, or a pharmaceutically acceptable salt thereof, to provide the conjugate bound to cells expressing a CA IX protein; and b. visualizing the conjugate bound to cells by irradiation with near-infrared wavelength light.

In some embodiments, the present disclosure provides a method of imaging a cancer in a subject, comprising a. administering to the subject a conjugate of the disclosure, or a pharmaceutically acceptable salt thereof, to provide the conjugate bound to cancer cells expressing a CA IX protein; b. irradiating the conjugate bound to cancer cells with near-infrared wavelength light, and c. detecting light emitted from the cancer cells at an emission wavelength. In some aspects of these embodiments, the cancer is selected from the group consisting of lung, colorectal, gastric, pancreatic, breast, cervical, bladder, ovarian, brain, head & neck, oral and kidney cancer.

In some embodiments, the present disclosure provides a method of imaging a cancer in a subject, comprising a. administering to the subject a conjugate of the disclosure, or a pharmaceutically acceptable salt thereof, to provide the conjugate bound to cancer cells expressing a CA IX protein; and b. visualizing the conjugate bound to cancer cells by irradiation with near-infrared wavelength light. In some aspects of these embodiments, the cancer is selected from the group consisting of lung, colorectal, gastric, pancreatic, breast, cervical, bladder, ovarian, brain, head & neck, oral and kidney cancer.

In other embodiments, the present disclosure provides a conjugate of the disclosure, or a pharmaceutically acceptable salt thereof, for use in a method of imaging a cancer in a patient. In some aspects of these embodiments, the method comprises, a. administering to the patient the conjugate, or a pharmaceutically acceptable salt thereof, to provide the conjugate bound to cells expressing a CA IX protein; and b. visualizing the conjugate bound to cells by irradiation with near-infrared wavelength light. In some aspects of these embodiments, the method comprises, a. administering to the subject a conjugate of the disclosure, or a pharmaceutically acceptable salt thereof, to provide the conjugate bound to cancer cells expressing a CA IX protein; b. irradiating the conjugate bound to cancer cells with near-infrared wavelength light, and c. detecting light emitted from the cancer cells at an emission wavelength. In some aspects of these embodiments, the cancer is selected from the group consisting of lung, colorectal, gastric, pancreatic, breast, cervical, bladder, ovarian, brain, head & neck, oral and kidney cancer.

In some embodiments, the present disclosure provides a use of a compound of the disclosure, or a pharmaceutically acceptable salt thereof, in the preparation of a medicament useful for imaging a cancer in a patient. In some aspects of these embodiments, the method comprises, a. administering to the patient the conjugate, or a pharmaceutically acceptable salt thereof, to provide the conjugate bound to cells expressing a CA IX protein; and b. visualizing the conjugate bound to cells by irradiation with near-infrared wavelength light. In some aspects of these embodiments, the method comprises, a. administering to the subject a conjugate of the disclosure, or a pharmaceutically acceptable salt thereof, to provide the conjugate bound to cancer cells expressing a CA IX protein; b. irradiating the conjugate bound to cancer cells with near-infrared wavelength light, and c. detecting light emitted from the cancer cells at an emission wavelength. In some aspects of these embodiments, the cancer is selected from the group consisting of lung, colorectal, gastric, pancreatic, breast, cervical, bladder, ovarian, brain, head & neck, oral and kidney cancer.

In some embodiments, the present disclosure provides a method of imaging a population of cells in vitro, comprising a. contacting the cells with a conjugate of the disclosure to provide labelled cells, and b. visualizing the labelled cells with a fluorescent light source. In some embodiments, the present disclosure provides a method of imaging a population of cells in vitro, comprising a. contacting the cells with a conjugate of the disclosure to provide labelled cells, b. irradiating the conjugate bound to the cells with near-infrared wavelength light, and c. detecting light emitted from the cells at an emission wavelength.

In some embodiments, the present disclosure provides a method of imaging a population of cells in a subject, comprising a. administering to the subject a conjugate of the disclosure, or a pharmaceutically acceptable salt thereof, to provide the conjugate bound to cells expressing a CA IX protein; b. detecting a radionuclide bound to the conjugate.

Embodiments of the invention are further described by the following enumerated clauses. It will be understood that any of the embodiments described herein can be used in connection with any other embodiments described herein to the extent that the embodiments do not contradict one another.

1. A conjugate of the formula B-L-A, or a pharmaceutically acceptable salt thereof, wherein B is a binding ligand of carbonic anhydrase IX of the formula

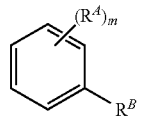

wherein each $R^4$ is independently selected from the group consisting of H, halogen, —$OR^1$, —$OC(O)R^1$, —$OC(O)NR^1R^2$, —$OS(O)R^1$, —$OS(O)_2R^1$, —$SR^1$, —$S(O)R^1$, —$S(O)_2R^1$, —$S(O)NR^1R^2$, —$S(O)_2NR^1R^2$, —$OS(O)NR^1R^2$, —$OS(O)_2NR^1R^2$, —$NR^1R^2$, —$NR^1C(O)R^1$, —$NR^1C(O)OR^2$, —$NR^1C(O)NR^1R^2$, —$NR^1S(O)R^2$, —$NR^1S(O)_2R^2$, —$NR^1S(O)NR^1R^2$, —$NR^1S(O)_2NR^1R^2$, —$C(O)R^1$, —$C(O)OR^1$, and —$C(O)NR^1R^2$;

$R^B$ is —$OR^3$, —$SR^3$, —$NR^3R^4$, —$S(O)_2R^3$, —$NR^4C(O)R^3$ or —$NR^4C(O)NR^3R^4$;

$R^3$ is independently $C_1$-$C_{10}$ alkyl, $C_2$-$C_{10}$ alkenyl or phenyl, each independently substituted with one substituent selected from the group consisting of N($R^5$)—*, —N($R^5$)—$C_1$-$C_6$ alkyl-N($R^6$)—*, —OC(O)—*, —OC(O)N($R^5$)—*, —C(O)—*, —C(O)O—*, and —C(O)N($R^5$)—*; and each remaining hydrogen atom in $C_1$-$C_{10}$ alkyl, $C_2$-$C_{10}$ alkenyl or phenyl is independently optionally substituted by $C_1$-$C_{10}$ alkyl, $C_2$-$C_{10}$ alkenyl, halogen, —$OR^1$, —$OC(O)R^1$, —$OC(O)NR^1R^2$, —$OS(O)R^1$, —$OS(O)_2R^1$, —$SR^1$, —$S(O)R^1$, —$S(O)_2R^1$, —$S(O)NR^1R^2$, —$S(O)_2NR^1R^2$, —$OS(O)NR^1R^2$, —$OS(O)_2NR^1R^2$, —$NR^1R^2$, —$NR^1C(O)R^1$, —$NR^1C(O)OR^2$, —$NR^1C(O)NR^1R^2$, —$NR^1S(O)R^2$, —$NR^1S(O)_2R^2$, —$NR^1S(O)NR^1R^2$, —$NR^1S(O)_2NR^1R^2$, —$C(O)R^1$, —$C(O)OR^1$, and —$C(O)NR^1R^2$ each $R^1$, $R^2$, $R^4$, $R^5$ and $R^6$ is independently selected from the group consisting of H, $C_1$-$C_6$ alkyl, $C_2$-$C_6$ alkenyl, $C_2$-$C_6$ alkynyl, and $C_3$-$C_9$ cycloalkyl;

L is an optional linker;

A is a therapeutic agent or an imaging agent;

m is an integer from 1 to 5; and

* represents a point of attachment to L or A.

2. The conjugate of clause 1, or a pharmaceutically acceptable salt thereof, wherein the carbonic anhydrase IX ligand is of the formula

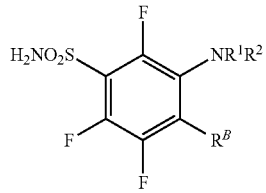

wherein $R^B$ is —$OR^3$, —$SR^3$, —$NR^3R^4$, —$S(O)_2R^3$, —$NR^4C(O)R^3$ or —$NR^4C(O)NR^3R^4$;

$R^3$ is independently $C_1$-$C_{10}$ alkyl, $C_2$-$C_{10}$ alkenyl or phenyl, each independently substituted with one substituent selected from the group consisting of —$NR^5$—*, —N($R^5$)—$C_1$-$C_6$ alkyl-N($R^6$)—*, —OC(O)—*, —OC(O)N($R^5$)—*, —C(O)—*, —C(O)O—*, and —C(O)N($R^5$)—*;

each $R^1$, $R^2$, $R^4$, $R^5$ and $R^6$ is independently selected from the group consisting of H, $C_1$-$C_6$ alkyl, $C_2$-$C_6$ alkenyl, $C_2$-$C_6$ alkynyl, and $C_3$-$C_9$ cycloalkyl; and

* represents a point of attachment to L or A.

3. The conjugate of clause 1 or 2, or a pharmaceutically acceptable salt thereof, wherein the carbonic anhydrase IX ligand is

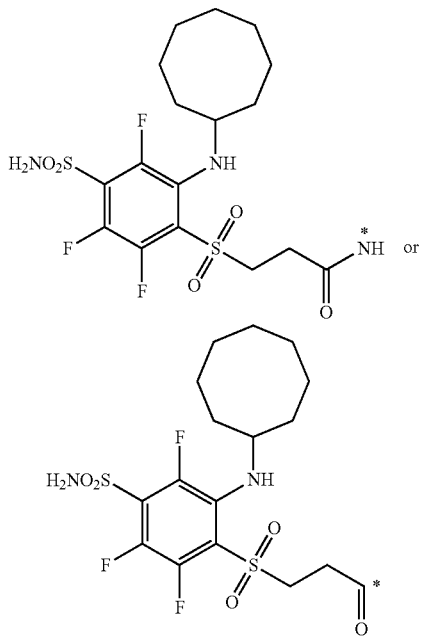

wherein * represents a point of attachment to the rest of the conjugate.

4. The conjugate of any one of the preceding clauses, or a pharmaceutically acceptable salt thereof, wherein the linker comprises a portion selected from the group consisting of —C(O)(C$_1$-C$_{12}$ alkyl)C(O)—, —NH—C$_1$-C$_{12}$ alkyl-NH—, —N(C$_1$-C$_6$ alkyl)-C$_1$-C$_{12}$ alkyl-N(C$_1$-C$_6$ alkyl)-, —C(O)CH$_2$CH$_2$(OCH$_2$CH$_2$)$_q$NH—, —C(O)CH$_2$CH$_2$(OCH$_2$CH$_2$)$_q$N(C$_1$-C$_6$ alkyl)-, —(CH$_2$CH$_2$O)$_q$CH$_2$CH$_2$C(O)—, —NH(CH$_2$CH$_2$O)$_q$CH$_2$CH$_2$C(O)—, and —N(C$_1$-C$_6$ alkyl)(CH$_2$CH$_2$O)$_q$CH$_2$CH$_2$C(O)—; wherein q is an integer from 1 to 40.

5. The conjugate of any one of the preceding clauses, or a pharmaceutically acceptable salt thereof, wherein the linker comprises at least one amino acid.

6. The conjugate of any one of the preceding clauses, or a pharmaceutically acceptable salt thereof, wherein the linker comprises at least one amino acid selected from the group consisting of 3-aminoalanine, aspartic acid, cysteine, and arginine.

7. The conjugate of any one of the preceding clauses, or a pharmaceutically acceptable salt thereof, wherein the linker comprises a releasable linker.

8. The conjugate of any one of the preceding clauses, or a pharmaceutically acceptable salt thereof, wherein the linker comprises a disulfide portion.

9. The conjugate of any one of the preceding clauses, or a pharmaceutically acceptable salt thereof, wherein the linker comprises a hydrazine portion.

10. The conjugate of any one of the preceding clauses, or a pharmaceutically acceptable salt thereof, wherein the linker comprises a linker portion of the formula

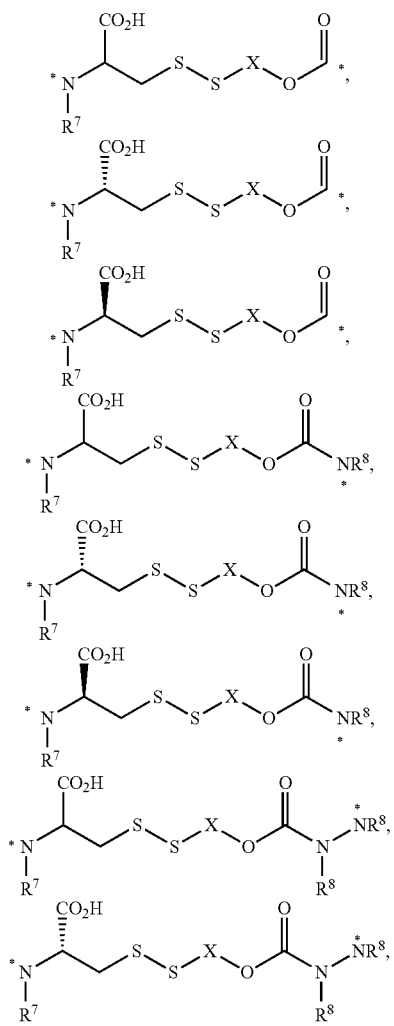

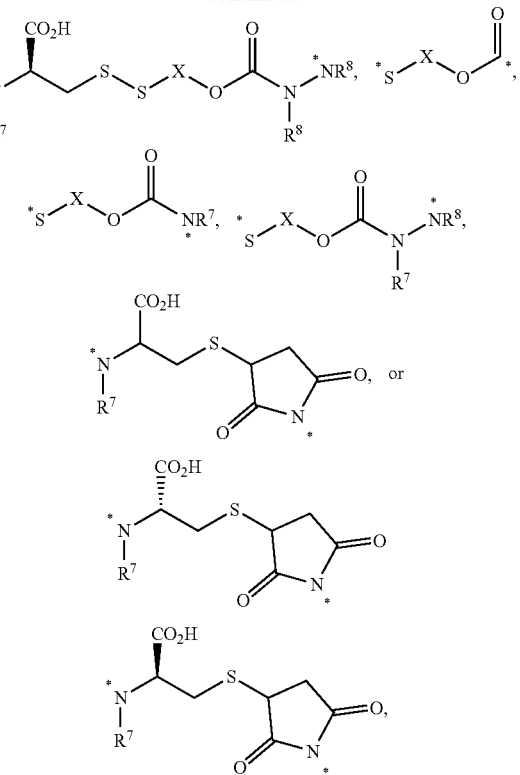

wherein
each $R^7$ and $R^8$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^9$, —OC(O)R$^9$, —OC(O)NR$^9$R$^{10}$, —OS(O)R$^9$, —OS(O)$_2$R$^9$, —SR$^9$, —S(O)R$^9$, —S(O)$_2$R$^9$, —S(O)NR$^9$R$^{10}$, —S(O)$_2$NR$^9$R$^{10}$, —OS(O)NR$^9$R$^{10}$, —OS(O)$_2$NR$^9$R$^{10}$, —NR$^9$R$^{10}$, —NR$^9$C(O)R$^{10}$, —NR$^9$C(O)OR$^{10}$, —NR$^9$C(O)NR$^{11}$R$^{12}$, —NR$^9$S(O)R$^{10}$, —NR$^9$S(O)$_2$R$^{10}$, —NR$^9$S(O)NR$^{11}$R$^{12}$, —NR$^9$S(O)$_2$NR$^{11}$R$^{12}$, —C(O)R$^9$, —C(O)OR$^9$ or —C(O)NR$^9$R$^{10}$;

each X is independently $C_1$-$C_6$ alkyl or $C_6$-$C_{10}$ aryl-($C_1$-$C_6$ alkyl), wherein each hydrogen atom in $C_1$-$C_6$ alkyl and $C_6$-$C_{10}$ aryl-($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^9$, —OC(O)R$^9$, —OC(O)NR$^9$R$^{10}$, —OS(O)R$^9$, —OS(O)$_2$R$^9$, —SR$^9$, —S(O)R$^9$, —S(O)$_2$R$^9$, —S(O)NR$^9$R$^{10}$, —S(O)$_2$NR$^9$R$^{10}$, —OS(O)NR$^9$R$^{10}$, —OS(O)$_2$NR$^9$R$^{10}$, —NR$^9$R$^{10}$, —NR$^9$C(O)R$^{10}$, —NR$^9$C(O)OR$^{10}$, —NR$^9$C(O)NR$^{11}$R$^{12}$, —NR$^9$S(O)R$^{10}$, —NR$^9$S(O)$_2$R$^{10}$, —NR$^9$S(O)NR$^{11}$R$^{12}$, —NR$^9$S(O)$_2$NR$^{11}$R$^{12}$, —C(O)R$^9$, —C(O)OR$^9$ or —C(O)NR$^9$R$^{10}$;

each $R^9$, $R^{10}$, $R^{11}$ and $R^{12}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and each * represents a covalent bond to the rest of the conjugate.

11. The conjugate of any one of the preceding clauses, or a pharmaceutically acceptable salt thereof, comprising the formula

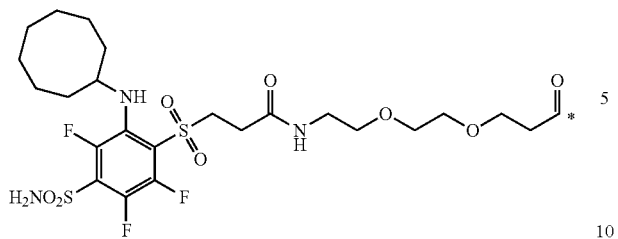

wherein * represents a point of attachment to the rest of the conjugate.

12. The conjugate of any one of clauses 1 to 10, or a pharmaceutically acceptable salt thereof, comprising the formula

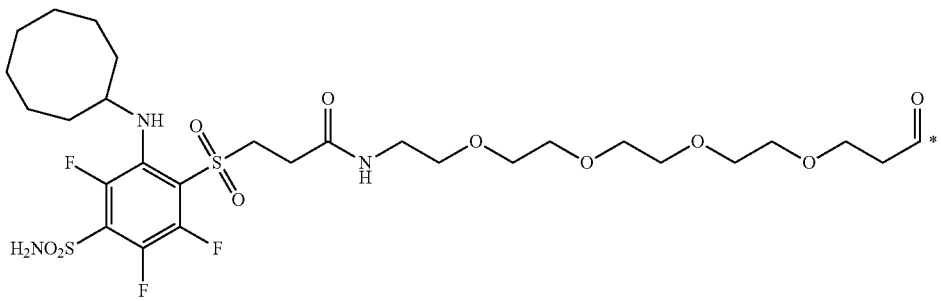 [SMILES: NS(=O)(=O)c1c(F)c(F)c(S(=O)(=O)CCC(=O)NCCOCCOCCOCCOCCC=O)c(NC2CCCCCCC2)c1F]

wherein * represents a covalent bond to the rest of the conjugate.

13. The conjugate of any one of clauses 1 to 10, or a pharmaceutically acceptable salt thereof, comprising the formula

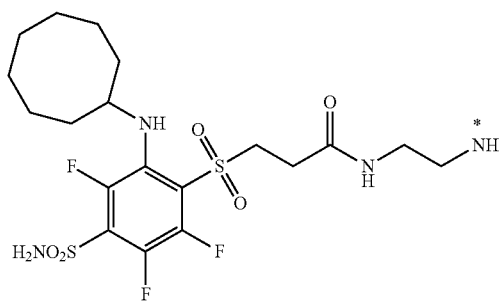 [SMILES: NCCNC(=O)CCS(=O)(=O)c1c(F)c(F)c(S(N)(=O)=O)c(F)c1NC1CCCCCCC1]

wherein * represents a covalent bond to the rest of the conjugate.

14. The conjugate of any one of the preceding clauses, or a pharmaceutically acceptable salt thereof, comprising a linker portion having the amino acid sequence 3-amino-alanine-Asp-Cys.

15. The conjugate of any one of clauses 1 to 13, or a pharmaceutically acceptable salt thereof, comprising a linker portion having the amino acid sequence Asp-Arg-Asp-3-amino-alanine-Asp-Cys.

16. The conjugate of any one of clauses 4 to 15, or a pharmaceutically acceptable salt thereof, wherein q is 2.

17. The conjugate of any one of clauses 4 to 15, or a pharmaceutically acceptable salt thereof, wherein q is 4.

18. The conjugate of any one of the preceding clauses, or a pharmaceutically acceptable salt thereof, wherein A is an imaging agent.

19. The conjugate of any one of the preceding clauses, or a pharmaceutically acceptable salt thereof, wherein A is a fluorescent dye.

20. The conjugate of any one of the preceding clauses, or a pharmaceutically acceptable salt thereof, wherein A is fluorescein dye of the formula

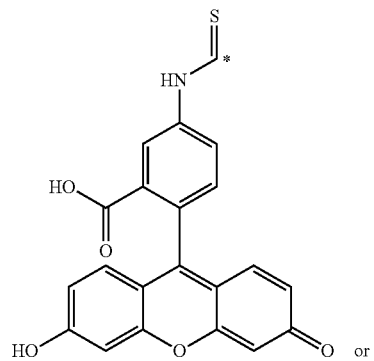

or

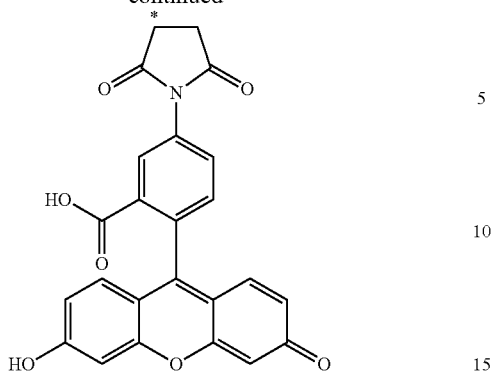
wherein * represents a covalent bond to the rest of the conjugate.
21. The conjugate of clause 1, selected from the group consisting of
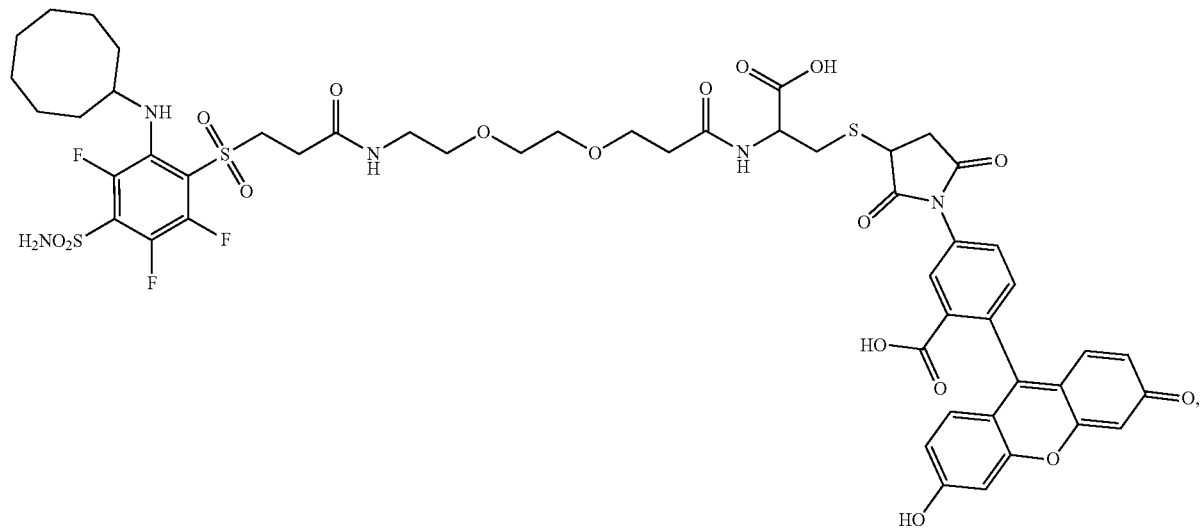
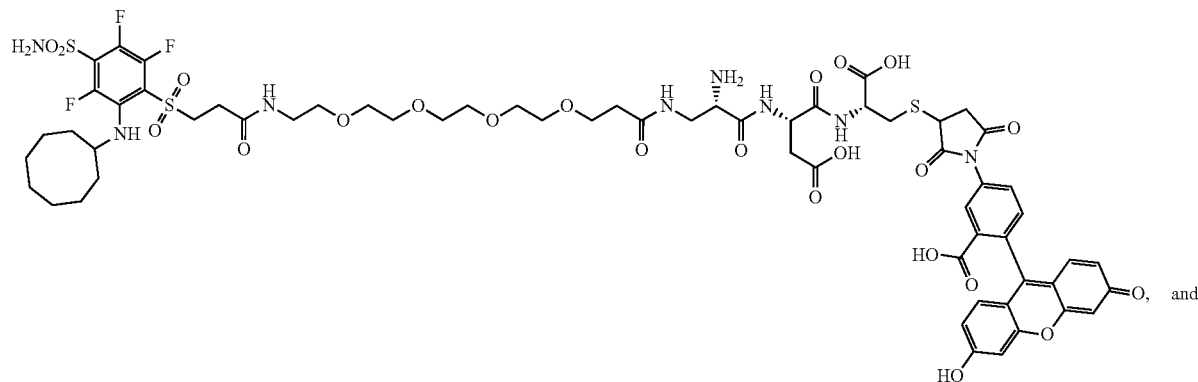

-continued

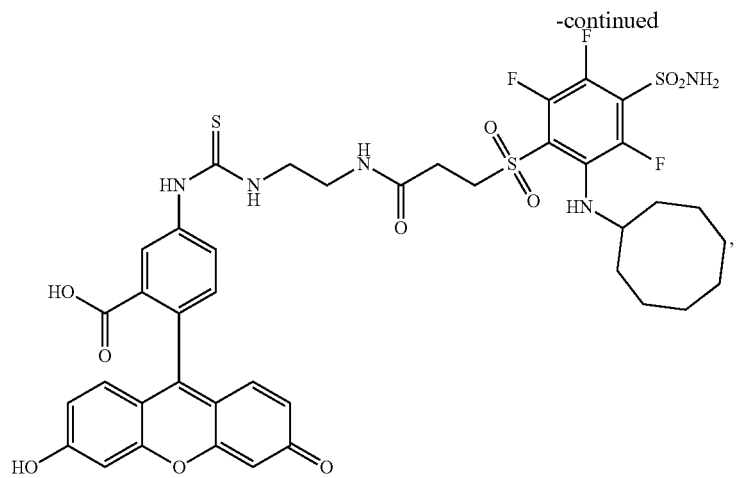

or a pharmaceutically acceptable salt thereof.

22. The conjugate of any one of clauses 1-18, or a pharmaceutically acceptable salt thereof, wherein A is a radio-imaging agent.

23. The conjugate of any one of clauses 1-18, or a pharmaceutically acceptable salt thereof, wherein A comprises radioactive isotope of a metal coordinated to a chelating group.

24. The conjugate of any one of clauses 1-18, 22, or 23, or a pharmaceutically acceptable salt thereof, comprising a radioactive metal is selected from the group consisting of $^{111}$In, $^{99m}$Tc, $^{64}$Cu, $^{67}$Cu, $^{67}$Ga, and $^{68}$Ga.

25. The conjugate of any one of clauses 1-18, or 22-24, or a pharmaceutically acceptable salt thereof, comprising a radioactive metal that is $^{64}$Cu.

26. The conjugate of any one of clauses 1-18, or 22-25, or a pharmaceutically acceptable salt thereof, comprising a chelating group selected from the group consisting of a radical of DOTA, NOTA, TETA, DOTAGA, NODAGA, DTPA, PCTA, and NETA.

27. The conjugate of any one of clauses 1-18, or 22-26, or a pharmaceutically acceptable salt thereof, comprising a chelating group that is a radical of NODAGA.

28. The conjugate of any one of clauses 1-18, or 22-27, or a pharmaceutically acceptable salt thereof, comprising a chelating group of the formula

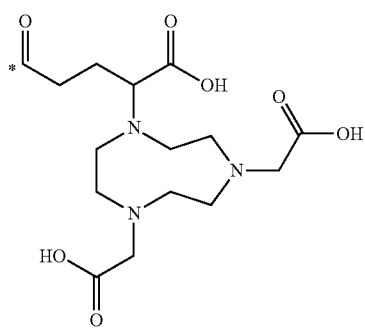 [SMILES: O=CCCC(C(=O)O)N1CCN(CC(=O)O)CCN(CC(=O)O)CC1]

wherein * represents a covalent bond to the rest of the conjugate.

29. The conjugate of any one of clauses 1-18, or 22-28, or a pharmaceutically acceptable salt thereof, comprising the formula

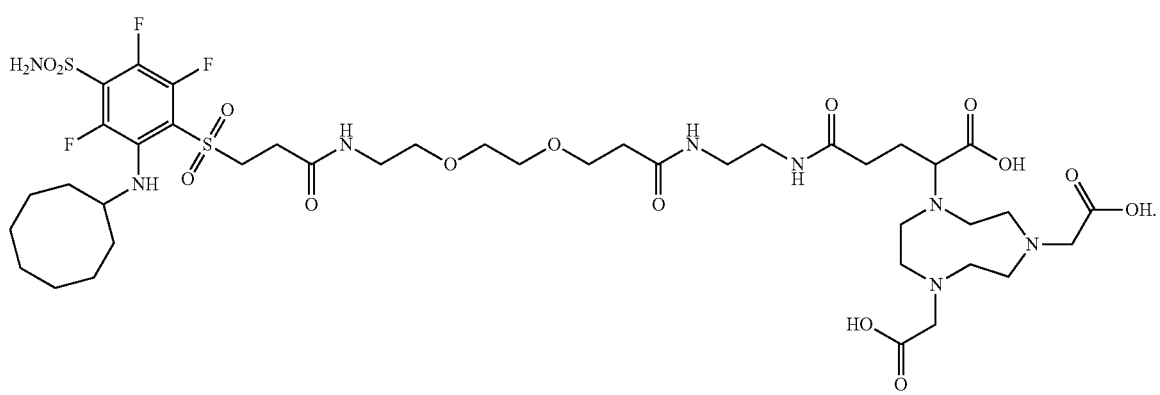 [SMILES: NS(=O)(=O)c1c(F)c(F)c(S(=O)(=O)CCC(=O)NCCOCCOCCC(=O)NCCNC(=O)CCC(C(=O)O)N2CCN(CC(=O)O)CCN(CC(=O)O)CC2)c(NC2CCCCCCC2)c1F]

30. The conjugate of any one of clauses 1 to 17, or a pharmaceutically acceptable salt thereof, wherein A is a therapeutic agent.

31. The conjugate of any one of clauses 1 to 17, or a pharmaceutically acceptable salt thereof, wherein the therapeutic agent is a tubulysin.

32. The conjugate of clause 1, selected from the group consisting of

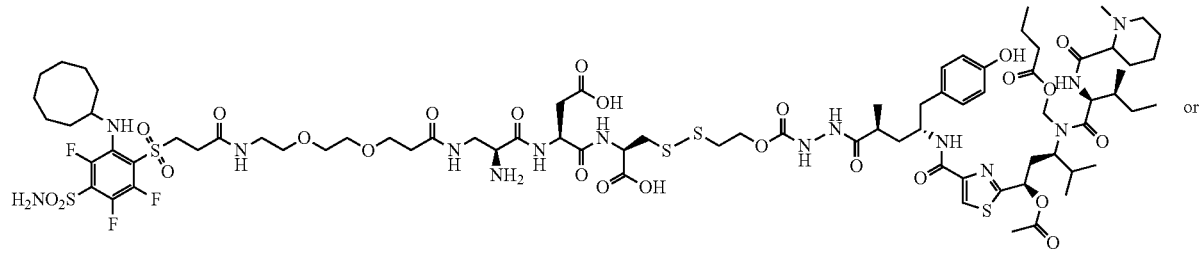

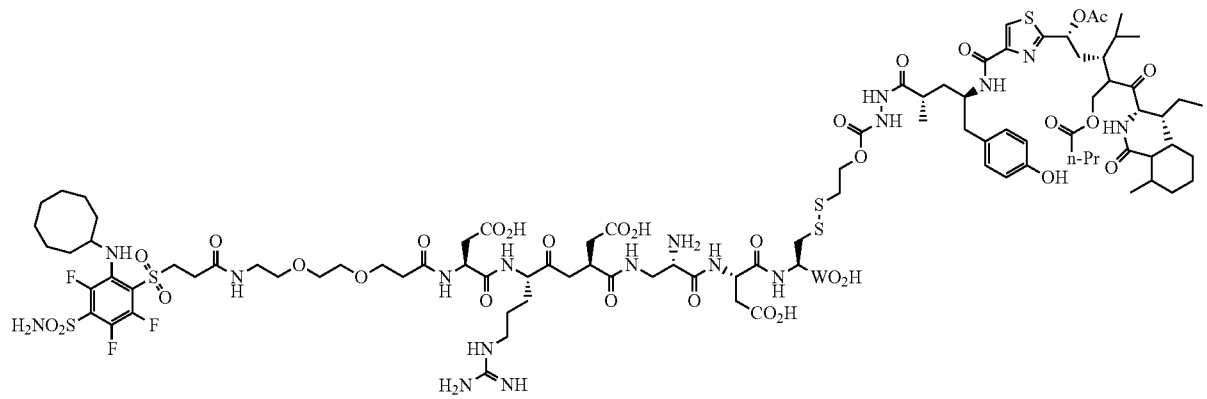

or a pharmaceutically acceptable salt thereof.

33. The conjugate of any one of clauses 1 to 17, or a pharmaceutically acceptable salt thereof, wherein the therapeutic agent is a maytansine.

34. The conjugate of clause 1, having the formula

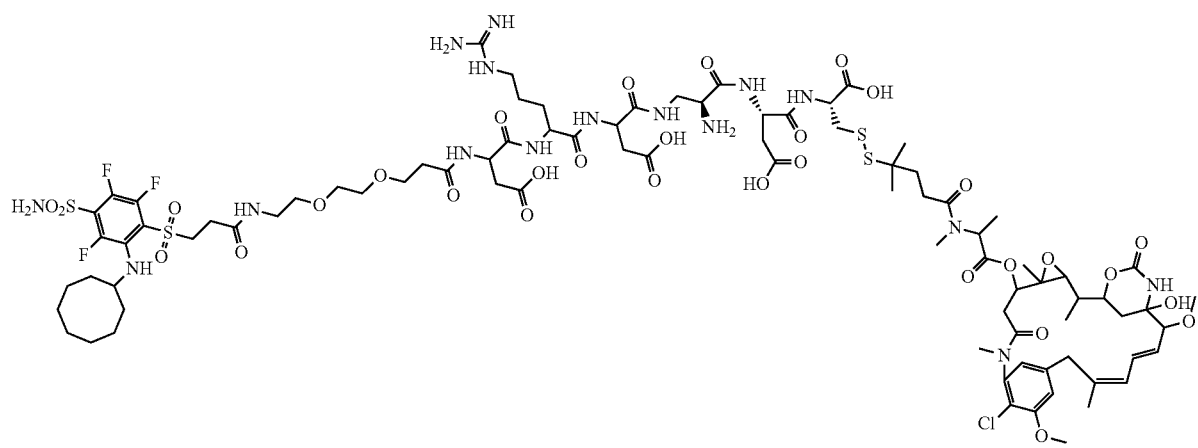 [SMILES: COc1cc2cc(c1Cl)N(C)C(=O)CC(OC(=O)C(C)N(C)C(=O)CCC(C)(C)SSC[C@H](NC(=O)[C@H](CC(=O)O)NC(=O)[C@@H](N)CNC(=O)C(CC(=O)O)NC(=O)C(CCCNC(=N)N)NC(=O)C(CC(=O)O)NC(=O)CCOCCOCCNC(=O)CCS(=O)(=O)c1c(F)c(F)c(S(N)(=O)=O)c(F)c1NC1CCCCCCC1)C(=O)O)C1(C)OC1C(C)C1CC(O)(NC(=O)O1)C(OC)/C=C/C=C(/C)C2]

or a pharmaceutically acceptable salt thereof.

35. A method of imaging a population of cells in a subject, comprising a. administering to the subject an effective amount of a conjugate of the formula B-L-A, wherein B is a carbonic anhydrase IX ligand of the formula

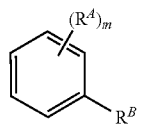

wherein each $R^A$ is independently selected from the group consisting of H, halogen, —$OR^1$, —$OC(O)R^1$, —$OC(O)NR^1R^2$, —$OS(O)R^1$, —$OS(O)_2R^1$, —$SR^1$, —$S(O)R^1$, —$S(O)_2R^1$, —$S(O)NR^1R^2$, —$S(O)_2NR^1R^2$, —$OS(O)NR^1R^2$, —$OS(O)_2NR^1R^2$, —$NR^1R^2$, —$NR^1C(O)R^1$, —$NR^1C(O)OR^2$, —$NR^1C(O)NR^1R^2$, —$NR^1S(O)R^2$, —$NR^1S(O)_2R^2$, —$NR^1S(O)NR^1R^2$, —$NR^1S(O)_2NR^1R^2$, —$C(O)R^1$, —$C(O)OR^1$, and —$C(O)NR^1R^2$;

$R^B$ is —$OR^3$, —$SR^3$, —$NR^3R^4$, —$S(O)_2R^3$, —$NR^4C(O)R^3$ or —$NR^4C(O)NR^3R^4$;

$R^3$ is independently $C_1$-$C_{10}$ alkyl, $C_2$-$C_{10}$ alkenyl or phenyl, each independently substituted with one substituent selected from the group consisting of —$NR^5$—*, —$N(R^5)$—$C_1$-$C_6$ alkyl-$N(R^6)$—*, —$OC(O)$—*, —$OC(O)N(R^5)$—*, —$C(O)$—*, —$C(O)O$—*, and —$C(O)N(R^5)$—*;

each $R^1$, $R^2$, $R^4$, $R^5$ and $R^6$ is independently selected from the group consisting of H, $C_1$-$C_6$ alkyl, $C_2$-$C_6$ alkenyl, $C_2$-$C_6$ alkynyl, and $C_3$-$C_9$ cycloalkyl;

L is an optional linker;

A is a therapeutic agent or an imaging agent;

m is an integer from 1 to 5; and

* represents a point of attachment to L or A.

36. The method of clause 35, wherein the carbonic anhydrase IX ligand is of the formula

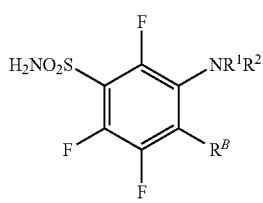

wherein $R^B$ is —$OR^3$, —$SR^3$, —$NR^3R^4$, —$S(O)_2R^3$, —$NR^4C(O)R^3$ or —$NR^4C(O)NR^3R^4$;

$R^3$ is independently $C_1$-$C_{10}$ alkyl, $C_2$-$C_{10}$ alkenyl or phenyl, each independently substituted with one substituent selected from the group consisting of —$NR^5$—*, —$N(R^5)$—$C_1$-$C_6$ alkyl-$N(R^6)$—*, —$OC(O)$—*, —$OC(O)N(R^5)$—*, —$C(O)$—*, —$C(O)O$—*, and —$C(O)N(R^5)$—*;

each $R^1$, $R^2$, $R^4$, $R^5$ and $R^6$ is independently selected from the group consisting of H, $C_1$-$C_6$ alkyl, $C_2$-$C_6$ alkenyl, $C_2$-$C_6$ alkynyl, and $C_3$-$C_9$ cycloalkyl; and

* represents a point of attachment to L or A.

37. The method of clause 35 or 36, or a pharmaceutically acceptable salt thereof, wherein the carbonic anhydrase IX ligand is

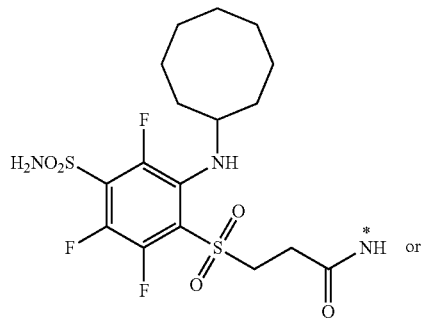

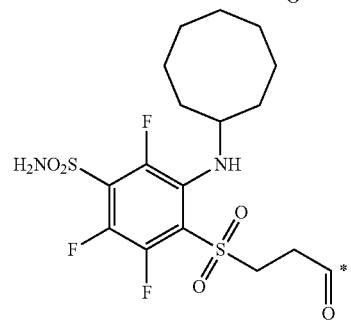

wherein * represents a point of attachment to the rest of the conjugate.

38. The method of any one of clauses 35 to 37, or a pharmaceutically acceptable salt thereof, wherein the linker comprises a portion selected from the group consisting of —$C(O)(C_1$-$C_{12}$ alkyl)$C(O)$—, —NH—$C_1$-$C_{12}$ alkyl-NH—, —$N(C_1$-$C_6$ alkyl)-$C_1$-$C_{12}$ alkyl-$N(C_1$-$C_6$ alkyl)-, —$C(O)CH_2CH_2(OCH_2CH_2)_qNH$—, —$C(O)CH_2CH_2(OCH_2CH_2)_qN(C_1$-$C_6$ alkyl)-, —$(CH_2CH_2O)_qCH_2CH_2C(O)$—, —$NH(CH_2CH_2O)_qCH_2CH_2C(O)$—, and —$N(C_1$-$C_6$ alkyl)$(CH_2CH_2O)_qCH_2CH_2C(O)$—; wherein q is an integer from 1 to 40.

39. The method of any one of clauses 35 to 38, or a pharmaceutically acceptable salt thereof, wherein the linker comprises at least one amino acid.

40. The method of any one of clauses 35 to 39, or a pharmaceutically acceptable salt thereof, wherein the linker comprises at least one amino acid selected from the group consisting of 3-aminoalanine, aspartic acid, cysteine, and arginine.

41. The method of any one of clauses 35 to 40, or a pharmaceutically acceptable salt thereof, wherein the linker comprises a releasable linker.

42. The method of any one of clauses 35 to 41, or a pharmaceutically acceptable salt thereof, wherein the linker comprises a disulfide linker portion.

43. The method of any one of clauses 35 to 42, or a pharmaceutically acceptable salt thereof, wherein the linker comprises a hydrazine linker portion.

44. The method of any one of clauses 35 to 43, or a pharmaceutically acceptable salt thereof, wherein the linker comprises a linker portion of the formula

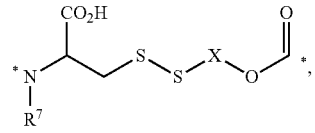

-continued

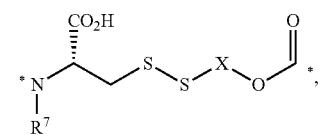

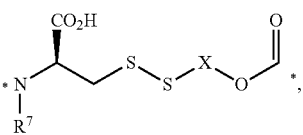

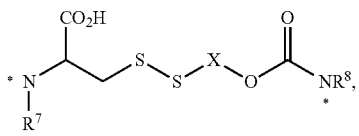

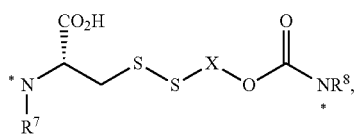

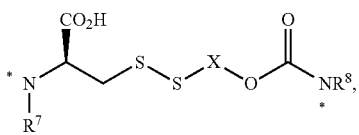

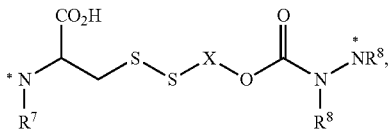

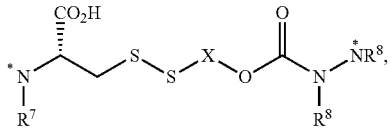

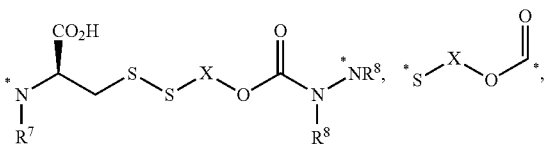

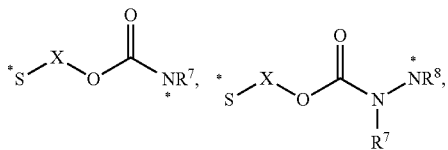

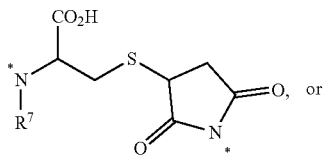, or

-continued

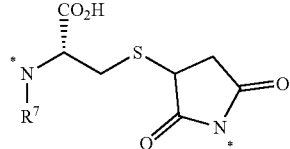

wherein
each $R^7$ and $R^8$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$OC(O)NR^9R^{10}$, —$OS(O)R^9$, —$OS(O)_2R^9$, —$SR^9$, —$S(O)R^9$, —$S(O)_2R^9$, —$S(O)NR^9R^{10}$, —$S(O)_2NR^9R^{10}$, —$OS(O)NR^9R^{10}$, —$OS(O)_2NR^9R^{10}$, —$NR^9R^{10}$, —$NR^9C(O)R^{10}$, —$NR^9C(O)OR^{10}$, —$NR^9C(O)NR^{11}R^{12}$, —$NR^9S(O)R^{10}$, —$NR^9S(O)_2R^{10}$, —$NR^9S(O)NR^{11}R^{12}$, —$NR^9S(O)_2NR^{11}R^{12}$, —$C(O)R^9$, —$C(O)OR^9$ or —$C(O)NR^9R^{10}$;

each X is independently $C_1$-$C_6$ alkyl or $C_6$-$C_{10}$ aryl-($C_1$-$C_6$ alkyl), wherein each hydrogen atom in $C_1$-$C_6$ alkyl and $C_6$-$C_{10}$ aryl-($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$OC(O)NR^9R^{10}$, —$OS(O)R^9$, —$OS(O)_2R^9$, —$SR^9$, —$S(O)R^9$, —$S(O)_2R^9$, —$S(O)NR^9R^{10}$, —$S(O)_2NR^9R^{10}$, —$OS(O)NR^9R^{10}$, —$OS(O)_2NR^9R^{10}$, —$NR^9R^{10}$, —$NR^9C(O)R^{10}$, —$NR^9C(O)OR^{10}$, —$NR^9C(O)NR^{11}R^{12}$, —$NR^9S(O)R^{10}$, —$NR^9S(O)_2R^{10}$, —$NR^9S(O)NR^{11}R^{12}$, —$NR^9S(O)_2NR^{11}R^{12}$, —$C(O)R^9$, —$C(O)OR^9$ or —$C(O)NR^9R^{10}$;

each $R^9$, $R^{10}$, $R^{11}$ and $R^{12}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and each * represents a covalent bond to the rest of the conjugate.

45. The method of any one of clauses 35 to 44, or a pharmaceutically acceptable salt thereof, comprising the formula

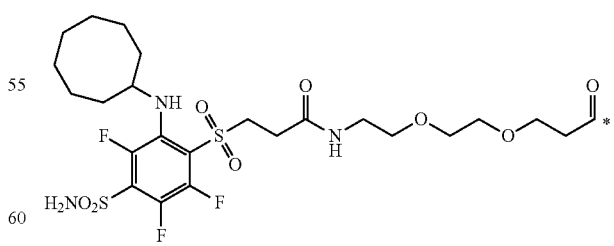

wherein * represents a point of attachment to the rest of the conjugate.

46. The method of any one of clauses 35 to 44, or a pharmaceutically acceptable salt thereof, comprising the formula

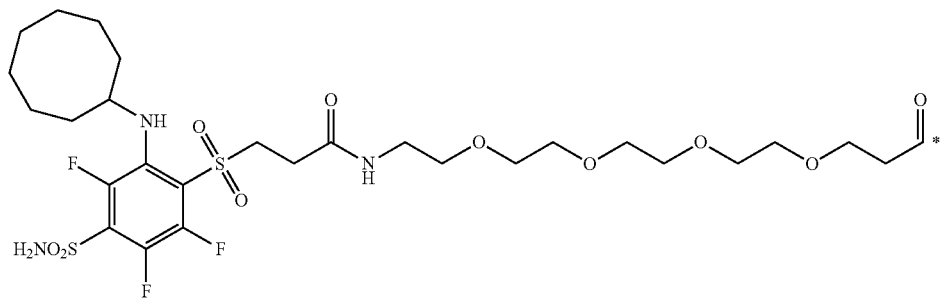 [SMILES: NS(=O)(=O)c1c(F)c(F)c(S(=O)(=O)CCC(=O)NCCOCCOCCOCCOCCC=O)c(NC2CCCCCCC2)c1F]

wherein * represents a covalent bond to the rest of the conjugate.

47. The method of any one of clauses 35 to 44, or a pharmaceutically acceptable salt thereof, comprising the formula

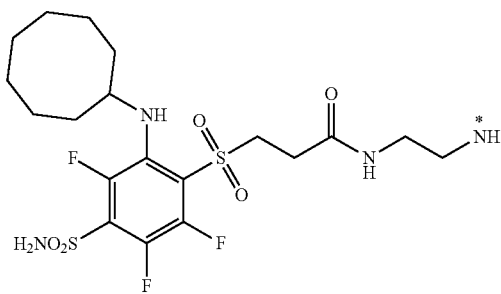 [SMILES: NCCNC(=O)CCS(=O)(=O)c1c(F)c(F)c(S(N)(=O)=O)c(F)c1NC1CCCCCCC1]

wherein * represents a covalent bond to the rest of the conjugate.

48. The method of any one of clauses 35 to 47, or a pharmaceutically acceptable salt thereof, comprising a linker portion having the amino acid sequence 3-amino-alanine-Asp-Cys.

49. The method of any one of clauses 35 to 48, or a pharmaceutically acceptable salt thereof, comprising a linker portion having the amino acid sequence Asp-Arg-Asp-3-amino-alanine-Asp-Cys.

50. The method of clause 38, or a pharmaceutically acceptable salt thereof, wherein q is 2.

51. The method of clause 38, or a pharmaceutically acceptable salt thereof, wherein q is 4.

52. The method of any one of clauses 35 to 51, or a pharmaceutically acceptable salt thereof, wherein A is an imaging agent.

53. The method of any one of clauses 35 to 52, or a pharmaceutically acceptable salt thereof, wherein A is a fluorescent dye.

54. The method of any one of clauses 35 to 53, or a pharmaceutically acceptable salt thereof, wherein A is fluorescein dye of the formula

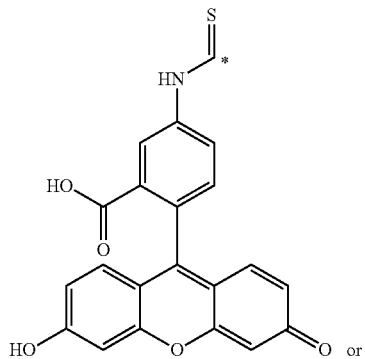

or

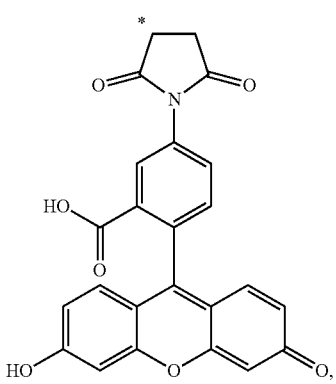

wherein * represents a covalent bond to the rest of the conjugate.

55. The method of clause 35, wherein the conjugate is selected from the group consisting of

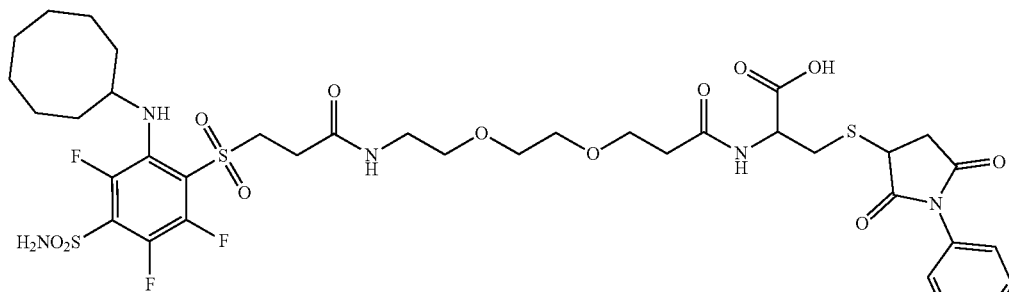

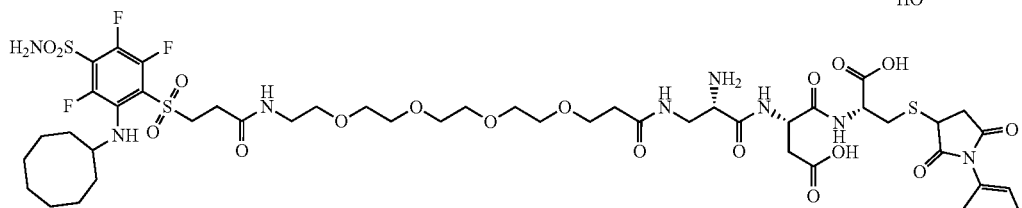

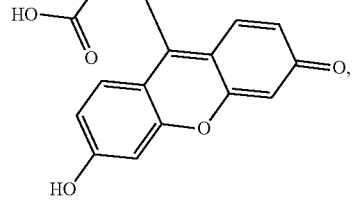

and

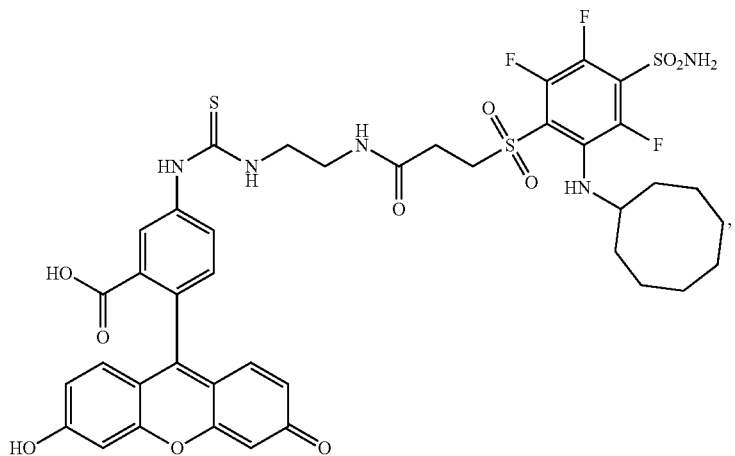

, or a pharmaceutically acceptable salt thereof.

56. The method of any one of clauses 35 to 52, or a pharmaceutically acceptable salt thereof, wherein A is a radio-imaging agent.

57. The method of any one of clauses 35 to 52, or 56, or a pharmaceutically acceptable salt thereof, wherein A comprises radioactive isotope of a metal coordinated to a chelating group.

58. The method of any one of clauses 35 to 52, 56 or 57, or a pharmaceutically acceptable salt thereof, comprising a radioactive metal is selected from the group consisting of $^{111}$In, $^{99m}$Tc, $^{64}$Cu, $^{67}$Cu, $^{67}$Ga, and $^{68}$Ga.

59. The method of any one of clauses 35 to 52, or 56 to 58, or a pharmaceutically acceptable salt thereof, comprising a radioactive metal that is $^{64}$Cu.

60. The method of any one of clauses 35 to 52, or 56 to 59, or a pharmaceutically acceptable salt thereof, comprising a chelating group selected from the group consisting of a radical of DOTA, NOTA, TETA, DOTAGA, NODAGA, DTPA, PCTA, and NETA.

61. The method of any one of clauses 35 to 52, or 56 to 60, or a pharmaceutically acceptable salt thereof, comprising a chelating group that is a radical of NODAGA.

62. The method of any one of clauses 35 to 52, or 56 to 61, or a pharmaceutically acceptable salt thereof, comprising a chelating group of the formula

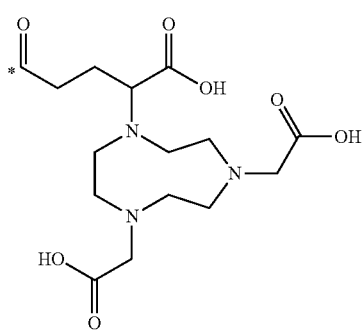 [SMILES: O=CCCC(C(=O)O)N1CCN(CC(=O)O)CCN(CC(=O)O)CC1]

wherein * represents a covalent bond to the rest of the conjugate.

63. The method of clauses 35, or a pharmaceutically acceptable salt thereof, comprising the formula

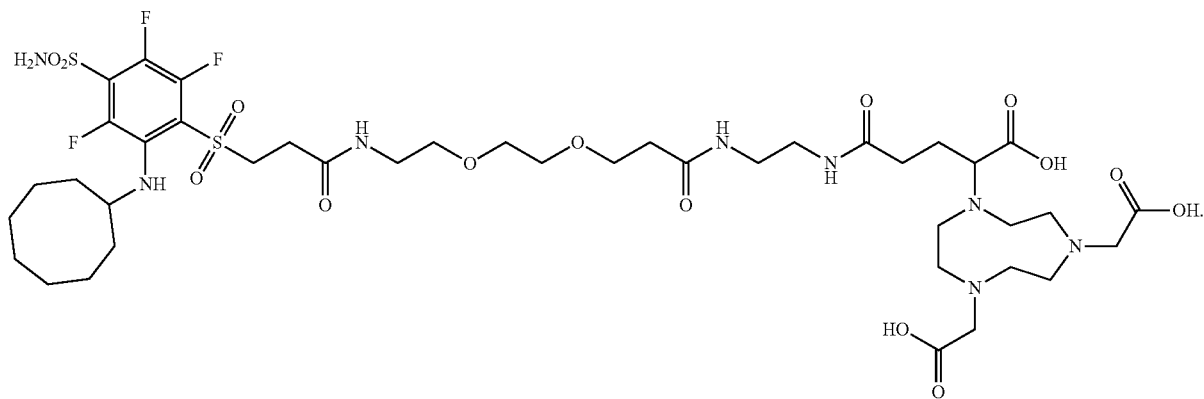 [SMILES: NS(=O)(=O)c1c(F)c(F)c(S(=O)(=O)CCC(=O)NCCOCCOCCC(=O)NCCNC(=O)CCC(C(=O)O)N2CCN(CC(=O)O)CCN(CC(=O)O)CC2)c(NC2CCCCCCC2)c1F]

64. A composition comprising a conjugate according to any one of clauses 1 to 34, or a pharmaceutically acceptable salt thereof, and optionally at least one pharmaceutically acceptable excipient.

65. A conjugate according to any one of clauses 1 to 29, for use in a method of imaging a population of cells in a subject.

66. The conjugate of clause 65, wherein the method comprises administering to the subject an amount of the conjugate effective for imaging the cells.

67. Use of a conjugate according to any one of clauses 1 to 29, in the preparation of a medicament useful for imaging a population of cells in a subject.

68. The use of clause 67, wherein the method comprises administering to the subject an amount of the conjugate effective for imaging the cells.

69. A method of treating cancer in a subject comprises administering to the subject a therapeutically effective amount of a conjugate of any one of clauses 1 to 17 or 30 to 34.

70. A conjugate according to any one of clauses 1 to 17 or 30 to 34 for use in a method of treating cancer in a subject.

71. Use of a conjugate according to any one of clauses 1 to 17 or 30 to 34, in the preparation of a medicament useful for treating cancer in a subject.

72. A method of imaging a population of cells in vitro, comprising a. contacting the cells with a conjugate of any one of clauses 1 to 29 to provide labelled cells, and b. visualizing the labelled cells with a fluorescent light source or a suitable detector.

BRIEF DESCRIPTION OF THE DRAWINGS

FIG. 23A, whole mouse. FIG. 23B, extracted.

DEFINITIONS

Figure 1A:
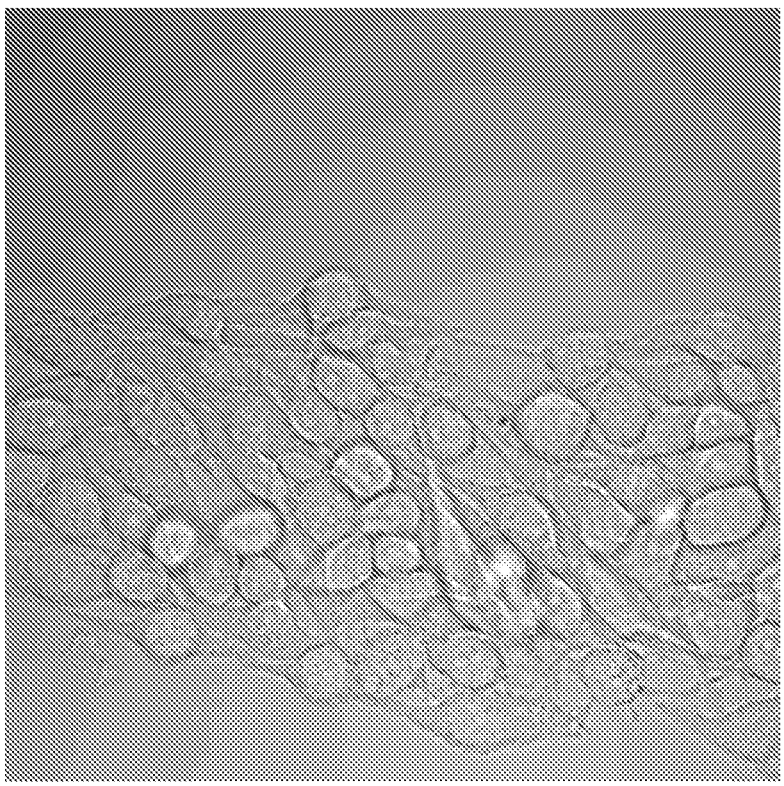
FIGS. 1A-F show images of cells where FIGS. 1A and B are white light and florescence confocal microscopy of 25 nM FBSA-PEG2-FITC conjugate, Conjugate 5; where FIGS. 1C and D show white light and florescence confocal microscopy of the competition control of 25 nM FITC conjugate 5 plus 100-fold excess CAIX inhibitor (Compound 3, 3-((2-(cyclooctylamino)-3,5,6-trifluoro-4-sulfamoylphenyl)sulfonyl)propanoic acid); where FIGS. 1E and F show white light and florescence confocal microscopy of SKRC52 cells only; and where the FITC conjugate 5 bound the cells and competed in the presence of excess unconjugated inhibitor, indicating a specific receptor-specific binding event.
Figure 1B:
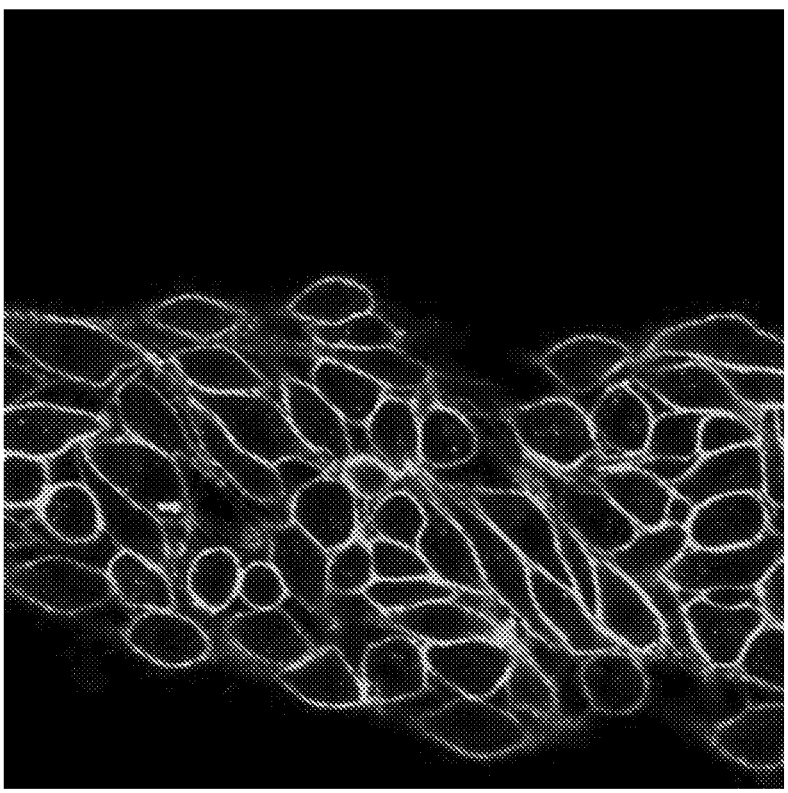
Figure 1C:
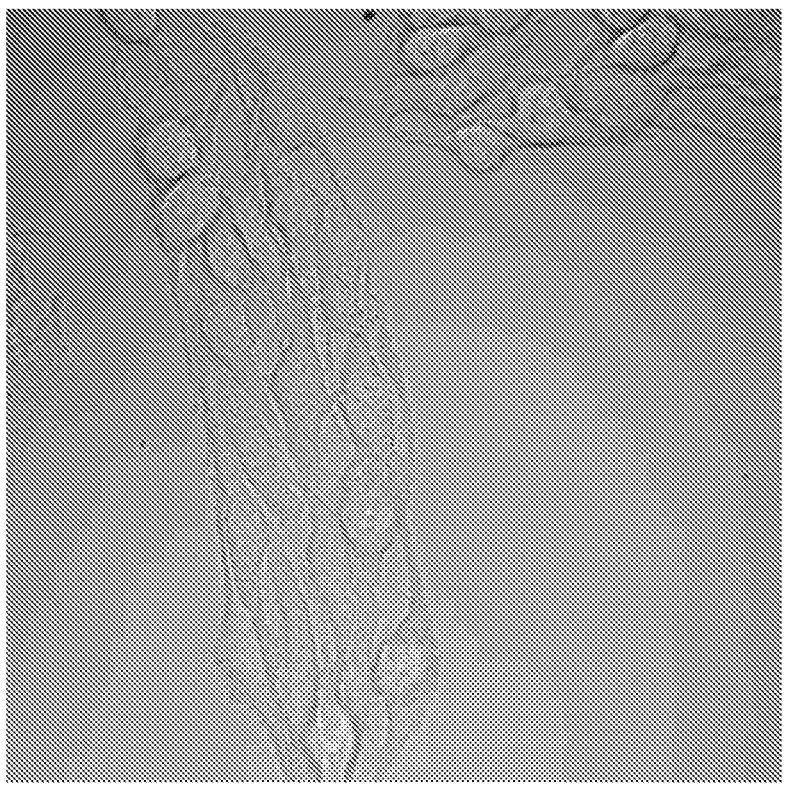
Figure 1D:
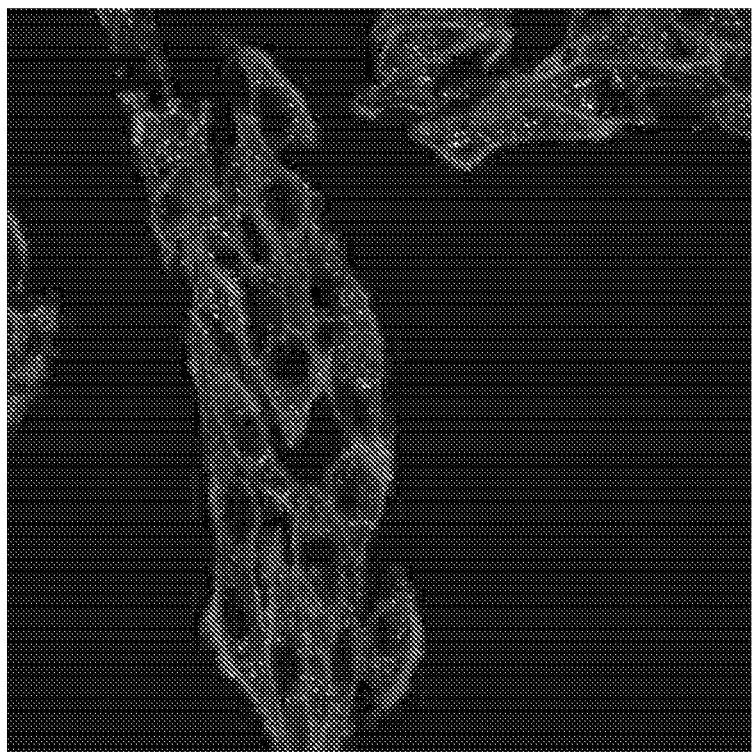
Figure 1E:
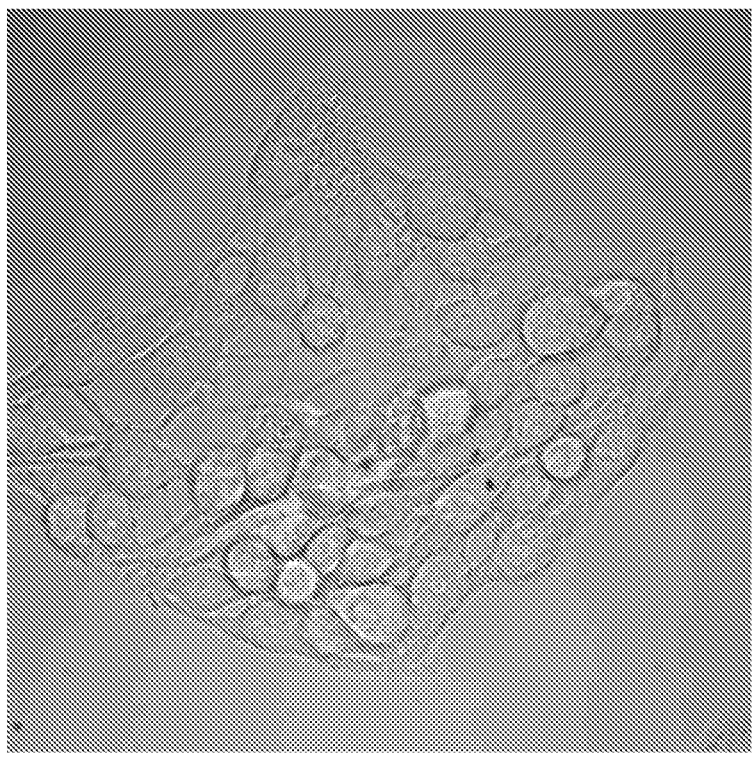
Figure 1F:
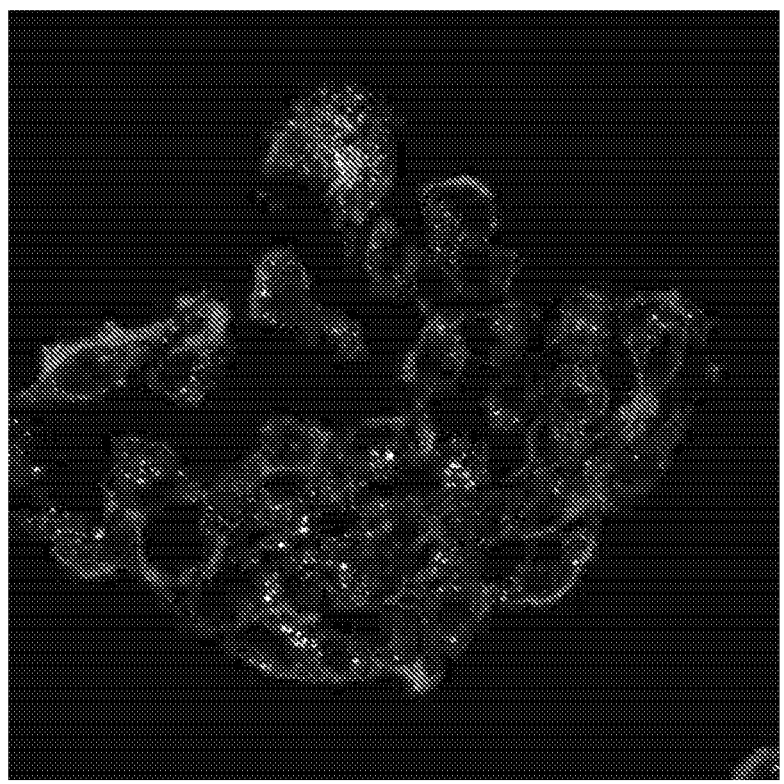
Figure 2:
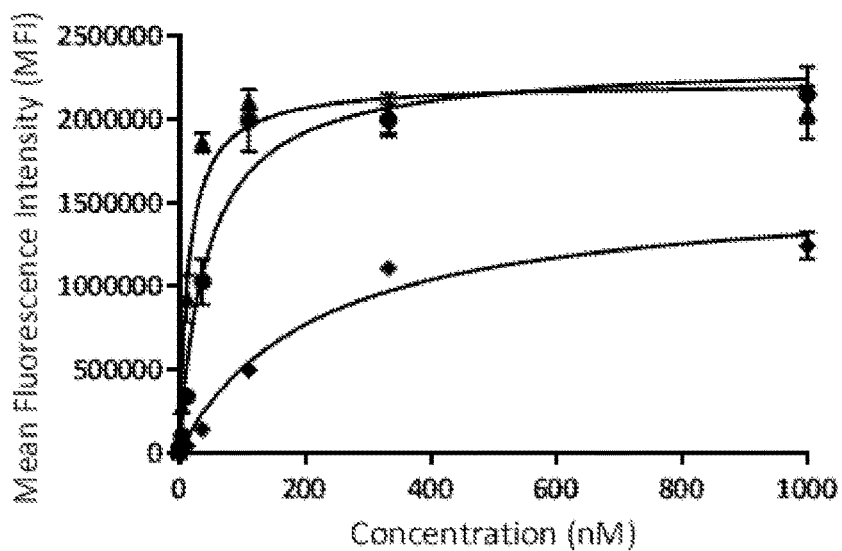
FIG. 2 shows the binding affinity of CAIX FITC conjugates 5, 7, and 9 in HEK293-CA9 Cells, and shows that the PEG2 linker has a binding affinity at 17.94 nM. (●) Conjugate 5, $K_D$=17.94 nM; (▲) Conjugate 7, $K_D$=55.2 nM; (♦) Conjugate 9, $K_D$=215.7 nM.
Figure 3:
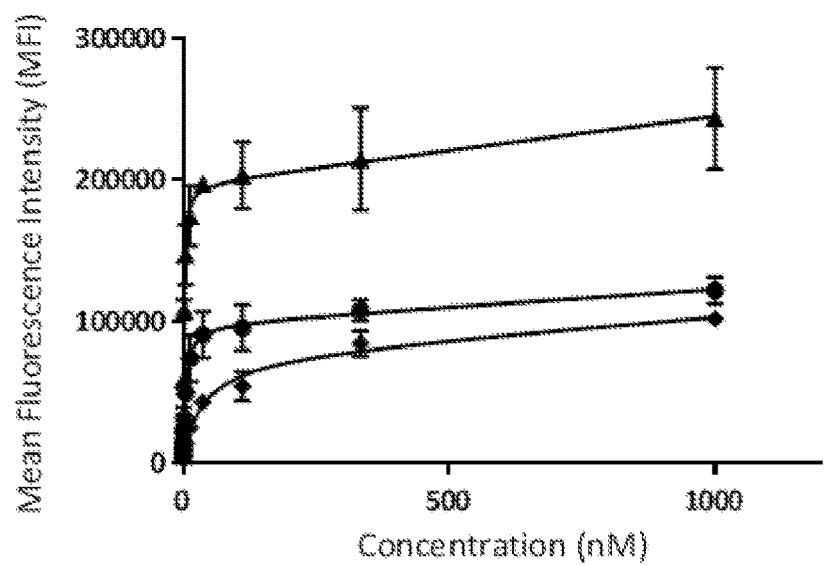
FIG. 3 shows the binding affinity of CAIX FITC conjugates 5, 7, and 9 in SKRC52 cells, and shows that the PEG$_2$ linker has binding affinity at 1.28 nM. (●) Conjugate 5, $K_D$=1.28 nM; (▲) Conjugate 7, $K_D$=4.57 nM; (♦) Conjugate 9, $K_D$=40.89 nM.
Figure 4:
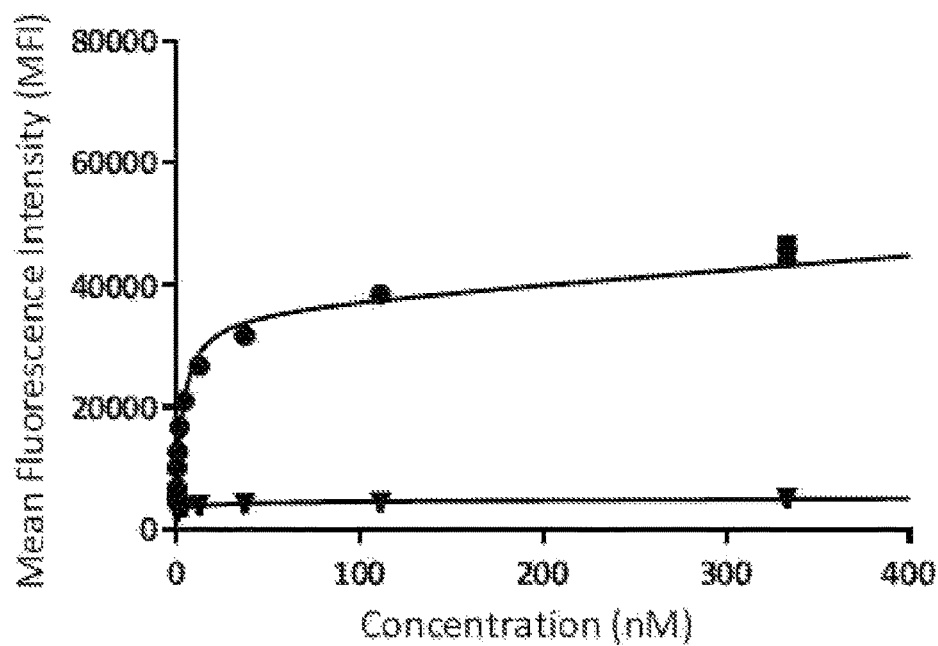
FIG. 4 shows the binding affinity of CAIX FITC conjugate 5 in HT-29 cells, showing that the conjugate bound the cells and competed in the presence of 100-fold excess unconjugated inhibitor, indicating a specific receptor-specific binding event. (▼) Competition; (●) Conjugate 5, $K_D$=4.553 nM.
Figure 5:
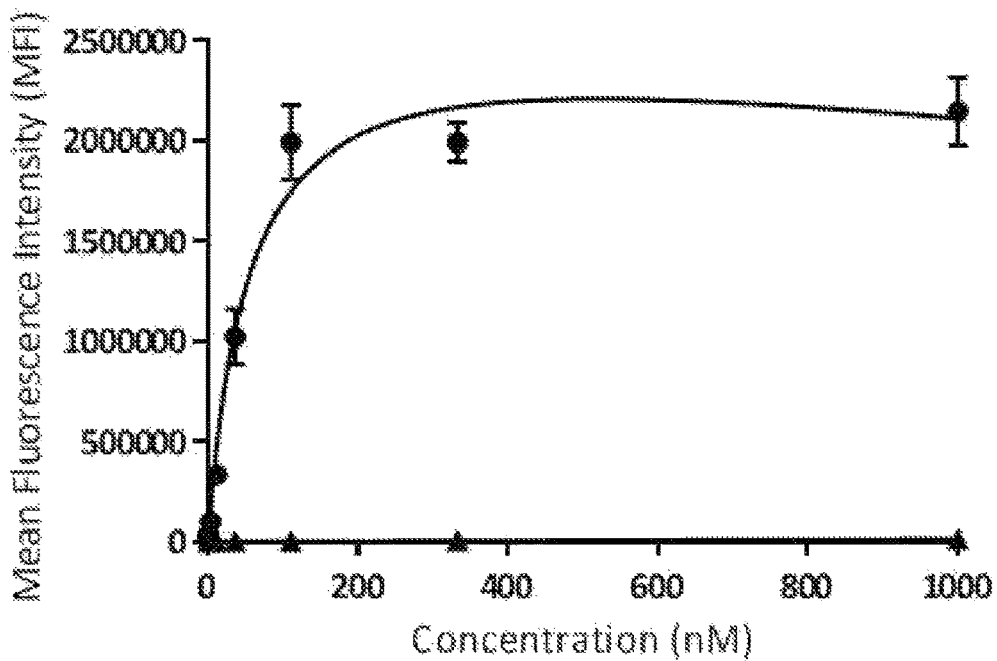
FIG. 5 shows the binding affinity of CAIX FITC conjugate 7 in HEK293-CA9 cells, showing that the conjugate bound the cells and competed in the presence of 100-fold excess unconjugated inhibitor, indicating a specific receptor-specific binding event. (▲) Competition; (●) Conjugate 7, $K_D$=55.2 nM.
Figure 6:
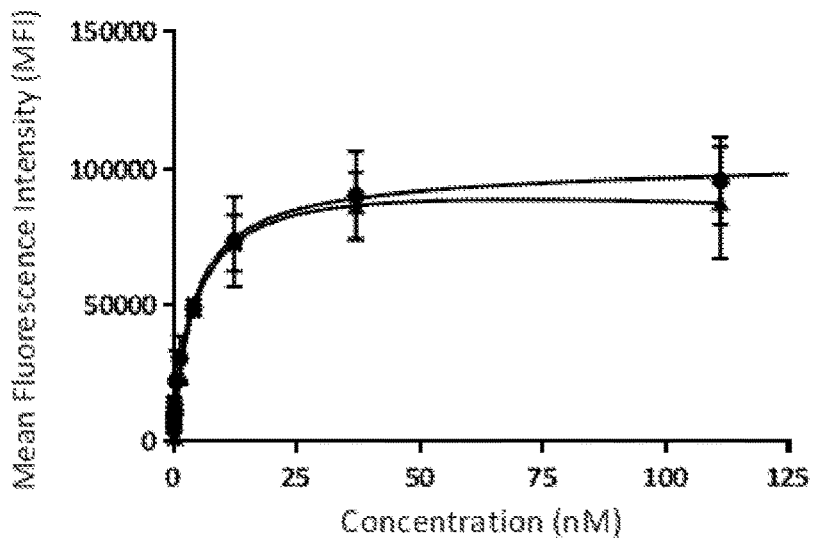
FIG. 6 shows the binding affinity of CAIX FITC conjugate 5 in SKRC52 cells with or without hypoxia showing that conjugate 5 binds to CAIX irrespective of whether or not hypoxia is present. (●) Normoxia SKRC52, 4.57 nM; (▲) Hypoxia SKRC52, $K_D$=4.72 nM.
Figure 7:
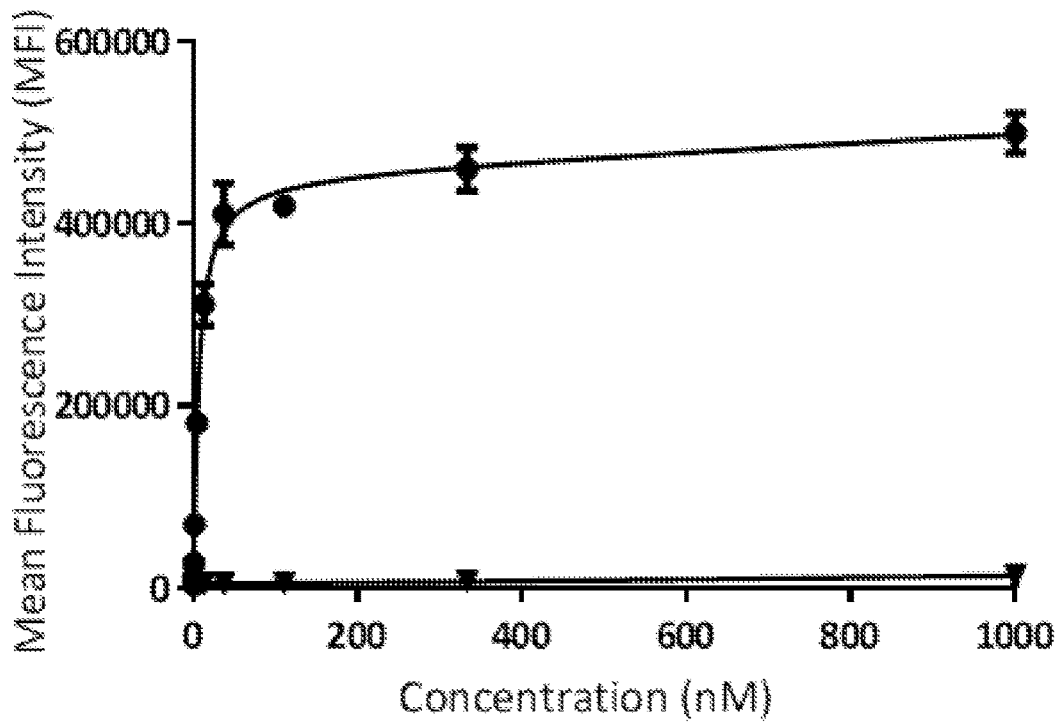
FIG. 7 shows the binding affinity of CAIX FITC conjugate 5 in A549 cells. (▼) Competition; (●) Conjugate 5, $K_D$=6.044 nM.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_6$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like.

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1,2,3,4-tetrahydropyridinyl, and the like.

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 9-membered heteroaryl, 3- to 7-membered heteroaryl, 5- to 7-membered heteroaryl, 5- to 9-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, indolyl, and carbazoloyl, and the like.

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "trihalomethyl" refers to a methyl group having three halo substituents, such as a trifluoromethyl group.

As used herein, "cyano" refers to a —CN group.

As used herein, "sulfinyl" refers to a —S(O)R" group, where R" is any R group as described in the various embodiments provided herein, or R" may be a hydroxyl group.

As used herein, "sulfonyl" refers to a —S(O)₂R" group, where R" is any R group as described in the various embodiments provided herein, or R" may be a hydroxyl group.

As used herein, "S-sulfonamido" refers to a —S(O)₂NR"R" group, where R" is any R group as described in the various embodiments provided herein.

As used herein, "N-sulfonamido" refers to a —NR"S(O)₂R" group, where R" is any R group as described in the various embodiments provided herein.

As used herein, "O-carbamyl" refers to a —OC(O)NR"R" group, where R" is any R group as described in the various embodiments provided herein.

As used herein, "N-carbamyl" refers to an R"OC(O)NR"— group, where R" is any R group as described in the various embodiments provided herein.

As used herein, "O-thiocarbamyl" refers to a —OC(S)NR"R" group, where R" is any R group as described in the various embodiments provided herein.

As used herein, "N-thiocarbamyl" refers to a R"OC(S)NR"— group, where R" is any R group as described in the various embodiments provided herein.

As used herein, "amino" refers to an —NR"R" group, where R" is any R group as described in the various embodiments provided herein.

As used herein, "C-amido" refers to a —C(O)NR"R" group, where R" is any R group as described in the various embodiments provided herein.

As used herein, "N-amido" refers to a R"C(O)NR"— group, where R" is any R group as described in the various embodiments provided herein.

As used herein, "nitro" refers to a NO₂ group.

As used herein, "bond" refers to a covalent bond.

As used herein, "optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, "amino acid" (a.k.a. "AA") means any molecule that includes an alpha-carbon atom covalently bonded to an amino group and an acid group. The acid group may include a carboxyl group. "Amino acid" may include molecules having one of the formulas:

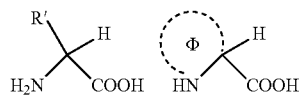

wherein R' is a side group and Φ includes at least 3 carbon atoms. "Amino acid" includes stereoisomers such as the D-amino acid and L-amino acid forms. Illustrative amino acid groups include, but are not limited to, the twenty endogenous human amino acids and their derivatives, such as lysine (Lys), asparagine (Asn), threonine (Thr), serine (Ser), isoleucine (Ile), methionine (Met), proline (Pro), histidine (His), glutamine (Gln), arginine (Arg), glycine (Gly), aspartic acid (Asp), glutamic acid (Glu), alanine (Ala), valine (Val), phenylalanine (Phe), leucine (Leu), tyrosine (Tyr), cysteine (Cys), tryptophan (Trp), phosphoserine (PSER), sulfo-cysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-amino-butyric acid (GABA), beta-amino-isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (I)), DL-allo-hydroxylysine (hydroxylysine (2)), ornithine (ORN), homocystine (HCY), and derivatives thereof. In connection with the embodiments described herein, amino acids can be covalently attached to other portions of the conjugates described herein through their alpha-amino and carboxy functional groups (i.e. in a peptide bond configuration), or through their side chain functional groups (such as the side chain carboxy group in glutamic acid) and either their alpha-amino or carboxy functional groups. It will be understood that amino acids, when used in connection with the conjugates described herein, may exist as zwitterions in a conjugate in which they are incorporated.

As used herein, "prodrug" refers to a compound that can be administered to a subject in a pharmacologically inactive form which then can be converted to a pharmacologically active form through a normal metabolic process, such as hydrolysis of an oxazolidine. It will be understood that the metabolic processes through which a prodrug can be converted to an active drug include, but are not limited to, one or more spontaneous chemical reaction(s), enzyme-catalyzed chemical reaction(s), and/or other metabolic chemical reaction(s), or a combination thereof. It will be appreciated that understood that a variety of metabolic processes are known in the art, and the metabolic processes through which the prodrugs described herein are converted to active drugs are non-limiting. A prodrug can be a precursor chemical compound of a drug that has a therapeutic effect on a subject.

As used herein, the term "therapeutically effective amount" refers to an amount of a drug or pharmaceutical agent that elicits the biological or medicinal response in a subject (i.e. a tissue system, animal or human) that is being sought by a researcher, veterinarian, medical doctor or other clinician, which includes, but is not limited to, alleviation of the symptoms of the disease or disorder being treated. In one aspect, the therapeutically effective amount is that amount of an active which may treat or alleviate the disease or symptoms of the disease at a reasonable benefit/risk ratio applicable to any medical treatment. In another aspect, the therapeutically effective amount is that amount of an inactive prodrug which when converted through normal metabolic processes to produce an amount of active drug capable of eliciting the biological or medicinal response in a subject that is being sought.

It is also appreciated that the dose, whether referring to monotherapy or combination therapy, is advantageously selected with reference to any toxicity, or other undesirable side effect, that might occur during administration of one or more of the conjugates described herein. Further, it is appreciated that the co-therapies described herein may allow for the administration of lower doses of conjugates that show such toxicity, or other undesirable side effect, where those lower doses are below thresholds of toxicity or lower in the therapeutic window than would otherwise be administered in the absence of a cotherapy.

As used herein, "administering" includes all means of introducing the conjugates and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The conjugates and compositions described herein may be administered in unit dosage forms and/or formulations containing conventional nontoxic pharmaceutically-acceptable carriers, adjuvants, and/or vehicles.

As used herein "pharmaceutical composition" or "composition" refers to a mixture of one or more of the conjugates described herein, or pharmaceutically acceptable salts, solvates, hydrates thereof, with other chemical components, such as pharmaceutically acceptable excipients. The purpose of a pharmaceutical composition is to facilitate administration of a conjugate to a subject. Pharmaceutical compositions suitable for the delivery of conjugates described and methods for their preparation will be readily apparent to those skilled in the art. Such compositions and methods for their preparation may be found, for example, in 'Remington's Pharmaceutical Sciences', 19th Edition (Mack Publishing Company, 1995).

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

DETAILED DESCRIPTION

In accordance with Applicants' disclosure described herein, the embodiments of the numbered clauses provided in the summary above, or any combination thereof, are contemplated for combination with any of the embodiments described in the Detailed Description section of this patent application.

In each of the foregoing and each of the following embodiments, it is to be understood that the formulae include and represent not only all pharmaceutically acceptable salts of the conjugates, but also include any and all hydrates and/or solvates of the conjugate formulae. It is appreciated that certain functional groups, such as the hydroxy, amino, and like groups form complexes and/or coordination conjugates with water and/or various solvents, in the various physical forms of the conjugates. Accordingly, the above formulae are to be understood to include and represent those various hydrates and/or solvates. It is also to be understood that the non-hydrates and/or non-solvates of the conjugate formulae are described by such formula, as well as the hydrates and/or solvates of the conjugate formulae.

In some embodiments, the disclosure provides a conjugate of the formula B-L-A, wherein B is a binding ligand of carbonic anhydrase IX, L is an optional linker, and A is a therapeutic agent and an imaging agent.

It will be appreciated that CA IX ligands useful in connection with the present disclosure are not particularly limited by structure. Useful CA IX inhibitors can be any drug or compound that shows binding affinity for CA IX, such as a CA IX inhibitor, CA IX agonist, or CA IX antagonist. In some aspects of these embodiments, the CA IX ligand is an aryl sulfonamide containing compound. In some aspects of these embodiments, the CA IX ligand is of the formula

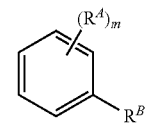

wherein
each $R^A$ is independently selected from the group consisting of H, halogen, —$OR^1$, —$OC(O)R^1$, —$OC(O)NR^1R^2$, —$OS(O)R^1$, —$OS(O)_2R^1$, —$SR^1$, —$S(O)R^1$, —$S(O)_2R^1$, —$S(O)NR^1R^2$, —$S(O)_2NR^1R^2$, —$OS(O)NR^1R^2$, —$OS(O)_2NR^1R^2$, —$NR^1R^2$, —$NR^1C(O)R^1$, —$NR^1C(O)OR^2$, —$NR^1C(O)NR^1R^2$, —$NR^1S(O)R^2$, —$NR^1S(O)_2R^2$, —$NR^1S(O)NR^1R^2$, —$NR^1S(O)_2NR^1R^2$, —$C(O)R^1$, —$C(O)OR^1$, and —$C(O)NR^1R^2$;

$R^B$ is —$OR^3$, —$SR^3$, —$NR^3R^4$, —$S(O)_2R^3$, —$NR^4C(O)R^3$ or $NR^4C(O)NR^3R^4$;

$R^3$ is independently $C_1$-$C_{10}$ alkyl, $C_2$-$C_{10}$ alkenyl or phenyl, each independently substituted with one substituent selected from the group consisting of —$NR^5$—*, —$NR^5(CH_2)_{m2}N(R^6)$—*, —$OC(O)$—*, —$OC(O)N(R^5)$—*, —$C(O)$—*, —$C(O)O$—*, and —$C(O)N(R^5)$—*;

each $R^1$, $R^2$, $R^4$, $R^5$ and $R^6$ is independently selected from the group consisting of H, $C_1$-$C_6$ alkyl, $C_2$-$C_6$ alkenyl, $C_2$-$C_6$ alkynyl, and $C_3$-$C_9$ cycloalkyl;

L is an optional linker,
A is a therapeutic agent or an imaging agent;
m is an integer from 1 to 5; and
* represents a point of attachment to the rest of the conjugate.

In some embodiments, each $R^A$ is selected from the group consisting of halogen, —$S(O)_2NR^1R^2$, and —$NR^1R^2$. In some embodiments, one $R^A$ is —$S(O)_2NR^1R^2$. In some embodiments, one $R^A$ is —$S(O)_2NR^1R^2$, wherein $R^1$ and $R^2$ are H. In some embodiments, one $R^A$ is —$NR^1R^2$. In some embodiments, one $R^A$ is —$NR^1R^2$, wherein $R^1$ is H, and $R^2$ is $C_3$-$C_9$ cycloalkyl. In some embodiments, one $R^A$ is —$NR^1R^2$, wherein $R^1$ is H, and $R^2$ is $C_3$-$C_9$ cyclooctyl. In some embodiments, one $R^A$ is —$S(O)_2NR^1R^2$, and one $R^A$ is —$NR^1R^2$. In some embodiments, one $R^A$ is —$S(O)_2NR^1R^2$ wherein $R^1$ and $R^2$ are H, and one $R^A$ is —$NR^1R^2$ wherein $R^1$ is H, and $R^2$ is $C_3$-$C_9$ cycloalkyl. In some embodiments, one $R^A$ is —$S(O)_2NR^1R^2$ wherein $R^1$ and $R^2$ are H, and one $R^A$ is —$NR^1R^2$ wherein $R^1$ is H, and $R^2$ is cyclooctyl. In some embodiments, the CA IX ligand is of the formula

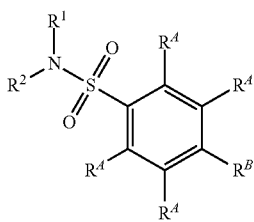

wherein each $R^A$, $R^B$, $R^1$ and $R^2$ are as defined herein. In some embodiments, $R^1$ and $R^2$ are H.

In some embodiments, the CA IX ligand is of the formula

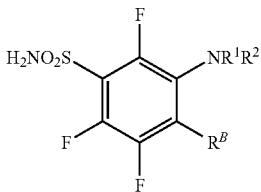

wherein $R^B$, $R^1$ and $R^2$ are as defined herein. In some embodiments, $R^1$ is H, and $R^2$ is cyclooctyl.

In some embodiments, $R^B$ is —S(O)$_2$R$^3$. In some embodiments, $R^B$ is —S(O)$_2$R$^3$, and one $R^A$ is —S(O)$_2$NR$^1$R$^2$. In some embodiments, $R^B$ is —S(O)$_2$R$^3$, one $R^A$ is —S(O)$_2$NR$^1$R$^2$, and one $R^A$ is —NR$^1$R$^2$. In some embodiments, $R^B$ is —S(O)$_2$R$^3$, one $R^A$ is —S(O)$_2$NR$^1$R$^2$R$^1$ wherein $R^1$ and $R^2$ are H, and one $R^A$ is —NR$^1$R$^2$ wherein $R^1$ is H, and $R^2$ is C$_3$-C$_9$ cycloalkyl. In some embodiments, the CA IX ligand is of the formula

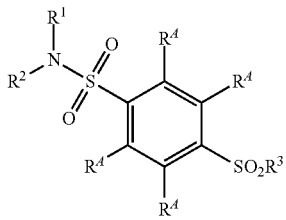

wherein each $R^A$, $R^1$, $R^2$ and $R^3$ are as defined herein.

In some embodiments, the CA IX ligand is of the formula

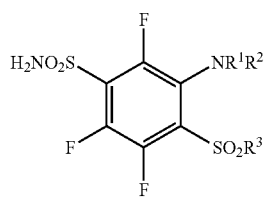

wherein $R^1$, $R^2$ and $R^3$ are as defined herein. In some embodiments, the CA IX ligand is of the formula

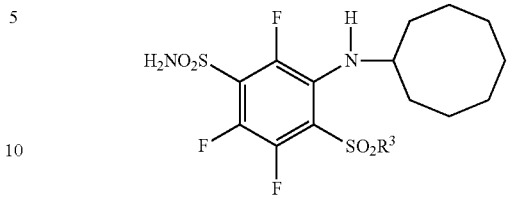

wherein $R^3$ is as defined herein.

In some embodiments, $R^3$ is independently C$_1$-C$_{10}$ alkyl, C$_2$-C$_{10}$ alkenyl or phenyl, each independently substituted with one substituent selected from the group consisting of —NR$^5$—*, —NR$^5$(CH$_2$)$_{m2}$N(R$^6$)—*, —OC(O)—*, —OC(O)N(R$^5$)—*, —C(O)—*, —C(O)O—*, and —C(O)N(R$^5$)—*; and each remaining hydrogen atom in C$_1$-C$_{10}$ alkyl, C$_2$-C$_{10}$ alkenyl or phenyl is independently optionally substituted by C$_1$-C$_{10}$ alkyl, C$_2$-C$_{10}$ alkenyl, halogen, —OR$^1$, —OC(O)R$^1$, —OC(O)NR$^1$R$^2$, —OS(O)R$^1$, —OS(O)$_2$R$^1$, —SR$^1$, —S(O)R$^1$, —S(O)$_2$R$^1$, —S(O)NR$^1$R$^2$, —S(O)$_2$NR$^1$R$^2$, —OS(O)NR$^1$R$^2$, —OS(O)$_2$NR$^1$R$^2$, —NR$^1$R$^2$, —NR$^1$C(O)R$^1$, —NR$^1$C(O)OR$^2$, —NR$^1$C(O)NR$^1$R$^2$, —NR$^1$S(O)R$^2$, —NR$^1$S(O)$_2$R$^2$, —NR$^1$S(O)NR$^1$R$^2$, —NR$^1$S(O)$_2$NR$^1$R$^2$, —C(O)R$^1$, —C(O)OR$^1$, and —C(O)NR$^1$R$^2$. In some embodiments, $R^3$ is C$_1$-C$_{10}$ alkyl substituted with one substituent selected from the group consisting of —C(O)N(R$^5$)—* and —C(O)—*, wherein $R^5$ is as defined herein, and * represents a point of attachment to the rest of the conjugate.

It will be appreciated that linkers useful in connection with the present disclosure are not particularly limited by structure. The linker can be any linker of from about 2 to about 100 atoms in length and composed of elements including C, N, O and S that covalently attaches a CA IX ligand to an agent. In some embodiments, the linker can be any linker of from 10 to 75 atoms in length along the linker chain of atoms. In some embodiments, the linker can be any linker of from 15 to 60 atoms in length along the linker chain of atoms. It will be appreciated that the ranges provided herein for linker length in term of atom number in the chain can include any boundary numbers between and including 2 and 100, such as 5, 10, 15, 20, 25, 35, 45, 60, 75, 80, and 100. In some embodiments, the linker can be any linker of from 5 Å to about 100 Å in length. In some embodiments, the linker can be any linker of from 5 Å to about 50 Å in length. In some embodiments, the linker can be any linker of from 5 Å to about 40 Å in length. In some embodiments, the linker can be any linker of from 15 Å to about 25 Å in length. It will be appreciated that the ranges provided herein for linker length can include any boundary numbers between and including 5 and 100.

In some embodiments, the linker comprises a releasable linker where the term "releasable linker" refers to a linker that includes at least one bond that can be broken under physiological conditions, such as a pH-labile, acid-labile, base-labile, oxidatively labile, metabolically labile, biochemically labile, or enzyme-labile bond. It is appreciated that such physiological conditions resulting in bond breaking do not necessarily include a biological or metabolic process, and instead may include a standard chemical reaction, such as a hydrolysis reaction, for example, at physiological pH, or as a result of compartmentalization into a cellular organelle such as an endosome having a lower pH than cytosolic pH. In some embodiments, the releasable linker comprises a disulfide bond. In some embodiments, the linker comprises a disulfide linker portion. In some embodiments, the linker comprises a hydrazine linker portion. In some embodiments, the releasable linker comprises a portion having the formula

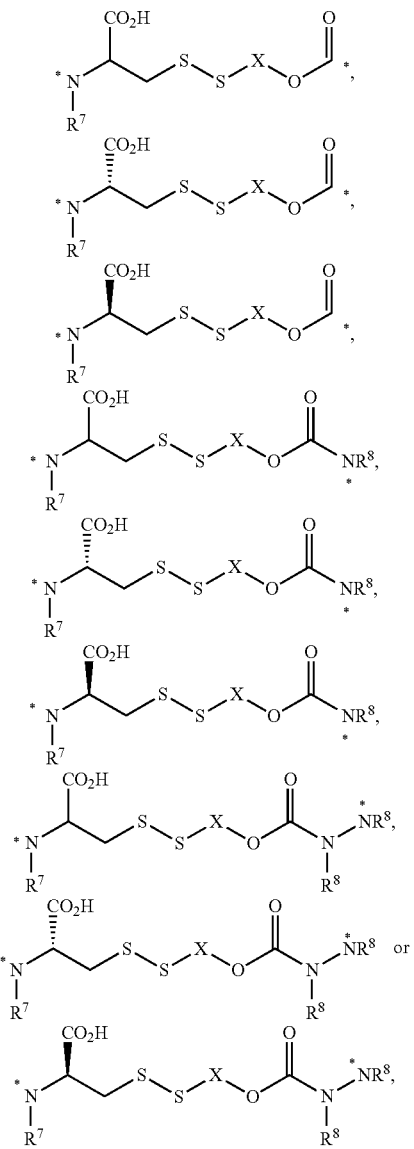

wherein each $R^7$ and $R^8$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$OC(O)NR^9R^{10}$, —$OS(O)R^9$, —$OS(O)_2R^9$, —$SR^9$, —$S(O)R^9$, —$S(O)_2R^9$, —$S(O)NR^9R^{10}$, —$S(O)_2NR^9R^{10}$, —$OS(O)NR^9R^{10}$, —$OS(O)_2NR^9R^{10}$, —$NR^9R^{10}$, —$NR^9C(O)R^{10}$, —$NR^9C(O)OR^{10}$, —$NR^9C(O)NR^{11}R^{12}$, —$NR^9S(O)R^{10}$, —$NR^9S(O)_2R^{10}$, —$NR^9S(O)NR^{11}R^{12}$, —$NR^9S(O)_2NR^{11}R^{12}$, —$C(O)R^9$, —$C(O)OR^9$ or —$C(O)NR^9R^{10}$;

each X is independently $C_1$-$C_6$ alkyl or $C_6$-$C_{10}$ aryl-($C_1$-$C_6$ alkyl), wherein each hydrogen atom in $C_1$-$C_6$ alkyl and $C_6$-$C_{10}$ aryl-($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$OC(O)NR^9R^{10}$, —$OS(O)R^9$, —$OS(O)_2R^9$, —$SR^9$, —$S(O)R^9$, —$S(O)_2R^9$, —$S(O)NR^9R^{10}$, —$S(O)_2NR^9R^{10}$, —$OS(O)NR^9R^{10}$, —$OS(O)_2NR^9R^{10}$, —$NR^9R^{10}$, —$NR^9C(O)R^{10}$, —$NR^9C(O)OR^{10}$, —$NR^9C(O)NR^{11}R^{12}$, —$NR^9S(O)R^{10}$, —$NR^9S(O)_2R^{10}$, —$NR^9S(O)NR^{11}R^{12}$, —$NR^9S(O)_2NR^{11}R^{12}$, —$C(O)R^9$, —$C(O)OR^9$ or —$C(O)NR^9R^{10}$;

each $R^9$, $R^{10}$, $R^{11}$ and $R^{12}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and each * represents a covalent bond to the rest of the conjugate. In some embodiments, each $R^7$ and $R^8$ is H. In some embodiments, X is $C_1$-$C_6$ alkyl.

In some embodiments, the linker comprises a portion of the formula

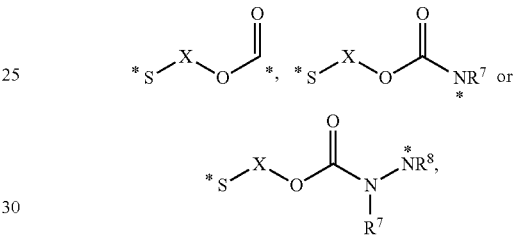

wherein $R^7$ and $R^8$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$OC(O)NR^9R^{10}$, —$OS(O)R^9$, —$OS(O)_2R^9$, —$SR^9$, —$S(O)R^9$, —$S(O)_2R^9$, —$S(O)NR^9R^{10}$, —$S(O)_2NR^9R^{10}$, —$OS(O)NR^9R^{10}$, —$OS(O)_2NR^9R^{10}$, —$NR^9R^{10}$, —$NR^9C(O)R^{10}$, —$NR^9C(O)OR^{10}$, —$NR^9C(O)NR^{11}R^{12}$, —$NR^9S(O)R^{10}$, —$NR^9S(O)_2R^{10}$, —$NR^9S(O)NR^{11}R^{12}$, —$NR^9S(O)_2NR^{11}R^{12}$, —$C(O)R^9$, —$C(O)OR^9$ or —$C(O)NR^9R^{10}$;

each X is independently $C_1$-$C_6$ alkyl or $C_6$-$C_{10}$ aryl-($C_1$-$C_6$ alkyl), wherein each hydrogen atom in $C_1$-$C_6$ alkyl and $C_6$-$C_{10}$ aryl-($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$OC(O)NR^9R^{10}$, —$OS(O)R^9$, —$OS(O)_2R^9$, —$SR^9$, —$S(O)R^9$, —$S(O)_2R^9$, —$S(O)NR^9R^{10}$, —$S(O)_2NR^9R^{10}$, —$OS(O)NR^9R^{10}$, —$OS(O)_2NR^9R^{10}$, —$NR^9R^{10}$, —$NR^9C(O)R^{10}$, —$NR^9C(O)OR^{10}$, —$NR^9C(O)NR^{11}R^{12}$, —$NR^9S(O)R^{10}$, —$NR^9S(O)_2R^{10}$, —$NR^9S(O)NR^{11}R^{12}$, —$NR^9S(O)_2NR^{11}R^{12}$, —$C(O)R^9$, —$C(O)OR^9$ or —$C(O)NR^9R^{10}$;

each $R^9$, $R^{10}$, $R^{11}$ and $R^{12}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and each * represents a covalent bond to the rest of the conjugate. In some embodiments, each $R^7$ and $R^8$ is H. In some embodiments, X is $C_1$-$C_6$ alkyl.

In some embodiments, the linker can include one or more spacer linker portions. It will be appreciated that the structure of spacer linker portions included in the conjugates of the present disclosure are not particularly limited in structure. In some embodiments, the linker comprises simple groups, such as alkyl chain portions, ether portions (e.g. PEG), long chain amine portions, amino acid chain portions, a hydrazine portion, and the like, and combinations thereof. In some embodiments, linkers useful in connection with the present disclosure comprise at least one portion selected from the group consisting of —C(O)(C$_1$-C$_{12}$ alkyl)C(O)—, —NH—C$_1$-C$_{12}$ alkyl-NH—, —N(C$_1$-C$_6$ alkyl)-C$_1$-C$_{12}$ alkyl-N(C$_1$-C$_6$ alkyl)-, —C(O)CH$_2$CH$_2$(OCH$_2$CH$_2$)$_q$NH—, —C(O)CH$_2$CH$_2$(OCH$_2$CH$_2$)$_q$N(C$_1$-C$_6$ alkyl)-, —(CH$_2$CH$_2$O)$_q$CH$_2$CH$_2$C(O)—, —NH(CH$_2$CH$_2$O)$_q$CH$_2$CH$_2$C(O)—, and —N(C$_1$-C$_6$ alkyl)(CH$_2$CH$_2$O)$_q$CH$_2$CH$_2$C(O)—; wherein q is an integer from 1 to 40. In some embodiments, q is 2. In some embodiments, q is 4. In some embodiments, q is 6. In some embodiments, q is 20. It will be appreciated that the value of q is not particularly limited, and can be any value between 1 and about 40. In some embodiments, the linker can comprise a chain of amino acids. In some embodiments, the linker can comprise a dipeptide, tripeptide, tetrapeptide, pentapeptide or hexpeptide. In some embodiments, the linker can comprise naturally occurring amino acids. In some embodiments, the linker can comprise unnatural amino acids. In some embodiments, the linker comprises at least one amino acid selected from the group consisting of 3-aminoalanine, aspartic acid, cysteine, and arginine. In some embodiments, the linker comprises a portion having the amino acid sequence 3-amino-alanine-Asp-Cys. In some embodiments, the linker comprises a portion having the amino acid sequence Asp-Arg-Asp-3-amino-alanine-Asp-Cys.

In some embodiments, the linker comprises a portion of conjugate comprises a portion having the formula

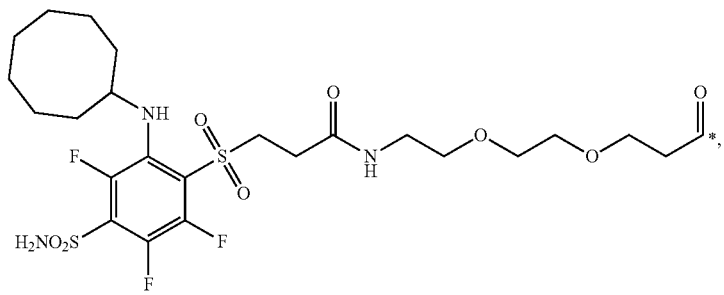

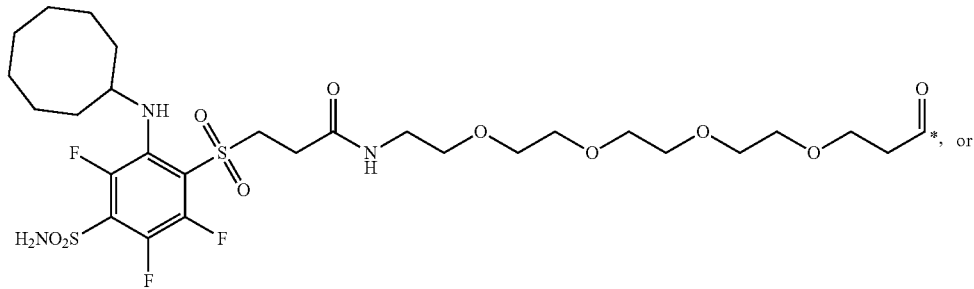

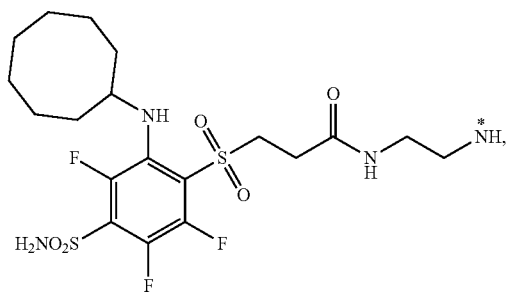

wherein * represents a covalent bond to the rest of the conjugate.

The agent used in connection with any of the conjugates described herein can be any molecule capable of modulating or otherwise modifying cell function, including pharmaceutically active compounds (e.g. a therapeutic agent), or any molecule capable of providing a measurable signal for imaging or visualized cells or tissues (e.g. an imaging agent).

Suitable molecules useful as therapeutic agents include, but are not limited to peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; cytotoxic agent, such as microtubule inhibitors; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives.

In some embodiments, the therapeutic agent can be a tubulysin. Natural tubulysins are generally linear tetrapeptides consisting of N-methyl pipecolic acid (Mep), isoleucine (Ile), an unnatural aminoacid called tubuvaline (Tuv), and either an unnatural aminoacid called tubutyrosine (Tut, an analog of tyrosine) or an unnatural aminoacid called tubuphenylalanine (Tup, an analog of phenylalanine).

In some embodiments, the therapeutic agent is a tetrapeptide of the formula

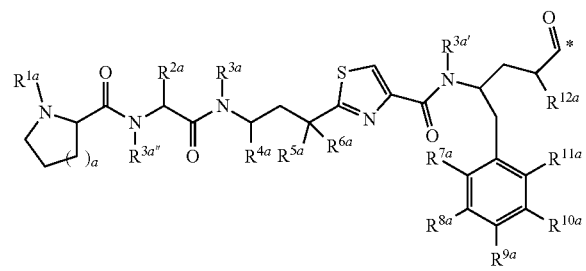

wherein $R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13a}$, —OC(O)$R^{13a}$, —OC(O)N$R^{13a}R^{13a'}$, —OS(O)$R^{13a}$, —OS(O)$_2$$R^{13a}$, —S$R^{13a}$, —SC(O)$R^{13a}$, —S(O)$R^{13a}$, —S(O)$_2$$R^{13a}$, —S(O)$_2$O$R^{13a}$, —S(O)N$R^{13a}R^{13a'}$, —S(O)$_2$N$R^{13a}R^{13a'}$, —OS(O)N$R^{13a}R^{13a'}$, —OS(O)$_2$N$R^{13a}R^{13a'}$, —N$R^{13a}R^{13a'}$, —N$R^{13a}$C(O)$R^{14a}$, —N$R^{13a}$C(O)O$R^{14a}$, —N$R^{13a}$C(O) N$R^{14a}R^{14a'}$, —N$R^{13a}$S(O)$R^{14a}$, —N$R^{13a}$S(O)$_2$$R^{14a}$, —N$R^{13a}$S(O)N$R^{13a}R^{14a'}$; N$R^{13a}$S(O)$_2$N$R^{14a}R^{14a'}$, —P(O)(O$R^{13a}$)$_2$, —C(O)$R^{13a}$, —C(O)O$R^{13a}$ or —C(O)N$R^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ and $R^{6a}$ are each independently selected from the group consisting of H, halogen, $C_1$-$C_6$ alkyl, $C_2$-$C_6$ alkenyl, $C_2$-$C_6$ alkynyl, —$OR^{15a}$, —$SR^{15a}$ and —N$R^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, —$OR^{16a}$, —$SR^{16a}$, —N$R^{16a}R^{16a'}$, —C(O)$R^{16a}$, —C(O)O$R^{16a}$ or —C(O)N$R^{16a}R^{16a'}$; or $R^{5a}$ and $R^{6a}$ taken together with the carbon atom to which they are attached form a —C(O)—;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, —CN, —NO$_2$, —NCO, —$OR^{17a}$, —$SR^{17a}$, —S(O)$_2$O$R^{17a}$, —N$R^{17a}R^{17a'}$, —P(O) (O$R^{17a}$)$_2$, —C(O)$R^{17a}$, —C(O)O$R^{17a}$ and —C(O) N$R^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, —$OR^{18a}$, —$SR^{18a}$, —N$R^{18a}R^{18a'}$, —C(O)$R^{18a}$, —C(O)O$R^{18a}$ or —C(O)N$R^{18a}R^{18a'}$;

each $R^{13a}$, $R^{13a'}$; $R^{14a}$, $R^{14a'}$; $R^{15a}$; $R^{15a'}$; $R^{16a}$; $R^{16a'}$; $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —NH$_2$ or —CO$_2$H;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —C(O)$R^{19a}$, —P(O)(O$R^{19a}$)$_2$, and —S(O)$_2$O$R^{19a}$, each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

a is 1, 2 or 3; and

* represents a covalent bond to the rest of the conjugate.

In some embodiments, the therapeutic agent is of the formula

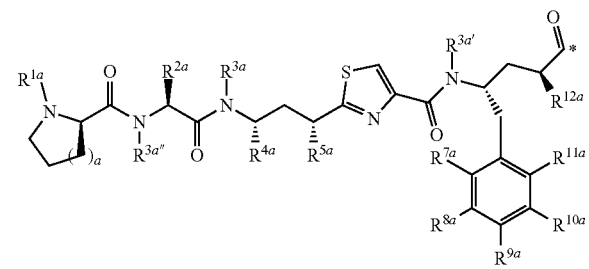

wherein $R^{1a}$, $R^{2a}$, $R^{3a}$, $R^{3a'}$, $R^{3a''}$, $R^{4a}$, $R^{5a}$, $R^{7a}$, $R^{8a}$, $R^{9a}$, $R^{10a}$, $R^{11a}$ and $R^{12a}$ are as described herein, and * represents a covalent bond to the rest of the conjugate.

In another embodiment, the therapeutic agent can be a naturally occurring tubulysin, or analog or derivative thereof, of the following general formula

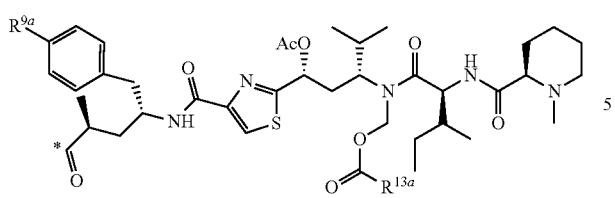

wherein $R^{9a}$ and $R^{13a}$ are as described herein, and * represents a covalent bond to the rest of the conjugate.

Conjugates of each of the foregoing tubulysins are described herein.

In some embodiments, the therapeutic agent can be a naturally occurring tubulysin of the following general formula

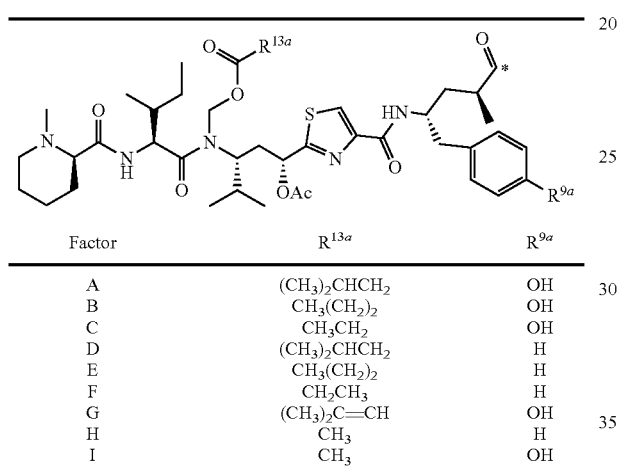

| Factor | $R^{13a}$ | $R^{9a}$ |
|---|---|---|
| A | $(CH_3)_2CHCH_2$ | OH |
| B | $CH_3(CH_2)_2$ | OH |
| C | $CH_3CH_2$ | OH |
| D | $(CH_3)_2CHCH_2$ | H |
| E | $CH_3(CH_2)_2$ | H |
| F | $CH_2CH_3$ | H |
| G | $(CH_3)_2C=CH$ | OH |
| H | $CH_3$ | H |
| I | $CH_3$ | OH | and * represents a covalent bond to the rest of the conjugate.

In some embodiments, the therapeutic agent is a maytansinoids, including maytansinol and maytansinol analogs. Maytansinoids are compounds that inhibit microtubule formation and are highly toxic to mammalian cells. Examples of suitable maytansinol analogues include those having a modified aromatic ring and those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

Examples of maytansinol analogs having a modified aromatic ring include, but are not limited to, C-19-dechloro (U.S. Pat. No. 4,256,746), C-20-hydroxy (or C-20-demethyl)+/−C-19-dechloro (U.S. Pat. Nos. 4,361,650 and 4,307,016), and C-20-demethoxy, C-20-acyloxy (—OCOR), +/−dechloro (U.S. Pat. No. 4,294,757).

Examples of maytansinol analogs having modifications of positions other than an aromatic ring include, but are not limited to, C-9-SH (U.S. Pat. No. 4,424,219), C-14-alkoxymethyl (demethoxy/$CH_2OR$) (U.S. Pat. No. 4,331,598), C-14-hydroxymethyl or acyloxymethyl ($CH_2OH$ or $CH_2OAc$) (U.S. Pat. No. 4,450,254), C-15-hydroxy/acyloxy (U.S. Pat. No. 4,364,866), C-15-methoxy (U.S. Pat. Nos. 4,313,946 and 4,315,929), C-18-N-demethyl (U.S. Pat. Nos. 4,362,663 and 4,322,348), and 4,5-deoxy (U.S. Pat. No. 4,371,533).

In some embodiments, the conjugate comprises thiol containing maytansinoid DM1, also known as $N^{2'}$-deacetyl-$N^{2'}$-(3-mercapto-1-oxopropyl)-maytansine, as the cytotoxic agent. The structure of DM1 is represented by formula (I):

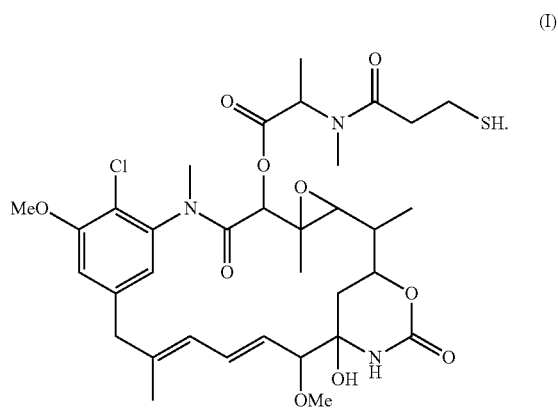 [SMILES: COc1cc2cc(c1Cl)N(C)C(=O)C(OC(=O)C(C)N(C)C(=O)CCS)C1(C)OC1C(C)C1CC(O)(NC(=O)O1)C(OC)/C=C/C=C(\C)C2]

In some embodiments, the conjugate comprises thiolcontaining maytansinoid DM4, also known as $N^{2'}$-deacetyl-$N^{2'}$-(4-methyl-4-mercapto-1-oxopentyl)-maytansine, as the cytotoxic agent. The structure of DM4 is represented by formula (II):

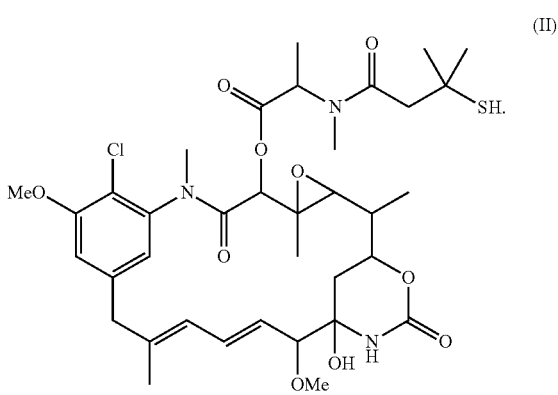 [SMILES: COc1cc2cc(c1Cl)N(C)C(=O)C(OC(=O)C(C)N(C)C(=O)CC(C)(C)S)C1(C)OC1C(C)C1CC(O)(NC(=O)O1)C(OC)/C=C/C=C(\C)C2]

Other maytansines may be used in connection with the present disclosure, such as, thiol and disulfide-containing maytansinoids bearing a mono or di-alkyl substitution on the carbon atom bearing the sulfur atom. Particularly preferred is a maytansinoid having at the C-3 position (a) C-14 hydroxymethyl, C-15 hydroxy, or C-20 desmethyl functionality, and (b) an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocycloalkyl radical, and further wherein one of the substituents can be H, and wherein the acyl group has a linear chain length of at least three carbon atoms between the carbonyl functionality and the sulfur atom.

Additional maytansines for use in the context of the invention include compounds represented by formula (III):

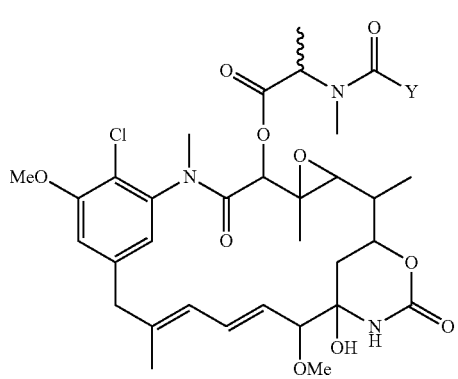

(III)

wherein
Y' represents $(CR^{1b}R^{2b})_p(CR^{3b}=C^{4b})_{p1}C\equiv C_{p2}A_{p3}(CR^{5b}P^{6b})_{p4}D_{p5}(CR^{7b}=CR^{8b})_{p6}(C\equiv C)_{p7}B_{p8}(CR^{9b}R^{10b})_p CR^{11b}R^{12b}SZ$, A, B, D are each independently $C_3$-$C_9$-cycloalkyl or $C_3$-$C_9$-cycloalkenyl, $C_6$-$C_{10}$ aryl, 5- to 7-membered heteroaryl, or 5- to 7-membered heteraliocyclic, wherein each of $R^{1b}$, $R^{2b}$, $R^{3b}$, $R^{4b}$, $R^{5b}$, $R^{6b}$, $R^{7b}$, $R^{8b}$, $R^{9b}$, $R^{10b}$, $R^{11b}$ and $R^{12b}$ is independently H, $C_1$-$C_6$ alkyl, $C_1$-$C_6$ alkenyl $C_6$-$C_{10}$ aryl, or 5- to 7-membered heteroaryl, or 5- to 7-membered heteraliocyclic, wherein p1, p2, p3, p4, p5, p6, p7, p8, and p9 are each independently zero or an integer from 1 to 5, provided that at least two of p1, p2, p3, p4, p5, p6, p7, p8, and p9 are not zero at any one time.

Suitable molecules useful as imaging agents include, but are not limited to, dyes, such as fluorescein dyes, rhodamine dyes, near IR dyes, and SPECT imaging agents, such as any radionuclei chelator known in the art. Examples of rhodamine dyes include, but are not limited to, 5-carboxytetramethylrhodamine (5-TAMRA), rhodamine B, rhodamine 6G, TRITC, Texas Red, rhodamine 123, sulforhodamine 101, and the like. Examples of rhodamine dyes include, but are not limited to, fluorescein, 5-amino-fluorescein, 6-amino-fluorescein, fluorescein isocyanate (FITC), fluorescein-5-maleimide, NHS-fluorescein, Oregon Green, Tokyo Green, Singapore Green, Philadelphia Green, and the like. Examples of near IR dyes include, S-0456. Examples of radionuclei chelators include, but are not limited to those described in WO03/092742.

In some embodiments, A is fluorescein dye of the formula

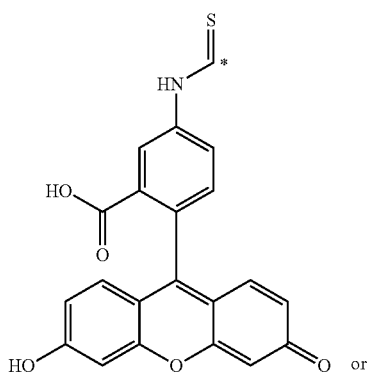

or

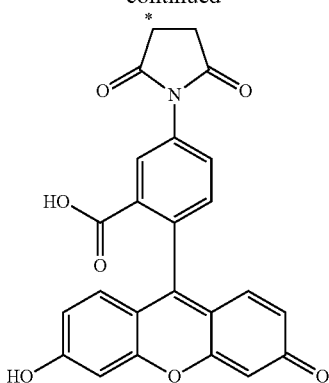

wherein * represents a covalent bond to the rest of the conjugate.

In other embodiments, suitable imaging agents as described herein include, but are not limited to, PET or SPECT imaging agents, such as radio-imaging agents comprising at least one a radioactive isotope of a metal (a.k.a. a radionuclide) coordinated to a chelating group. Illustrative radioactive metal isotopes include isotopes of technetium, rhenium, gallium, gadolinium, indium, copper, and the like. In some embodiments, suitable radionuclides include, but are not limited to $^{111}$In, $^{99m}$Tc, $^{64}$Cu, $^{67}$Cu, $^{67}$Ga, $^{68}$Ga, and the like. Illustrative chelating groups useful in connection with the present disclosure, including but not limited to, a radical of 1,4,7,10-tetraazacyclododecane-1,4,7,10-tetraacetic acid (DOTA), 1,4,7-triazacyclononane-1,4,7-triacetic acid (NOTA), 1,4,8,11-tetraazacyclotetradecane-1,4,8,11-tetraacetic acid (TETA), 2-(4,7,10-tris(carboxymethyl)-1,4,7,10-tetraazacyclododecan-1-yl)pentanedioic acid (DOTAGA), 2-(4,7-bis(carboxymethyl)-1,4,7-triazonan-1-yl)pentanedioic acid (NODAGA), diethylenetriaminepentaacetic acid (DTPA), 2,2',2''-(3,6,9-triaza-1-(2,6)-pyridinacyclodecaphane-3,6,9-triyl)triacetic acid (PCTA), 2,2'-((2-(4,7-bis(carboxymethyl)-1,4,7-triazonan-1-yl)ethyl)azanediyl)diacetic acid (NETA), and the like. Additional illustrative examples of radionuclide imaging agents are described in U.S. Pat. No. 9,193,763, the disclosure of which is incorporated herein by reference.

In one embodiment, the methods described herein can be used for both human clinical medicine and veterinary applications as a "subject". Thus, a "subject" can be administered the conjugates described herein, and can be human ("patient") or, in the case of veterinary applications, can be a laboratory, agricultural, domestic, or wild animal. In one aspect, the subject can be a human patient, a laboratory animal such as a rodent (e.g., mice, rats, hamsters, etc.), a rabbit, a monkey, a chimpanzee, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

In various embodiments, the cancers described herein can be a cancer cell population that is tumorigenic, including benign tumors and malignant tumors, or the cancer can be non-tumorigenic. The cancer can arise spontaneously or by such processes as mutations present in the germline of the patient or somatic mutations, or the cancer can be chemically-, virally-, or radiation-induced. Cancers applicable to the invention described herein include, but are not limited to, a carcinoma, a sarcoma, a lymphoma, a melanoma, a mesothelioma, a nasopharyngeal carcinoma, a leukemia, an adenocarcinoma, and a myeloma.

In some aspects the cancers can be lung cancer, bone cancer, pancreatic cancer, skin cancer, cancer of the head, cancer of the neck, cutaneous melanoma, intraocular melanoma uterine cancer, ovarian cancer, endometrial cancer, leiomyosarcoma, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, cholangiocarcinoma, Hurthle cell thyroid cancer or adenocarcinoma of the gastroesophageal junction.

In some embodiments, the present disclosure relates to targeted NIR imaging, wherein a conjugate of the disclosure provides selective imaging of cells and tissues that express the CA IX protein. It will be appreciated that the in vitro or in vivo imaging method used in connection with a conjugate of the disclosure is not particularly limited, and may be any conventional in vitro or in vivo imaging method known in the art. Furthermore, such imaging methods known in the art can be carried out using any instrumentation or assay kit known in the art, including, but not limited to fluorescent microscopy systems, such as the Nikon 90i, in vivo fluorescence imaging systems, such as the Caliper IVIS Lumina II Imaging station (often coupled to an a camera, such as the ISOON5160 Andor Nikon camera), and the like.

In some embodiments, the present disclosure provides methods for imaging a population of cell or tissue, either in vitro or in vivo. It will be appreciated that such in vitro methods can be carried out by any method known in the art. In some embodiments, in vitro imaging methods described herein can include a. contacting a population of cells with a conjugate of the disclosure to provide the conjugate bound to cells expressing a CA IX protein, and b. visualizing the conjugate bound to cells by irradiation with near-infrared wavelength light. It will be appreciated that visualizing the conjugate bound to cells by irradiation with near-infrared wavelength light can include irradiation at an excitation wavelength and detection at an emission wavelength. Thus, in some embodiments, in vitro imaging methods described herein can include a. contacting a population of cells with a conjugate of the disclosure to provide the conjugate bound to cells expressing a CA IX protein, b. irradiating the conjugate bound to cells expressing a CA IX protein with near-infrared wavelength light, and c. detecting light emitted from the cancer cells at an emission wavelength.

In some embodiments, tissues, such as cancerous tumors, can be imaged according to the methods described herein. For example, in some embodiments, in vivo imaging methods described herein can include a. administering to the patient a conjugate of the disclosure; or a pharmaceutically acceptable salt thereof, to provide the conjugate bound to cells expressing a CA IX protein; and b. visualizing the conjugate bound to cells expressing a CA IX protein by irradiation with near-infrared wavelength light. It will be appreciated that visualizing the conjugate bound to cells by irradiation with near-infrared wavelength light can include irradiation at an excitation wavelength and detection at an emission wavelength. Thus, in some embodiments, in vivo imaging methods described herein can include a. administering to the patient a conjugate of the disclosure; or a pharmaceutically acceptable salt thereof, to provide the conjugate bound to cells expressing a CA IX protein; b. irradiating the conjugate bound to cells expressing a CA IX protein with near-infrared wavelength light; and c. detecting light emitted from the cancer cells at an emission wavelength. It will be appreciated that visualizing the conjugate bound to cells by irradiation with near-infrared wavelength light can be carried out using any known NIR imaging techniques (diagnostic or otherwise) or instrumentation known in the art.

The wavelength of light used in connection with the imaging methods described herein can be in the near-infrared wavelength region, such as in the range of about 600 nm to about 2500 nm. Such wavelength can be a range of wavelengths or a single wavelength. In some embodiments, the excitation wavelength can be in the range of from about 600 nm to about 2500 nm. In some embodiments, the excitation wavelength can be in the range of from about 600 nm to about 900 nm. In some embodiments, the excitation wavelength can be in the range of from about 700 nm to about 750 nm. In some embodiments, the excitation wavelength can be about 745 nm. In some embodiments, the emission wavelength can be in the range of from about 600 nm to about 2500 nm. In some embodiments, the emission wavelength can be in the range of from about 750 nm to about 900 nm. In some embodiments, the emission wavelength can be in the range of from about 750 nm to about 790 nm. In some embodiments, the emission wavelength can be about 790 nm. In some embodiments, the emission wavelength can be the emission wavelength of ICG (also known as indocyanine green dye).

In other embodiments of the methods described herein, pharmaceutically acceptable salts of the conjugates described herein are provided. Pharmaceutically acceptable salts of conjugates described herein include acid addition and base salts thereof.

Suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the conjugates described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

Depending upon the cancer type as described herein, the route of administration and/or whether the conjugates are administered locally or systemically, a wide range of permissible dosages are contemplated herein, including doses falling in the range from about 1 µg/kg to about 1 g/kg. In other embodiments, doses falling in the range from about 0.001 µmol/kg to about 1 µmol/kg can be used. The dosages may be single or divided, and may administered according to a wide variety of protocols, including q.d., b.i.d., t.i.d., or even every other day, biweekly (b.i.w.), once a week, four times per week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

Any effective regimen for administering the conjugates described herein can be used. For example, conjugates described herein can be administered as single doses, or the doses can be divided and administered as a multiple-dose daily regimen. Further, a staggered regimen, for example, one to five days per week can be used as an alternative to daily treatment, and for the purpose of the methods described herein, such intermittent or staggered daily regimen is considered to be equivalent to every day treatment and is contemplated. In one illustrative embodiment the patient is treated with multiple injections of a conjugate described herein to treat the cancer. In one embodiment, the patient is injected multiple times (preferably about 2 up to about 50 times) with a conjugate described herein, for example, at 12-72 hour intervals or at 48-72 hour intervals. Additional injections of a conjugate described herein can be administered to the patient at an interval of days or months after the initial injections(s) and the additional injections can prevent recurrence of the cancer.

In one embodiment, the conjugates described herein may be administered as a formulation in association with one or more pharmaceutically acceptable carriers. The carriers can be excipients. The choice of carrier will to a large extent depend on factors such as the particular mode of administration, the effect of the carrier on solubility and stability, and the nature of the dosage form. Pharmaceutical compositions suitable for the delivery of conjugates as described herein and methods for their preparation will be readily apparent to those skilled in the art. Such compositions and methods for their preparation may be found, for example, in Remington: The Science & Practice of Pharmacy, 21th Edition (Lippincott Williams & Wilkins, 2005), incorporated herein by reference.

In one illustrative aspect, a pharmaceutically acceptable carrier includes any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds can also be incorporated into compositions of the invention.

In various embodiments, liquid formulations may include suspensions and solutions. Such formulations may comprise a carrier, for example, water, ethanol, polyethylene glycol, propylene glycol, methylcellulose or a suitable oil, and one or more emulsifying agents and/or suspending agents. Liquid formulations may also be prepared by the reconstitution of a solid.

In one embodiment, an aqueous suspension may contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents.

In one illustrative embodiment, dispersible powders and granules suitable for preparation of an aqueous suspension by the addition of water provide the active ingredient in admixture with a dispersing or wetting agent, suspending agent and one or more preservatives. Additional excipients, for example, coloring agents, may also be present.

In other embodiments, isotonic agents, for example, sugars, polyalcohols such as mannitol, sorbitol, or sodium chloride can be included in the composition. Prolonged absorption of injectable compositions can be brought about by including in the composition an agent which delays absorption, for example, monostearate salts and gelatin.

Illustrative formats for oral administration include tablets, capsules, elixirs, syrups, and the like.

In one aspect, a conjugate as described herein may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. In other embodiments, any of the liquid formulations described herein may be adapted for parenteral administration of the conjugates described herein. The preparation of parenteral formulations under sterile conditions, for example, by lyophilization under sterile conditions, may readily be accomplished using standard pharmaceutical techniques well known to those skilled in the art. In one embodiment, the solubility of a conjugate as described herein used in the preparation of a parenteral formulation may be increased by the use of appropriate formulation techniques, such as the incorporation of solubility-enhancing agents.

In various embodiments, formulations for parenteral administration may be formulated for immediate and/or modified release. In one illustrative aspect, active agents of the invention (i.e., the conjugates described herein) may be administered in a time release formulation, for example in a composition which includes a slow release polymer. The active agents can be prepared with carriers that will protect the conjugate against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PGLA). Methods for the preparation of such formulations are generally known to those skilled in the art. In another embodiment, the conjugates described herein or compositions comprising the conjugates may be continuously administered, where appropriate.

In one embodiment, a kit is provided. If a combination of active conjugates as described herein is to be administered, two or more pharmaceutical compositions may be combined in the form of a kit suitable for sequential administration or co-administration of the compositions. Such a kit comprises two or more separate pharmaceutical compositions, at least one of which contains a conjugate described herein, and means for separately retaining the compositions, such as a container, divided bottle, or divided foil packet. In another embodiment, compositions comprising one or more conjugates as described herein, in containers having labels that provide instructions for use of the conjugates as described herein for patient selection and/or treatment are provided.

In one embodiment, sterile injectable solutions can be prepared by incorporating the active agent in the required amount in an appropriate solvent with one or a combination of ingredients described above, as required, followed by filtered sterilization. Typically, dispersions are prepared by incorporating the conjugate into a sterile vehicle which contains a dispersion medium and any additional ingredients of those described above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof, or the ingredients may be sterile-filtered together.

The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In one embodiment, the proper fluidity can be maintained, for example, by the use of a coating such as lecithin, by the maintenance of the required particle size in the case of dispersion and by the use of surfactants.

The conjugates described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The conjugates described herein may be capable of existing as geometric isomers. Accordingly, it is to be understood that the present invention includes pure geometric isomers or mixtures of geometric isomers.

It is appreciated that the conjugates described herein may exist in unsolvated forms as well as solvated forms, including hydrated forms. In general, the solvated forms are equivalent to unsolvated forms and are encompassed within the scope of the present invention. The conjugates described herein may exist in multiple crystalline or amorphous forms. In general, all physical forms are equivalent for the uses contemplated by the present invention and are intended to be within the scope of the present invention.

In another embodiment, compositions and/or dosage forms for administration of a conjugate described herein are prepared from a conjugate described herein with a purity of at least about 90%, or about 95%, or about 96%, or about 97%, or about 98%, or about 99%, or about 99.5%. In another embodiment, compositions and or dosage forms for administration of a conjugate described herein are prepared from a conjugate described herein with a purity of at least 90%, or at least 95%, or at least 96%, or at least 97%, or at least 98%, or at least 99%, or at least 99.5%.

EXAMPLES

The following data may suggest the therapeutic and radioactive imaging applications of carbonic anhydrase targeting ligands. A ligand (FBSA, Scheme 1, compound 3) was developed by Daumantas Matulis, et al. (*J. Med. Chem.* 2014, 57, 9435-9446).

As described herein, the data suggests that a $PEG_2$ linker length, or a variant thereof, may contribute to an apparent binding affinity. Some of the data may also suggest a design of small molecule therapeutic conjugates based upon FBSA targeting, such as a tubulysin conjugate (Conjugate 12, (FBSA-$PEG_2$-tubulysin B) and Conjugate 14, FBSA-tubulysin B conjugate with a hydrophilic linker).

Abbreviations

The examples described herein use materials, including but not limited to, those described by the following abbreviations known to those skilled in the art:

| | |
|---|---|
| FBSA | fluorinated-benzosulfonamide |
| PEG | polyethylene glycol |
| mL | milliliters |
| M | molar |
| THF | tetrahydrofuran |
| ° C. | degrees Celsius |
| g | grams |
| mg | milligrams |
| MP | melting point |
| IR | infrared radiation |
| cm | centimeter |
| Asym | asymmetric |
| Sym | symmetric |
| TEA | triethylamine |
| μL | microliter |
| MeOH | methanol |
| $H_2O_2$ | hydrogen peroxide |
| LC-MS | liquid chromatography mass spectrometry |
| DMSO | dimethyl sulfoxide |
| nmoles | nanomoles |
| umole or μmole | micromole |
| mmole | millimole |
| umole/kg or μmol/kg | micromoles per kilogram |
| i-PrOH | isopropyl alcohol |
| fmoc | fluorenylmethyloxycarbonyl |
| HATU | 1-[Bis(dimethylamino)methylene]-1H-1,2,3-triazolo[4,5-b] pyridinium 3-oxid hexafluorophosphate |
| DIPEA | N,N-diisopropylethylamine |
| HPLC | high-performance liquid chromatography |
| LRMS | Low resolution mass spectrometry |
| HPLC | high-performance liquid chromatography |
| DMF | dimethylformamide |
| Boc | tert-butyloxycarbonyl |
| SPECT/CT | single photon emission computed tomography |
| THF | tetrahydrofuran |
| nM | nanomolar |
| DMEM | Dulbecco's Modified Eagle Medium |
| μCi/mL or uCi/mL | microcurie per milliliter |
| μCi or uCi | microcurie |
| h or hr | hour |

Example 1

Synthesis of Carbonic Anhydrase

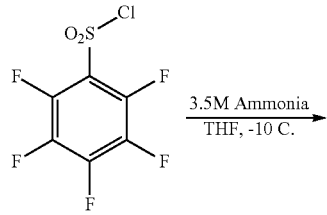

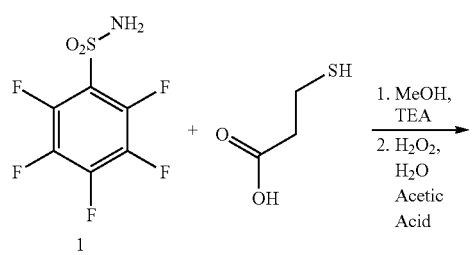

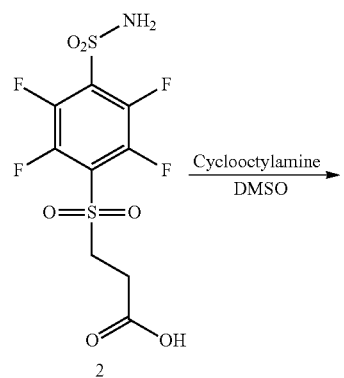

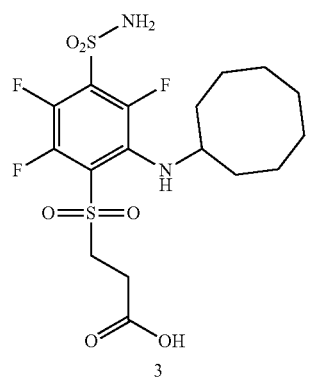

Scheme 1. Synthesis of FBSA, Compound 3, a high affinity carbonic anhydrase small molecule targeting ligand.

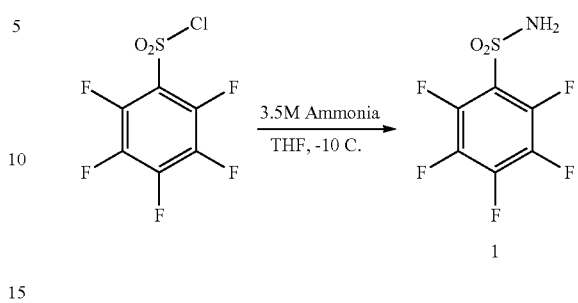

Synthesis of Pentafluorobenzenesulfonamide, 1

A stirring mixture of pentafluorobenzene sulfonyl chloride (2.60 mL) in tetrahydrofuran was chilled to −10° C. using an ice/NaCl cooling bath. Then 3.5M ammonia in methanol/ethanol (6.00 mL) was added dropwise. The reaction was then allowed to warm to room temperature and stir for 3.5 hours. The solvent was then removed under vacuum and recrystallized in water. Yield: 2.7404 g, MP: 153.2-154.8° C. (Lit: 156° C.), IR (cm$^{-1}$): 3343.00 (—NH$_2$, Asym), 3264 (—NH$_2$, Sym)

Example 2

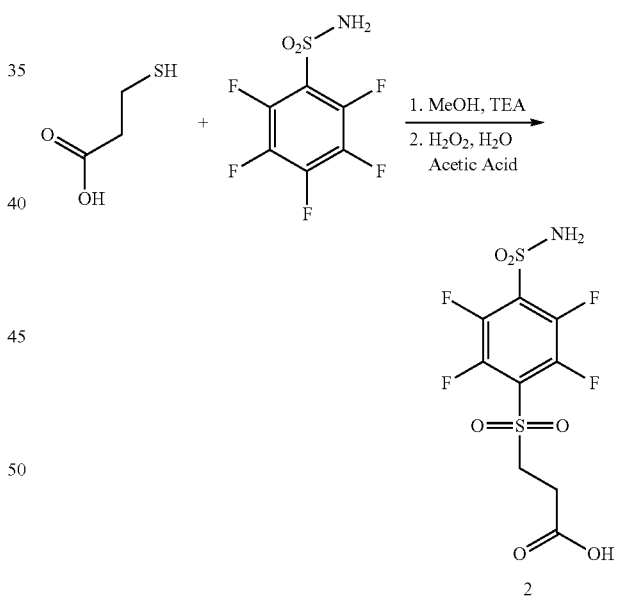

Synthesis of 3-((2,3,5,6-tetrafluoro-4-sulfamoylphenyl)sulfonyl)propanoic acid, 2

Pentafluorobenzenesulfonamide (950.4 mg), triethylamine (1.400 mL) and 3-mercaptopropanoic acid (368 μL) were added to a stirring methanol (40 mL) solution. The reaction was then refluxed for 24 hours, then dried under vacuum. The resulting residue was then dissolved in a 2:1 mixture of acetic acid to water, respectively. This mixture was then heated to 70° C. and 2 mL portions of 30% hydrogen peroxide were added every two hours until the total volume of peroxide added reached 10 mL. The reaction was then allowed to stir at 70° C. for a total of 24 hours. Acetic acid was removed under vacuum and the resulting precipitate was filtered and washed with water. Yield: 0.5679 g, LC-MS (M+H$_2$O): 383.0

Reference: Robson, P.; Smith, T. A.; Stephens, R.; Tatlow, J. C., 691. Aromatic polyfluoro-compounds. Part XIII Derivatives of penta- and 2,3,5,6-tetra-fluorothiophenol. Journal of the Chemical Society (Resumed) 1963, (0), 3692-3703.

Example 3

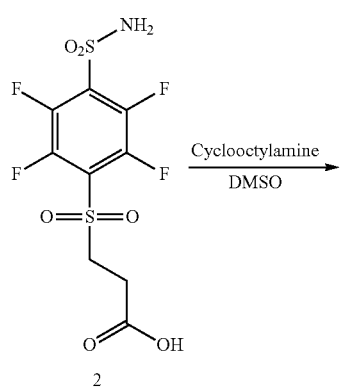

Synthesis of 3-((2-(cyclooctylamino)-3,5,6-trifluoro-4-sulfamoylphenyl)sulfonyl)propanoic acid, 3

Compound 2 (400 mg) was dissolved in DMSO (2 mL), and then cyclooctylamine (2 equivalents) was added and the reaction mixture was stirred at room temperature for 24 hours. The reaction was quenched with water and concentrated ammonium chloride. The resulting precipitate was extracted with ethyl acetate and dried over sodium sulfate. The extract was then dried on silica and purified by flash chromatography. Yield: 0.1662 g, LC-MS (M+1): 473.2.

Example 4

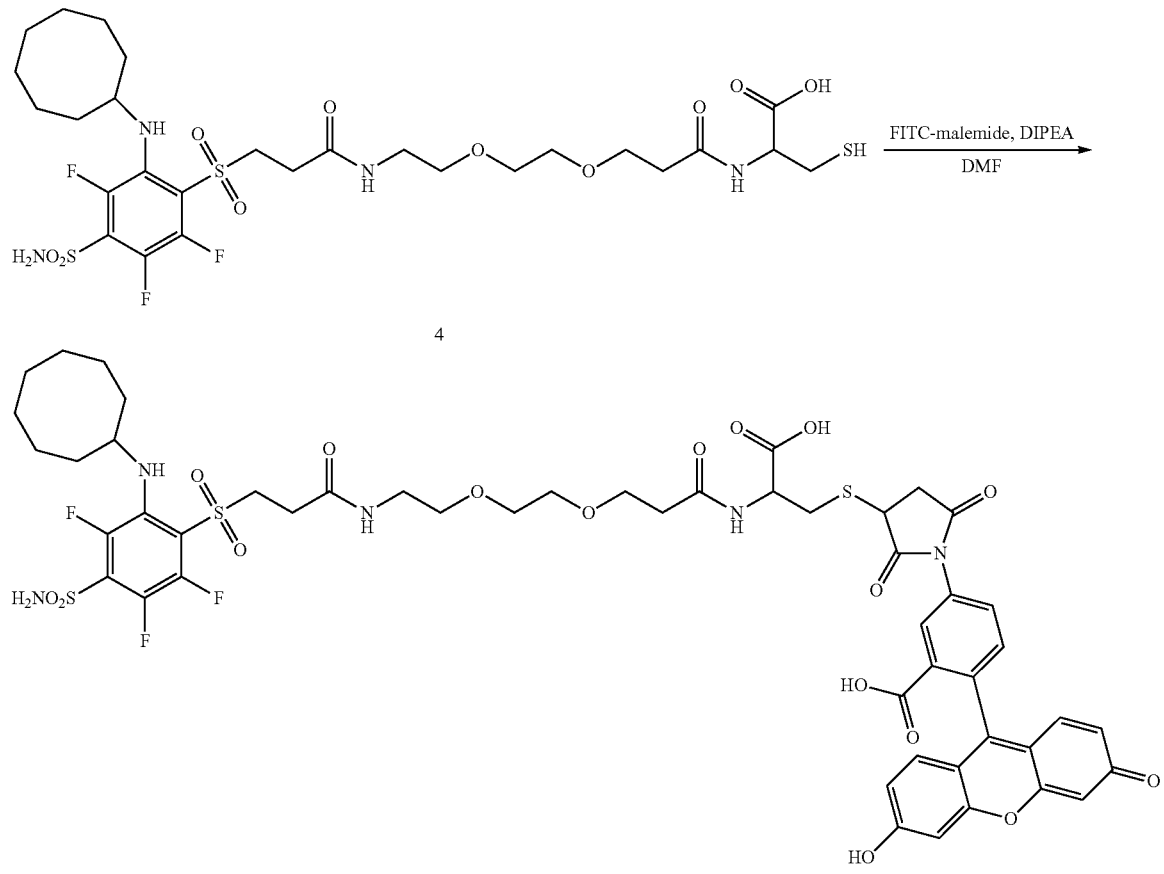

Synthesis of (3-(2-(2-(3-((2-(cyclooctylamino)-3,5,6-trifluoro-4-sulfamoylphenyl)sulfonyl)propanamido)ethoxy)ethoxy)propanoyl)cysteine, 4

Compound 4 was synthesized by the following solid phase methodology. H-Cys(Trt)-2-chlorotrityl resin (100 mg, 0.64 mmole/g) was swollen with 3 mL of dichloromethane (DCM) followed by 3 mL of dimethylformamide (DMF). After swelling the resin in DMF, a solution of 3-[2-[2-(9H-fluoren-9-ylmethoxycarbonylamino)ethoxy]ethoxy]propanoic acid (51.1 mg, 0.128 mmoles), 1-[Bis(dimethylamino)methylene]-1H-1,2,3-triazolo[4,5-b]pyridinium 3-oxid hexafluorophosphate (60.8 mg, 0.16 mmoles) and N,N-diisopropylethylamine (0.056 ml, 0.32 mmoles) in DMF (3 mL) was added. Argon was bubbled for 2 h, and resin was washed three times with 3 mL of DMF and 3 times with 3 mL i-PrOH. The fmoc was removed with a piperidine solution (20% in DMF, 3×5 ml) and the resin was washed three times with 3 mL of DMF and 3 times with 3 mL i-PrOH. A solution of 3-((2-(cyclooctylamino)-3,5,6-trifluoro-4-sulfamoylphenyl)sulfonyl)propanoic acid (33.3 mg, 0.074 mmoles), HATU (24.3 mg, 0.064 mmoles) and DIPEA (0.034 ml, 0.192 mmoles) in DMF was added. Argon was bubbled for 2 hr, and resin was washed three times with 3 mL of DMF and 3 times with 3 mL i-PrOH. Compound 4 was cleaved from the resin using a mixture of trifluoroacetic acid:triisopropylsilane:H$_2$O:ethanedithiol (95:2.5:2.5:2.5) and concentrated under vacuum. The concentrated product was precipitated in diethyl ether and dried under vacuum. Crude conjugate was purified by reverse-phase HPLC [A=2 mM ammonium acetate buffer (pH 7.0), B=CH$_3$CN, solvent gradient: 0% B to 100% B in 30 min] to yield the product as a clear oil (54%). LRMS-LC/MS (m/z): [M+H]$^+$ calculated for C$_{27}$H$_{41}$F$_3$N$_4$O$_{10}$S$_3$, 734.19; found, 735.2.

Synthesis of 2-(((1-(3-carboxy-4-(6-hydroxy-3-oxo-3H-xanthen-9-yl)phenyl)-2,5-dioxopyrrolidin-3-yl)thio)methyl)-16-((2-(cyclooctylamino)-3,5,6-trifluoro-4-sulfamoylphenyl)sulfonyl)-4,14-dioxo-7,10-dioxa-3,13-diazahexadecanoic acid, 5

To a solution of Compound 4 (5 mg, 0.0068 mmoles) in DMF (1 mL) was added fluorescein-5-maleimide (3.2 mg, 0.0075 mmoles) and N,N-diisopropylethylamine (0.006 ml, 0.034 mmoles) and stirred for 1 hour at room temperature. The crude reaction mixture was purified reverse-phase HPLC [A=2 mM ammonium acetate buffer (pH 7.0), B=CH$_3$CN, solvent gradient: 0% B to 100% B in 30 min] to yield the product as a yellow powder (61%). LRMS-LC/MS (m/z): [M+H]$^+$ calculated for C$_{51}$H$_{54}$F$_3$N$_5$O$_{17}$S$_3$, 1161.26; found, 1162.2.

Example 5

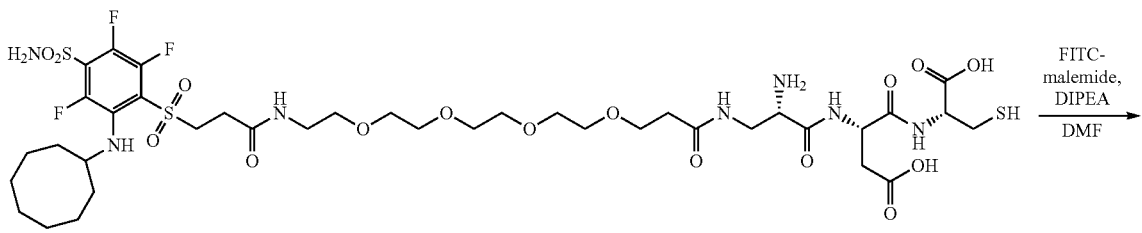

6

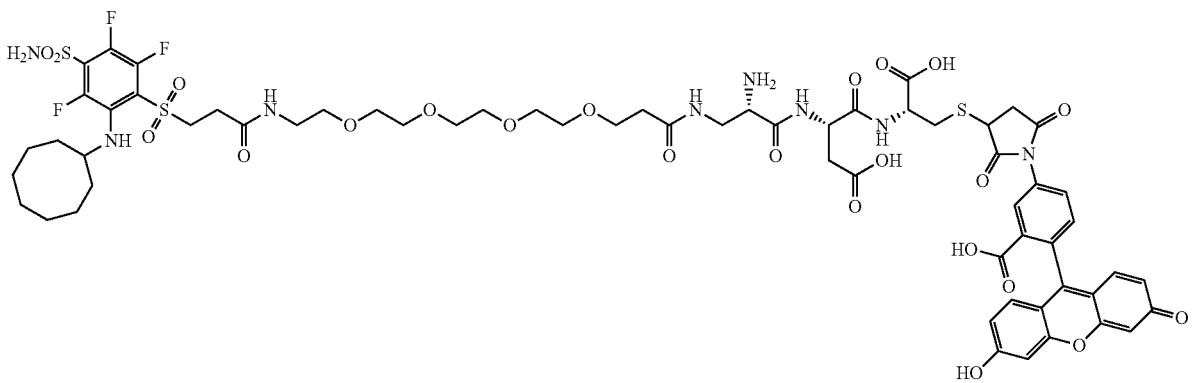

7

Synthesis of (2R,5S,8S)-8-amino-5-(carboxymethyl)-29-((2-(cyclooctylamino)-3,5,6-trifluoro-4-sulfamoylphenyl)sulfonyl)-2-(mercaptomethyl)-4,7,11,27-tetraoxo-14,17,20,23-tetraoxa-3,6,10,26-tetraazanonacosanoic acid, 6

Compound 6 was synthesized by the following solid phase methodology. H-Cys(Trt)-2-chlorotrityl resin (100 mg, 0.64 mmole/g) was swollen with 3 mL of dichloromethane (DCM) followed by 3 mL of dimethylformamide (DMF). After swelling the resin in DMF, a solution of Fmoc-Asp(tBu)-OH (52.7 mg, 0.128 mmoles), 1-[Bis(dimethylamino)methylene]-1H-1,2,3-triazolo[4,5-b]pyridinium 3-oxid hexafluorophosphate (60.8 mg, 0.16 mmoles) and N,N-diisopropylethylamine (0.056 ml, 0.32 mmoles) in DMF (3 mL) was added. Argon was bubbled for 2 hr, and resin was washed three times with 3 mL of DMF and 3 times with 3 mL i-PrOH. The fmoc was removed with a piperidine solution (20% in DMF, 3×5 ml) and the resin was washed three times with 3 mL of DMF and three times with 3 mL i-PrOH. A solution of Boc-DAP(Fmoc)-OH (54.6 mg, 0.128 mmoles), 1-[Bis(dimethylamino)methylene]-1H-1,2,3-triazolo[4,5-b]pyridinium 3-oxid hexafluorophosphate (60.8 mg, 0.16 mmoles) and N,N-diisopropylethylamine (0.056 ml, 0.32 mmoles) in DMF (3 mL) was added. Argon was bubbled for 2 hr, and resin was washed three times with 3 mL of DMF and three times with 3 mL i-PrOH. The fmoc was removed with a piperidine solution (20% in DMF, 3×5 ml) and the resin was washed three times with 3 mL of DMF and three times with 3 mL i-PrOH. A solution of 3-[2-[2-[2-[2-[2-(9H-fluoren-9-ylmethoxycarbonylamino)ethoxy]ethoxy]ethoxy]ethoxy]propanoic acid (62.4 mg, 0.128 mmoles), 1-[Bis(dimethylamino)methylene]-1H-1,2,3-triazolo[4,5-b]pyridinium 3-oxid hexafluorophosphate (60.8 mg, 0.16 mmoles) and N,N-diisopropylethylamine (0.056 ml, 0.32 mmoles) in DMF was added. Argon was bubbled for 2 hr, and resin was washed three times with 3 mL of DMF and three times with 3 mL i-PrOH. The fmoc was removed with a piperidine solution (20% in DMF, 3×5 ml) and the resin was washed three times with 3 mL of DMF and 3 times with 3 mL i-PrOH. A solution of 3-((2-(cyclooctylamino)-3,5,6-trifluoro-4-sulfamoylphenyl)sulfonyl)propanoic acid (33.3 mg, 0.074 mmoles), HATU (24.3 mg, 0.064 mmoles) and DIPEA (0.034 ml, 0.192 mmoles) in DMF was added. Argon was bubbled for 2 hr, and resin was washed three times with 3 mL of DMF and three times with 3 mL i-PrOH. Compound 3 was cleaved from the resin using a mixture of trifluoroacetic acid:triisopropylsilane:$H_2O$:ethanedithiol (95:2.5:2.5:2.5) and concentrated under vacuum. The concentrated product was precipitated in diethyl ether and dried under vacuum. Crude compound 6 was purified by reverse-phase HPLC [A=2 mM ammonium acetate buffer (pH 7.0), B=$CH_3CN$, solvent gradient: 0% B to 100% B in 30 min] to yield the product as a clear oil (62%). LRMS-LC/MS (m/z): [M+H]$^+$ calculated for $C_{38}H_{60}F_3N_7O_{16}S_3$, 1023.32; found, 1024.3.

Synthesis of 5-(3-(((2R,5S,8S)-8-amino-2-carboxy-5-(carboxymethyl)-29-((2-(cyclooctylamino)-3,5,6-trifluoro-4-sulfamoylphenyl)sulfonyl)-4,7,11,27-tetraoxo-14,17,20,23-tetraoxa-3,6,10,26-tetraazanonacosyl)thio)-2,5-dioxopyrrolidin-1-yl)-2-(6-hydroxy-3-oxo-3H-xanthen-9-yl)benzoic acid, 7

To a solution of Compound 6 (2 mg, 0.002 mmoles) in DMF (1 mL) was added fluorescein-5-maleimide (0.85 mg, 0.002 mmoles) and N,N-diisopropylethylamine (0.002 ml, 0.01 mmoles) and stirred for 1 hour at room temperature. The crude reaction mixture was purified reverse-phase HPLC [A=2 mM ammonium acetate buffer (pH 7.0), B=$CH_3CN$, solvent gradient: 0% B to 100% B in 30 min] to yield the Conjugate 7 as a yellow powder (76%). LRMS-LC/MS (m/z): [M+H]+ calculated for $C_{62}H_{73}F_3N_8O_{23}S_3$, 1450.39; found, 1451.3.

Example 6

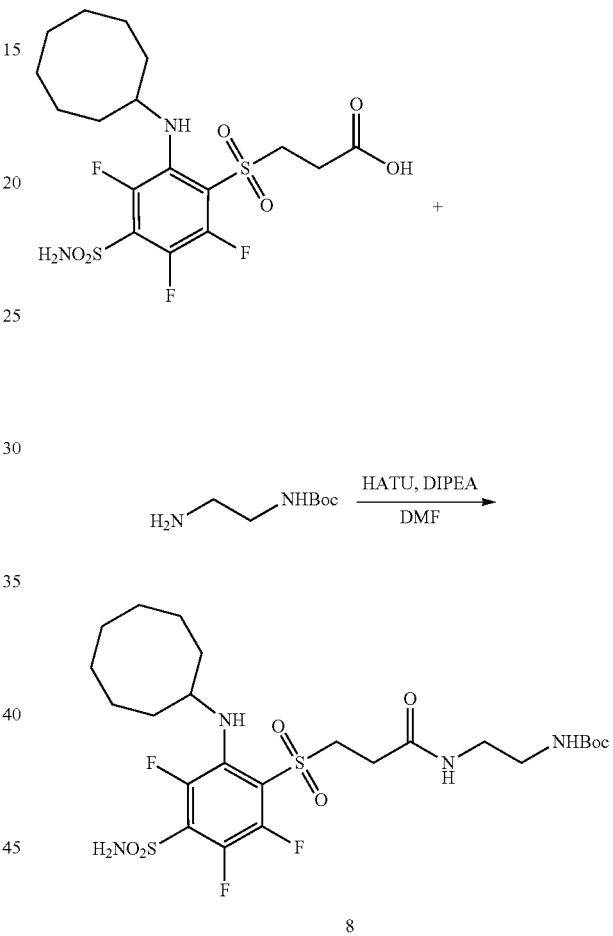

8

Synthesis of tert-butyl (2-(3-((2-(cyclooctylamino)-3,5,6-trifluoro-4-sulfamoylphenyl)sulfonyl)propanamido)ethyl)carbamate, 8

To a solution of 3-((2-(cyclooctylamino)-3,5,6-trifluoro-4-sulfamoylphenyl)sulfonyl)propanoic acid (20 mg, 0.042 mmoles) in DMF (2 ml) was added tert-butyl (2-aminoethyl) carbamate (7.40 mg, 0.0462 mmoles) and allowed to stir under argon for 10 minutes at room temperature. 1-[Bis(dimethylamino)methylene]-1H-1,2,3-triazolo[4,5-b]pyridinium 3-oxid hexafluorophosphate (16 mg, 0.042 mmoles) and N,N-diisopropylethylamine (0.022 ml, 0.126 mmoles) were then added. The reaction was stirred for 1 hour before quenching with water (10 ml) and extracted with ethyl acetate (3×25 ml). The organic layers were combined, washed with brine, and dried over anhydrous sodium sulfate. The solvent was concentrated under vacuum, and the crude mixture was purified on silica gel using 10% methanol/dichloromethane to obtain Compound 8 as a colorless oil (21.4 mg, 83%). LRMS-LC/MS (m/z): [M+H]$^+$ calculated for $C_{24}H_{37}F_3N_4O_7S_2$, 614.21; found, 615.2.

Example 7

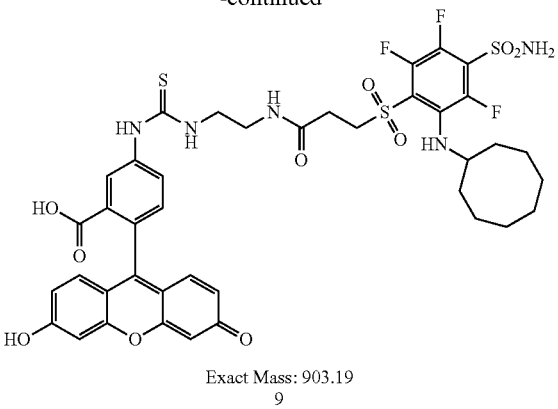

Exact Mass: 903.19

9

Synthesis of 5-(3-(2-(3-((2-(cyclooctylamino)-3,5,6-trifluoro-4-sulfamoylphenyl)sulfonyl)propanamido)ethyl)thioureido)-2-(6-hydroxy-3-oxo-3H-xanthen-9-yl)benzoic acid, 9

The tert-butyloxycarbonyl protecting group of Compound 8 (10 mg, 0.008 mmoles) was removed with a mixture of TFA/DCM (20%, 2 ml) for 30 minutes. The TFA/DCM mixture was removed under vacuum and the product brought forward without purification. To the vial containing the deprotected Compound 5, was added DMF (1 ml) and N,N-diisopropylethylamine (0.007 ml, 0.04 mmoles) and allowed to stir for five minutes before fluorescein-5-maleimide (3.8 mg, 0.0088 mmoles) was added and allowed to stir for an additional hour. The crude mixture was purified without workup by purified reverse-phase HPLC [A=2 mM ammonium acetate buffer (pH 7.0), B=CH$_3$CN, solvent gradient: 0% B to 100% B in 30 min] to yield the product as a yellow powder (76%). LRMS-LC/MS (m/z): [M+H]$^+$ calculated for $C_{40}H_{40}F_3N_5O_{10}S_3$, 903.19; found, 904.2.

Example 8

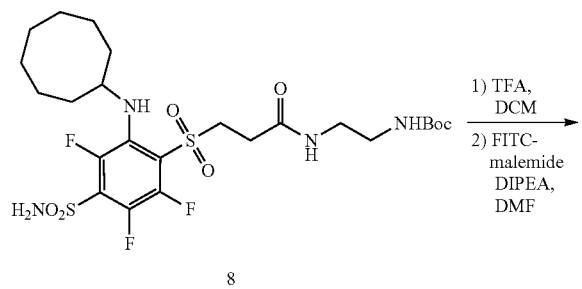

8

1) TFA, DCM
2) FITC-malemide DIPEA, DMF

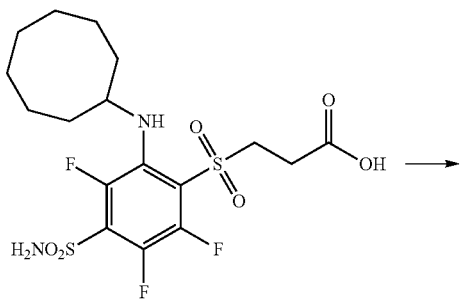

3

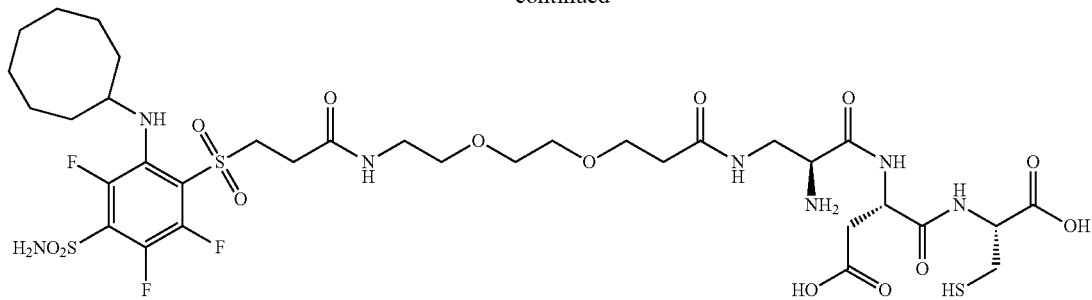

Exact Mass: 935.27
10

Synthesis of (2R,5S,8S)-8-amino-5-(carboxymethyl)-23-((2-(cyclooctylamino)-3,5,6-trifluoro-4-sulfamoylphenyl)sulfonyl)-2-(mercaptomethyl)-4,7,11,21-tetraoxo-14,17-dioxa-3,6,10,20-tetraazatricosanoic acid, 10

Compound 10 was synthesized by the following solid phase methodology. H-Cys(Trt)-2-chlorotrityl resin (100 mg, 0.64 mmole/g) was swollen with 3 mL of dichloromethane (DCM) followed by 3 mL of dimethylformamide (DMF). After swelling the resin in DMF, a solution of Fmoc-Asp(tBu)-OH (52.7 mg, 0.128 mmoles), 1-[Bis(dimethylamino)methylene]-1H-1,2,3-triazolo[4,5-b]pyridinium 3-oxid hexafluorophosphate (60.8 mg, 0.16 mmoles) and N,N-diisopropylethylamine (0.056 ml, 0.32 mmoles) in DMF (3 mL) was added. Argon was bubbled for 2 h, and resin was washed three times with 3 mL of DMF and three times with 3 mL i-PrOH. The fmoc was removed with a piperidine solution (20% in DMF, 3×5 ml) and the resin was washed three times with 3 mL of DMF and three times with 3 mL i-PrOH. A solution of Boc-DAP(Fmoc)-OH (54.6 mg, 0.128 mmoles), 1-[Bis(dimethylamino)methylene]-1H-1,2,3-triazolo[4,5-b]pyridinium 3-oxid hexafluorophosphate (60.8 mg, 0.16 mmoles) and N,N-diisopropylethylamine (0.056 ml, 0.32 mmoles) in DMF (3 mL) was added. Argon was bubbled for 2 h, and resin was washed three times with 3 mL of DMF and three times with 3 mL i-PrOH. The fmoc was removed with a piperidine solution (20% in DMF, 3×5 ml) and the resin was washed three times with 3 mL of DMF and 3 times with 3 mL i-PrOH. A solution of fmoc-9-amino-4,7-dioxanonanoic acid (51.12 mg, 0.128 mmoles), 1-[Bis(dimethylamino)methylene]-1H-1,2,3-triazolo[4,5-b]pyridinium 3-oxid hexafluorophosphate (60.8 mg, 0.16 mmoles) and N,N-diisopropylethylamine (0.056 ml, 0.32 mmoles) in DMF was added. Argon was bubbled for 2 h, and resin was washed three times with 3 mL of DMF and 3 times with 3 mL i-PrOH. The fmoc was removed with a piperidine solution (20% in DMF, 3×5 ml) and the resin was washed three times with 3 mL of DMF and 3 times with 3 mL i-PrOH. A solution of 3-((2-(cyclooctylamino)-3,5,6-trifluoro-4-sulfamoylphenyl)sulfonyl)propanoic acid (Compound 3, 33.3 mg, 0.074 mmoles), HATU (24.3 mg, 0.064 mmoles) and DIPEA (0.034 ml, 0.192 mmoles) in DMF was added. Argon was bubbled for 2 h, and resin was washed three times with 3 mL of DMF and 3 times with 3 mL i-PrOH. Compound 10 was cleaved from the resin using a mixture of trifluoroacetic acid:triisopropylsilane:H$_2$O:ethanedithiol (95:2.5:2.5:2.5) and concentrated under vacuum. The concentrated product was precipitated in diethyl ether and dried under vacuum. Crude conjugate was purified by reverse-phase HPLC [A=2 mM ammonium acetate buffer (pH 7.0), B=CH$_3$CN, solvent gradient: 0% B to 100% B in 30 min] to yield the product as a clear oil (62%). LRMS-LC/MS (m/z): [M+H]$^+$ calculated for C$_{34}$H$_{52}$F$_3$N$_7$O$_{14}$S$_3$, 935.27; found, 935.2. Note that Compound 10 may be used as a precursor for Conjugate 12, or could also be used a chelator of $^{99m}$Tc and may be used for SPECT/CT imaging applications as Conjugate 10.

Example 9

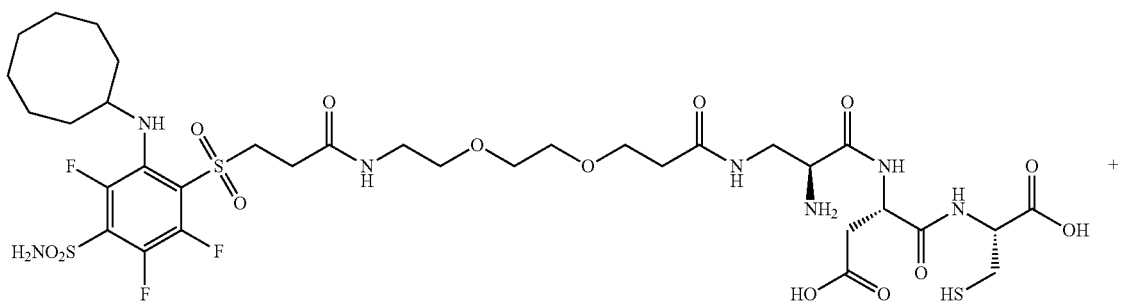

10

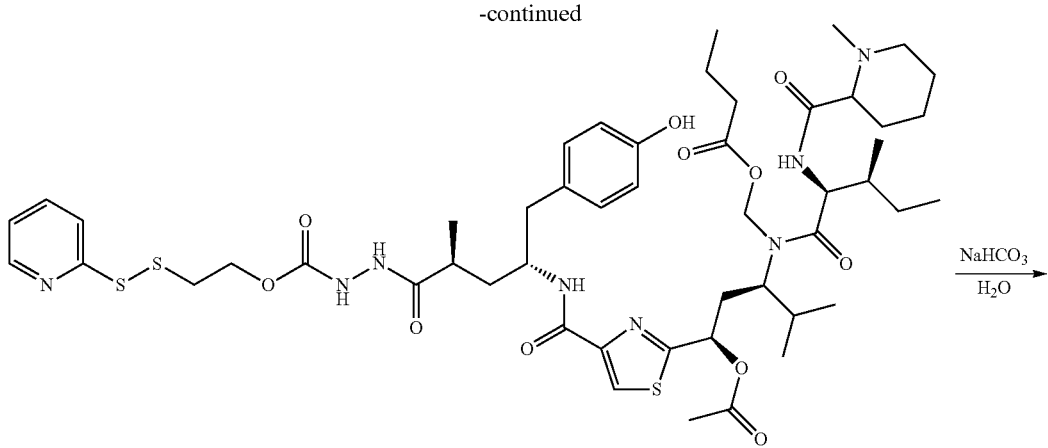

11

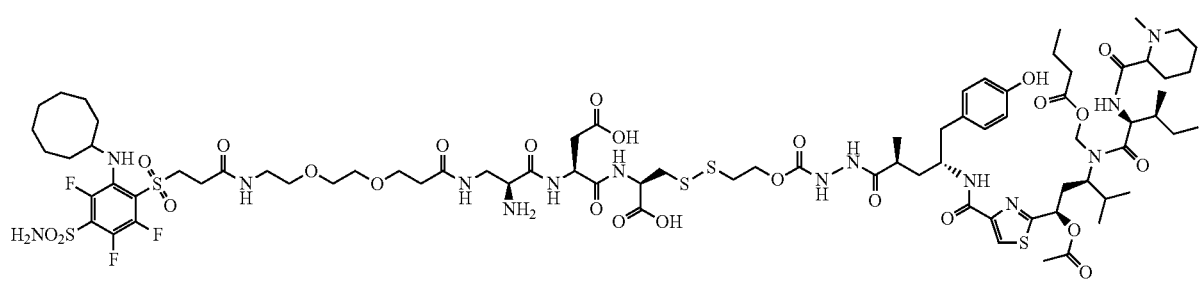

12
Chemical Formula: C<sub>79</sub>H<sub>119</sub>O<sub>25</sub>S<sub>5</sub>
Exact Mass: 1880.70

Synthesis of (3R,5S,16R,19S)-1-(2-(((1R,3R)-1-acetoxy-3-((2S,3S)—N-((butyryloxy)methyl)-3-methyl-2-(1-methylpiperidine-2-carboxamido)pentanamido)-4-methylpentyl)thiazol-4-yl)-19-((S)-16-amino-1-((2-(cyclooctylamino)-3,5,6-trifluoro-4-sulfamoylphenyl)sulfonyl)-3,13-dioxo-7,10-dioxa-4,14-diazaheptadecan-17-amido)-16-carboxy-3-(4-hydroxybenzyl)-5-methyl-1,6,9,18-tetraoxo-10-oxa-13,14-dithia-2,7,8,17-tetraazahenicosan-21-oic acid, 12

A solution of saturated sodium bicarbonate (10 mL) in distilled water was bubbled with argon continuously for 30 min. Compound 9 (1.5 mg, 0.0016 mmol) was dissolved in argon-purged HPLC grade water (2.0 mL) and the pH of the reaction mixture was increased to 7 using argon purged sodium bicarbonate. A solution of disulfide activated-Tubulysin B, supplied by ENDOCYTE, (Compound 11, 1.86 mg, 0.018 mmol) in THF (0.5 mL) was then added to the reaction mixture. The progress of the reaction was monitored using analytical LCMS, and after stirring for 30 min, the reaction was found to reach completion. Conjugate 12 was purified by reverse-phase HPLC [A=2 mM ammonium acetate buffer (pH 7.0), B=CH<sub>3</sub>CN, solvent gradient: 0% B to 100% B in 30 min] to yield the requisite product. LRMS-LC/MS (m/z): [M+H]<sup>+</sup> calculated for C<sub>79</sub>H<sub>119</sub>F<sub>3</sub>N<sub>14</sub>O<sub>25</sub>S<sub>5</sub>, 1881.70; found, 1881.5.

Example 10

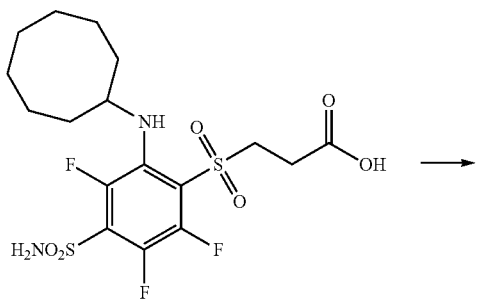

3

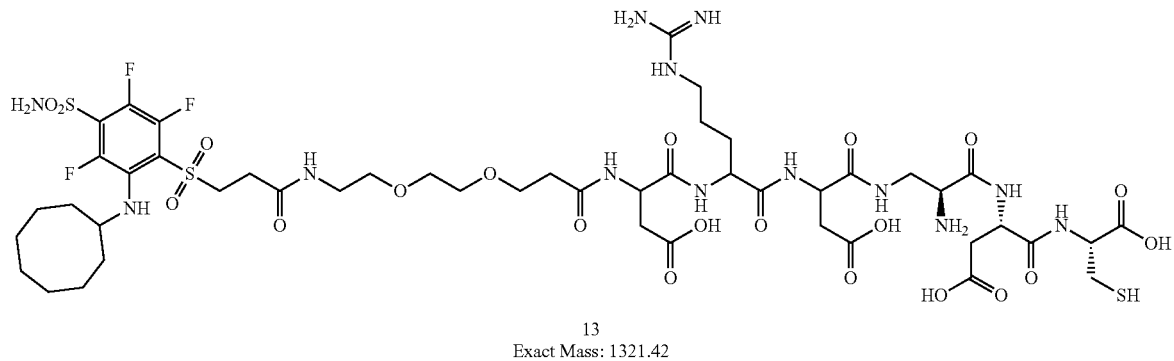

13
Exact Mass: 1321.42

Synthesis of (2R,5S,8S)-8-amino-5,12-bis(carboxymethyl)-18-(3-(2-(2-(3-((2-(cyclooctylamino)-3,5,6-trifluoro-4-sulfamoylphenyl)sulfonyl)propanamido)ethoxy)ethoxy)propanamido)-15-(3-guanidinopropyl)-2-(mercaptomethyl)-4,7,11,14,17-pentaoxo-3,6,10,13,16-pentaazaicosanedioic acid, 13

Compound 13 was synthesized by the following solid phase methodology. H-Cys(Trt)-2-chlorotrityl resin (100 mg, 0.64 mmole/g) was swollen with 3 mL of dichloromethane (DCM) followed by 3 mL of dimethylformamide (DMF). After swelling the resin in DMF, a solution of Fmoc-Asp(tBu)-OH (52.7 mg, 0.128 mmoles), 1-[Bis(dimethylamino)methylene]-1H-1,2,3-triazolo[4,5-b]pyridinium 3-oxid hexafluorophosphate (60.8 mg, 0.16 mmoles) and N,N-diisopropylethylamine (0.056 ml, 0.32 mmoles) in DMF (3 mL) was added. Argon was bubbled for 2 h, and resin was washed three times with 3 mL of DMF and 3 times with 3 mL i-PrOH. The fmoc was removed with a piperidine solution (20% in DMF, 3×5 ml) and the resin was washed three times with 3 mL of DMF and three times with 3 mL i-PrOH. The same protocol was followed for the remaining steps. Compound 13 was cleaved from the resin using a mixture of trifluoroacetic acid:triisopropylsilane:H$_2$O:ethanedithiol (95:2.5:2.5:2.5) and concentrated under vacuum. The concentrated product was precipitated in diethyl ether and dried under vacuum. Crude conjugate was purified by reverse-phase HPLC [A=2 mM ammonium acetate buffer (pH 7.0), B=CH$_3$CN, solvent gradient: 0% B to 100% B in 30 min] to yield the product as a clear oil (62%). LRMS-LC/MS (m/z): [M+H]$^+$ calculated for C$_{48}$H$_{74}$F$_3$N$_{13}$O$_{21}$S$_3$, 1322.42; found, 1322.38. Note that Compound 13 not only serves as a precursor for Conjugate 14, but also is itself designed as a chelator of $^{99m}$Tc and may be used for SPECT/CT imaging applications as Conjugate 13.

Example 11

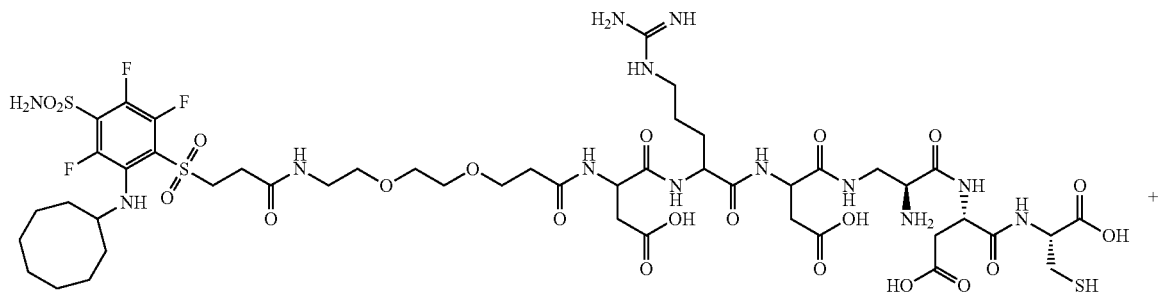

13

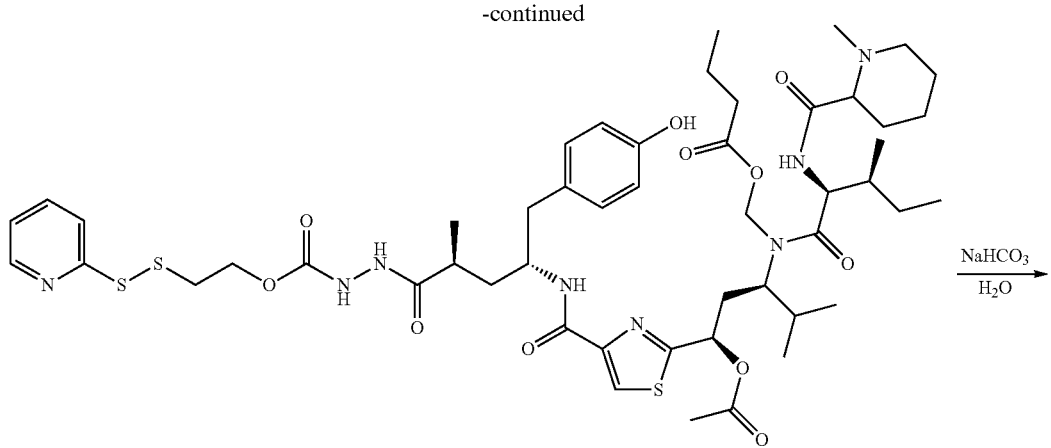

11

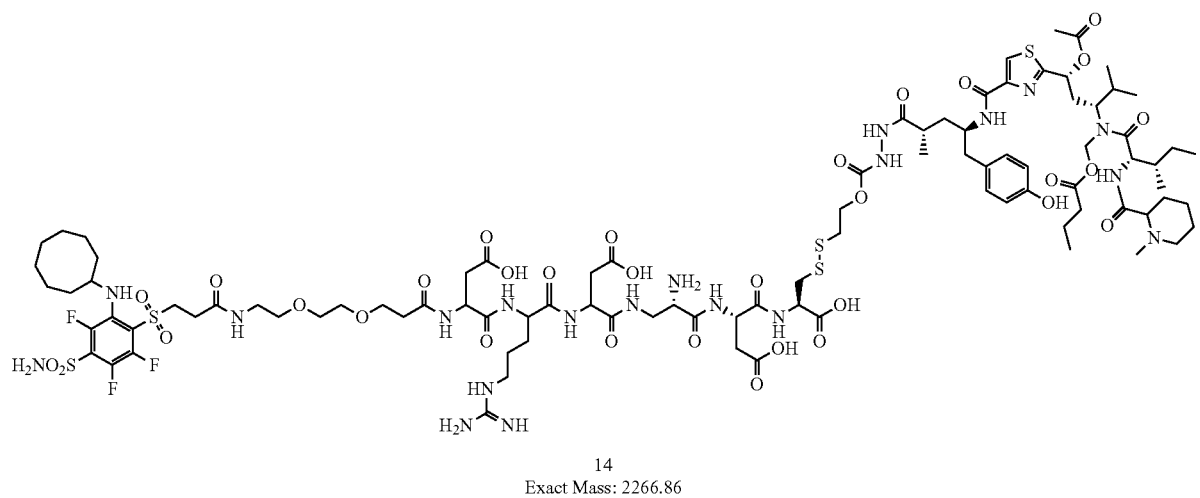

14
Exact Mass: 2266.86

Synthesis of (2R,5S,8S)-2-((11S,13R)-15-(2-((1R,3R)-1-acetoxy-3-((2S,3S)—N-((butyryloxy)methyl)-3-methyl-2-(1-methylpiperidine-2-carboxamido)pentanamido)-4-methylpentyl)thiazol-4-yl)-13-(4-hydroxybenzyl)-11-methyl-7,10,15-trioxo-6-oxa-2,3-dithia-8,9,14-triazapentadecyl)-8-amino-5,12-bis(carboxymethyl)-18-(3-(2-(2-(3-((2-(cyclooctylamino)-3,5,6-trifluoro-4-sulfamoylphenyl)sulfonyl)propanamido)ethoxy)ethoxy)propanamido)-15-(3-guanidinopropyl)-4,7,11,14,17-pentaoxo-3,6,10,13,16-pentaazaicosanedioic acid, 14

A solution of saturated sodium bicarbonate (10 mL) in distilled water was bubbled with argon continuously for 30 minutes (min). Compound 13 (1.2 mg, 0.0009 mmol) was dissolved in argon-purged HPLC grade water (2.0 mL) and the pH of the reaction mixture was increased to 7 using argon purged sodium bicarbonate. A solution of disulfide activated-Tubulysin B, supplied by ENDOCYTE, (Compound 11, 1.27 mg, 0.0012 mmol) in THF (0.5 mL) was then added to the reaction mixture. The progress of the reaction was monitored using analytical LCMS, and after stirring for 30 min, the reaction was found to reach completion. Conjugate 14 was purified by reverse-phase HPLC [A=2 mM ammonium acetate buffer (pH 7.0), B=CH$_3$CN, solvent gradient: 0% B to 100% B in 30 min] to yield the requisite product. LRMS-LC/MS (m/z): [M+H]$^+$ calculated for C$_{93}$H$_{141}$F$_3$N$_{20}$O$_3$S$_5$, 2267.86; found, 1134.57 (half mass).

Example 12

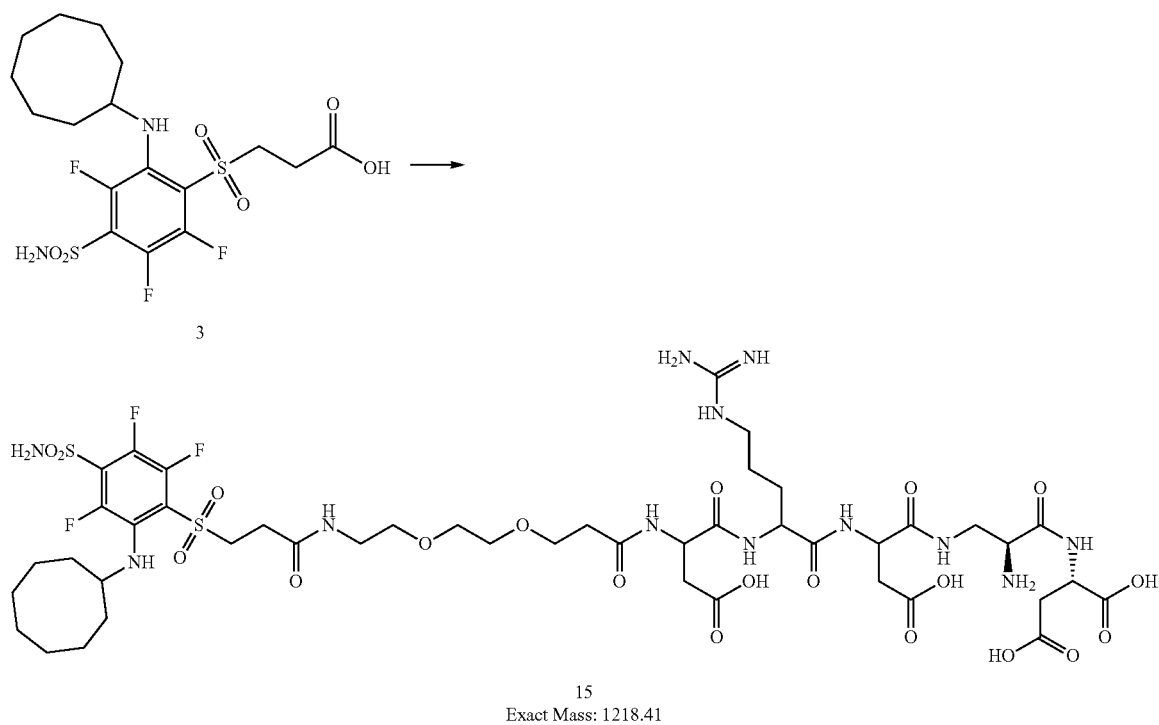

Synthesis of ((2S)-2-amino-3-(3-carboxy-2-(2-(3-carboxy-2-(3-(2-(2-(3-((2-(cyclooctylamino)-3,5,6-trifluoro-4-sulfamoylphenyl)sulfonyl)propanamido)ethoxy)ethoxy)propanamido)propanamido)-5-guanidinopentanamido)propanamido)propanoyl)-L-aspartic acid, 15

Compound 15 was synthesized by the following solid phase methodology. H-Cys(Trt)-2-chlorotrityl resin (100 mg, 0.64 mmole/g) was swollen with 3 mL of dichloromethane (DCM) followed by 3 mL of dimethylformamide (DMF). After swelling the resin in DMF, a solution of Boc-DAP(Fmoc)-OH (54.6 mg, 0.128 mmoles), 1-[Bis(dimethylamino)methylene]-1H-1,2,3-triazolo[4,5-b]pyridinium 3-oxid hexafluorophosphate (60.8 mg, 0.16 mmoles) and N,N-diisopropylethylamine (0.056 ml, 0.32 mmoles) in DMF (3 mL) was added. Argon was bubbled for 2 h, and resin was washed three times with 3 mL of DMF and 3 times with 3 mL i-PrOH. The fmoc was removed with a piperidine solution (20% in DMF, 3×5 ml) and the resin was washed three times with 3 mL of DMF and three times with 3 mL i-PrOH. The other residues were added in using the same stoichiometry. Compound 15 was cleaved from the resin using a mixture of trifluoroacetic acid:triisopropylsilane:$H_2O$:ethanedithiol (95:2.5:2.5:2.5) and concentrated under vacuum. The concentrated product was precipitated in diethyl ether and dried under vacuum. Crude conjugate was purified by reverse-phase HPLC [A=2 mM ammonium acetate buffer (pH 7.0), B=$CH_3CN$, solvent gradient: 0% B to 100% B in 30 min] to yield the product as a clear oil (62%). LRMS-LC/MS (m/z): [M+H]$^+$ calculated for $C_{45}H_{69}F_3N_{12}O_{20}S_2$, 1219.41; found, 1219.09. Note that Compound 15 serves as competitor for Conjugate 14 in competition experiments.

Example 13

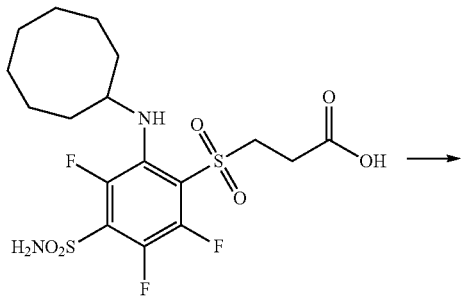

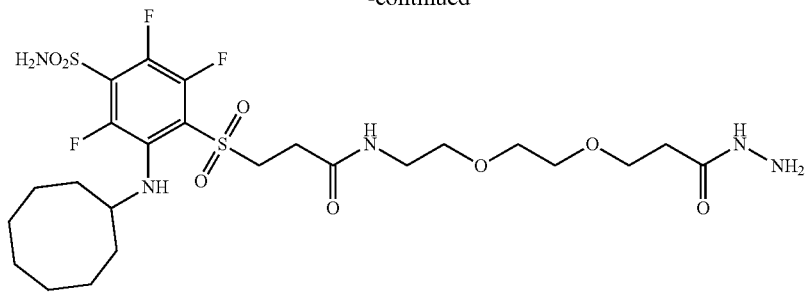

16

N-(2-Aminoethyl)-3-(2-(2-(3-((2-(cyclooctylamino)-3,5,6-trifluoro-4-sulfamoylphenyl)sulfonyl)propanamido)ethoxy)ethoxy)propanamide (16)

N-(2-Aminoethyl)-3-(2-(2-(3-((2-(cyclooctylamino)-3,5,6-trifluoro-4-sulfamoylphenyl)sulfonyl)propanamido)ethoxy)ethoxy)propanamide was synthesized by the following solid phase methodology: After swelling the 1,2-diaminoethane trityl polystyrene resin (100 mg, 1.7 mmol/g) with DMF (3 mL) and DCM (3 mL), a solution of 1-(9H-fluoren-9-yl)-3-oxo-2,7,10-trioxa-4-azatridecan-13-oic acid (136 mg, 0.34 mmol), HATU (162 mg, 0.43 mmol) and DIPEA (0.09 mL, 0.51 mmol) in DMF (3 mL) was added. The reaction mixture was bubbled with argon for 2 h, and resin was washed with DMF (3×3 mL) and DCM (3×3 mL). The Fmoc was removed with a piperidine solution (20% in DMF, 3×5 mL) and the resin was washed with DMF (3×3 mL) and DCM (3×3 mL). A solution of 3-((2-(cyclooctylamino)-3,5,6-trifluoro-4-sulfamoylphenyl)sulfonyl)propanoic acid (179 mg, 0.425 mmol), HATU (162 mg, 0.43 mmol) and DIPEA (0.09 mL, 0.51 mmol) in DMF was added. Argon was bubbled for 2 h, and resin was washed DMF (3×3 mL) and DCM (3×3 mL). N-(2-Aminoethyl)-3-(2-(2-(3-((2-(cyclooctylamino)-3,5,6-trifluoro-4-sulfamoylphenyl)sulfonyl)propanamido)ethoxy)ethoxy) propanamide was cleaved from the resin using a TFA:TIPS:H₂O:EDT cocktail (95:2.5:2.5:2.5) and concentrated under vacuum. The concentrated product was precipitated in diethyl ether and dried under vacuum. Crude conjugate was purified by reverse-phase HPLC [A=2 mM ammonium acetate buffer (pH 7.0), B=CH₃CN, solvent gradient: 0% B to 40% B in 30 min] to yield the product as a white solid. LRMS-LC/MS (m/z): 674.3 [M+H]⁺.

Example 14

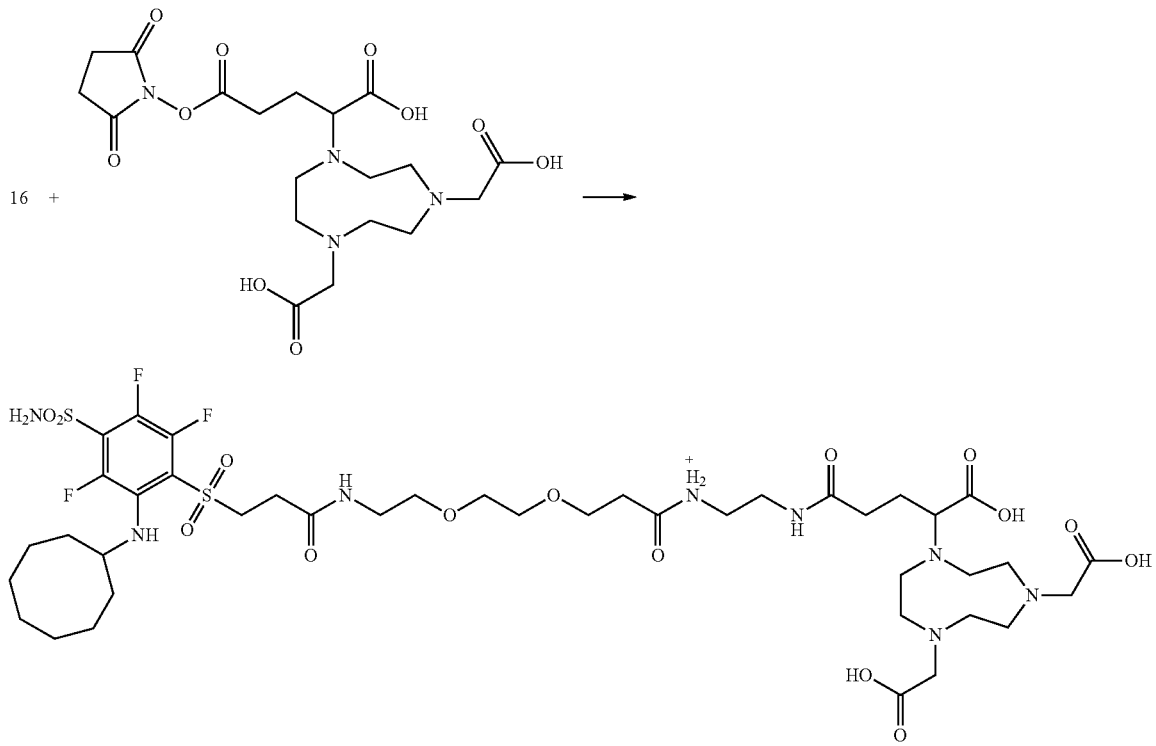

17

2,2'-(7-(21-Carboxy-1-((2-(cyclooctylamino)-3,5,6-trifluoro-4-sulfamoylphenyl)sulfonyl)-3,13,18-trioxo-7,10-dioxa-4,14,17-triazahenicosan-21-yl)-1,4,7-triazonane-1,4-diyl)diacetic acid To a solution of N-(2-Aminoethyl)-3-(2-(2-(3-((2-(cyclooctylamino)-3,5,6-trifluoro-4-sulfamoylphenyl)sulfonyl)propanamido)ethoxy)ethoxy)propanamide (3 mg, 0.003 mmol) in DMF (1 mL) was added 2,2'-(7-(1-carboxy-4-((2,4-dioxopyrrolidin-1-yl)oxy)-4-oxobutyl)-1,4,7-triazonane-1,4-diyl)diacetic acid (NODAGA-NHS, 1.4 mg, 0.009 mmol) and DIPEA (0.0016 mL, 0.034 mmol) and stirred for 1 hour at room temperature. The crude reaction mixture was purified reverse-phase HPLC [A=2 mM ammonium acetate buffer (pH 7.0), B=$CH_3CN$, solvent gradient: 0% B to 20% B in 30 min] to yield the product, Conjugate 17, as a white powder (83% yield). LRMS-LC/MS (m/z): 1031.5 $[M+H]^+$.

Example 15

General Procedure for Radiolabeling of Conjugate 17 with $^{64}Cu$

Radiolabeling was carried out using $^{64}CuCl_2$ in 0.1 N HCl by mixing it with a 50-fold excess of Conjugate 17 in a sodium acetate buffer (pH 10.5) and incubating at room temperature for a minimum of 15 minutes prior to use. To assess the radiochemical purity of the chelation, the solution was analyzed using an Agilent 1260 Infinity II equipped with a LabLogic Flow-RAM radio-HPLC detector with Laura Academia software using the C18 column using the following method: solvent A=0.1% TFA, solvent B=ACN, solvent gradient: 0% B to 100% B in 15 min]. After verification that the radiochemical purity was >95%, the radiolabeled conjugate was used without purification after diluting into the appropriate solvent (cell culture media for in vitro experiments) and (PBS, pH 7.4 for in vivo experiments).

TABLE 1

Exemplary Chelation Conditions of FBSA-NODAGA with Copper-64

| Concentration | <100 μM |
|---|---|
| Buffer | Acetate Buffer (0.5 mM, pH 10.5) |
| Temperature | Room Temperature |
| Time | >10 min |

In Vitro Experiments
Cell Lines and Cell Culture

A549, HT29, and SKRC52 cells were cultured at 37° C. in a humidified, 5% $CO_2$ atmosphere using RPMI-1640 medium containing 10% heat-inactivated fetal bovine serum and 1% penicillin streptomycin.

Example 16

Fluorescent Microscopy of FBSA-$PEG_2$-FITC Conjugate, Conjugate 5.

Metastatic Human Renal Cell Carcinoma (SKRC52) cells ($10^5$) were seeded into chambered coverglass plates and allowed to grow to confluence over 24 hours (hr). Spent medium was replaced with 0.5 mL of fresh medium containing 10% fetal bovine serum albumin and 25 nM concentration of the FITC conjugate, Conjugate 5, alone or the dye conjugate plus 100-fold excess CAIX inhibitor (Compound 3, 3-((2-(cyclooctylamino)-3,5,6-trifluoro-4-sulfamoylphenyl)sulfonyl)propanoic acid). After incubation for 1 hour at 37° C., cells were rinsed twice with 1 mL of media to remove unbound fluorescence and 0.5 ml of fresh incubation medium was added to the wells. Images were acquired using a confocal microscopy (FV 1000, Olympus). Results are shown in FIG. 1. The FITC Conjugate 5 bound the cells and were competed in the presence of excess unconjugated inhibitor, indicating a specific receptor-specific binding event.

Example 17

General Procedure for Binding Affinity Determination of CAIX FITC Conjugates

HEK293 transfected with CAIX, SKRC52, HT29, or A549 cells ($0.25 \times 10^6$) were placed into 1.5 ml centrifuge tubes with 0.3 mL of fresh DMEM medium containing increasing concentrations of CAIX FITC conjugates in the presence or absence of 100-fold excess CAIX inhibitor (Compound 3, 3-((2-(cyclooctylamino)-3,5,6-trifluoro-4-sulfamoylphenyl)sulfonyl)propanoic acid. After incubating for 1 h at 25° C., cells were rinsed twice with 1 mL of medium. The cells were transferred into a 96-well plate and the mean florescence intensity (MFI) was read using flow cytometry (BD Accuri C6, BD Biosciences). Apparent $K_D$ was calculated by plotting MFI versus the concentration of the FITC conjugates using GraphPad Prism 4. For hypoxia experiments, cells were incubated under an atmosphere containing 1% oxygen, 5% carbon dioxide, and 94% nitrogen for 24-48 hours in a hypoxia chamber. Results of binding affinity for CAIX FITC are shown in Table 2.

TABLE 2

Binding affinity of CAIX FITC conjugates in HEK293 transfected with CAIX or SKRC52.

| Linker | Approximate Linker Length (Å) | Binding Affinity in SKRC52 (nM) | Binding Affinity in HEK293-CAIX (nM) |
|---|---|---|---|
| $PEG_2$ (Conjugate 5) | 20 | 1.28 | 17.94 |
| $PEG_4$ (Conjugate 7) | 40 | 4.57 | 55.2 |
| Ethylene diamine (ED, Conjugate 9) | 5 | 40.89 | 215.7 |

Example 18

Figure 8:
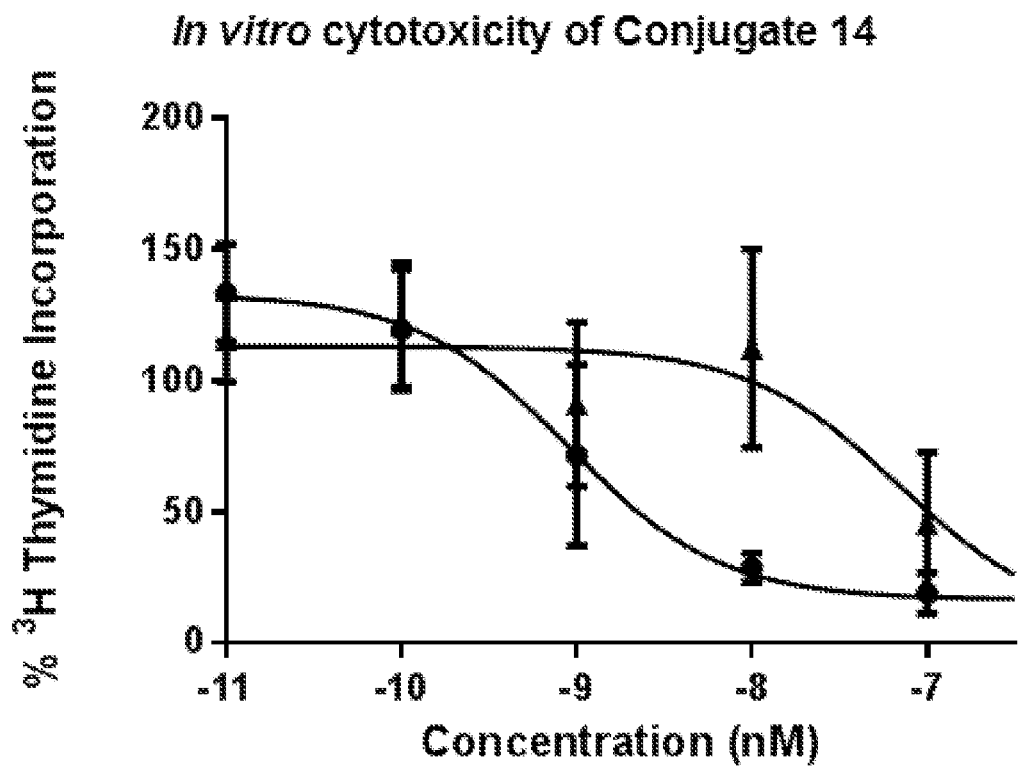
FIG. 8 shows in vitro cytotoxicity of Conjugate 14 wherein various concentrations of Conjugate 14 were incubated with HEK or HEK-CA9 cells for 4 hours. After washing, the cells were incubated for 66-72 hours and their viability was determined via $^3$H-thymidine uptake. (●) HEK293-CA9; (▲) HEK293.

General Procedure for In Vitro Cytotoxicity Determination by $^3H$-Thymidine Uptake Assays HT-29 cells were seeded on amine-coated 24-well plates and allowed to form monolayers. The spent medium in each well was replaced with fresh medium (0.5 mL) containing various concentrations of Conjugate 12. After incubating for 2 hr at 37° C., cells were rinsed three times with fresh medium and then incubated an additional 66 hr at 37° C. in fresh medium. Spent medium in each well was again replaced with fresh medium (0.5 mL) containing $^3H$-thymidine (1 μCi/ml) and the cells were incubated for an additional 4 hr. After washing the cells three times with medium, they were dissolved in 0.5 mL of 0.25 M NaOH. Thymidine incorporation was then determined by counting cell-associated radioactivity using a scintillation counter (PACKARD, PACKARD INSTRUMENT COMPANY). The $IC_{50}$ value was derived from a plot of the percent of $^3H$-thymidine incorporation versus log concentration using Graph Pad Prism 4 and TABLECURVE 2D software. Results are shown in FIG. 8, and show that the $IC_{50}$ for the conjugate was 5.045 nM.

Example 19

In Vitro Binding Affinity of Radiolabeled Conjugate 17

SKRC52, HT29, A549 cells (~0.25×10$^6$) were seeded in a 24-well plate and allowed to grow overnight. Fresh medium containing increasing concentrations of radiolabeled Conjugate 17, as prepared in Example 17, in the presence or absence of 100-fold excess FBSA competition compound was added. All concentrations were examined in duplicate or triplicate. After incubating for 1 h at 25° C., cells were washed with PBS (3×0.5 mL). To each well was added 0.5 M NaOH. After 10 min, 0.45 mL of the NaOH was removed and the radioactivity was measured with a γ-counter (Packard, Packard Instrument Company). The apparent binding affinity was calculated by plotting the bound radioactivity versus the concentration of the radiolabeled conjugate with GraphPad Prism 4.

Figure 9:
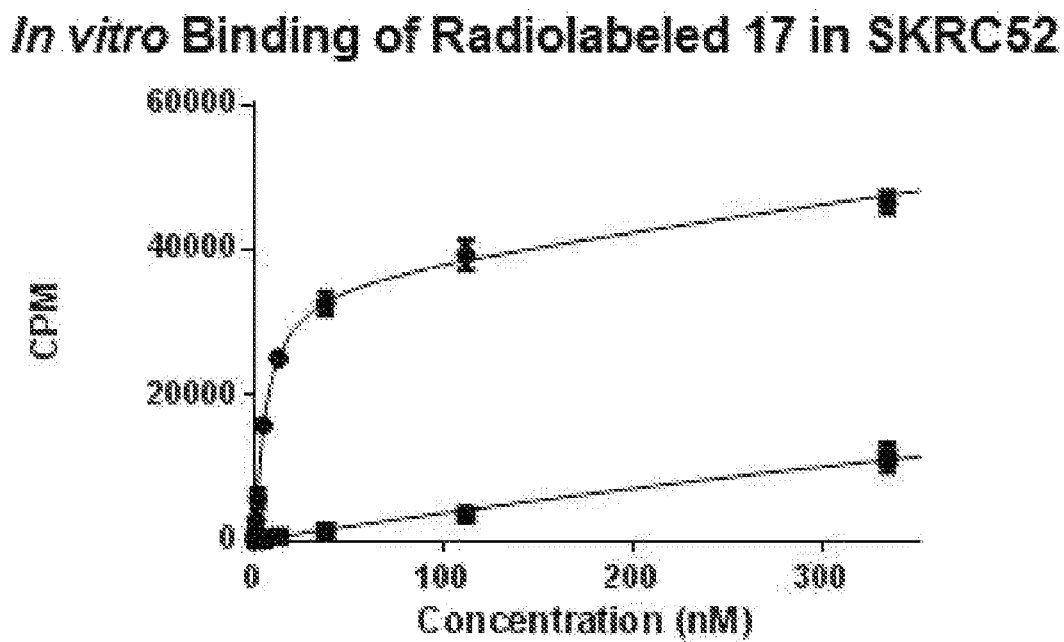
FIG. 9 shows in vitro binding of radiolabeled conjugate 17 in SKRC52 cells. (●) Conjugate 17, $K_D$=5.87 nM; (■) Competition.
Figure 10:
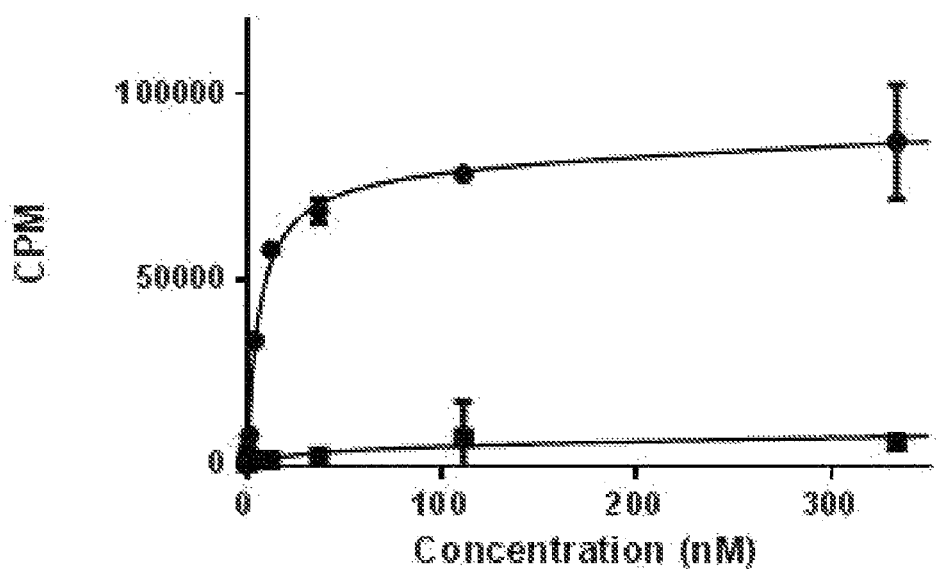
FIG. 10 shows in vitro binding of radiolabeled conjugate 17 in A549 Cells. (●) Conjugate 17, $K_D$=6.04 nM; (■) Competition.

As can be seen in FIGS. 9 and 10, the apparent binding affinity of radiolabeled 17 was established using SKRC52 and A549 cells as a low nM value ($K_D$=5.87 nM in SKRC52, and $K_D$=6.04 nM in A549), and reaching saturation at approximately 75 nM. The competition controls (cells treated with increasing concentrations of radiolabeled Conjugate 17 with 100-fold excess of the competition ligand which was unlabeled FBSA-COOH) showed significantly less bound radioactivity. Without being bound by theory, it appears that the binding of radiolabeled 17 to the cells was a receptor-specific event.

In Vivo Experiments
Animal Husbandry

Athymic nu/nu mice were purchased from Harlan Laboratories (ENVIGO), housed in a sterile environment on a standard 12 hour light-dark cycle and maintained on normal rodent chow. All animal procedures were approved by the PURDUE Animal Care and Use Committee in accordance with National Institutes of Health guidelines.

Example 20

In Vivo Efficacy of Tubulysin Conjugate 12 in HT29 Xenograft Tumors.

Figure 11:
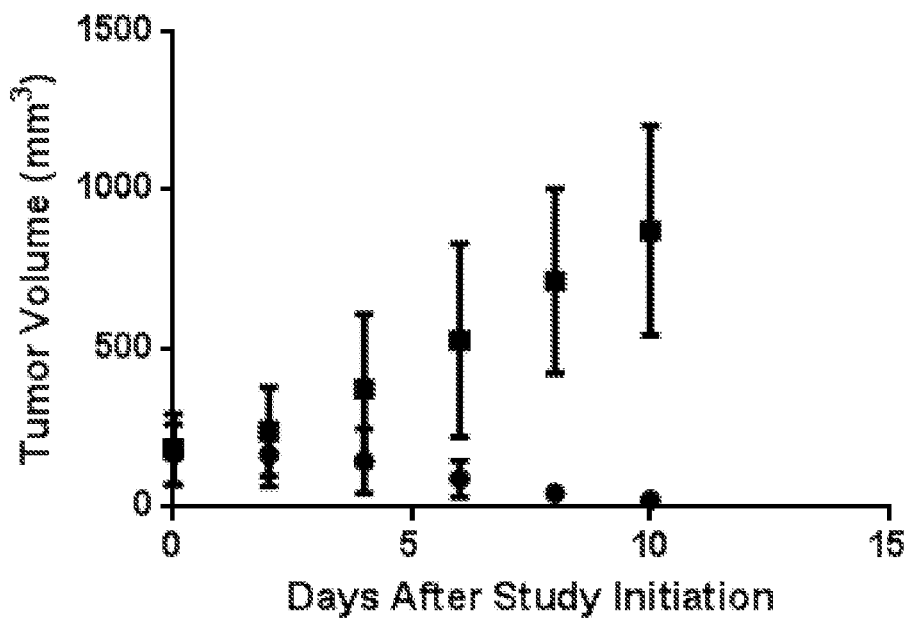
FIG. 11 shows the in vivo efficacy of Conjugate 12 (TIW) in HT-29 xenografts (n=3 for Conjugate 12 group and n=2 for competition group), wherein the competition group was treated with 100-fold excess of Compound 3, and the mice treated with 2 umol/kg Conjugate 12 show the tumors shrinking while the untreated controls grow. (●) Conjugate 12; (■) Competition.
Figure 12:
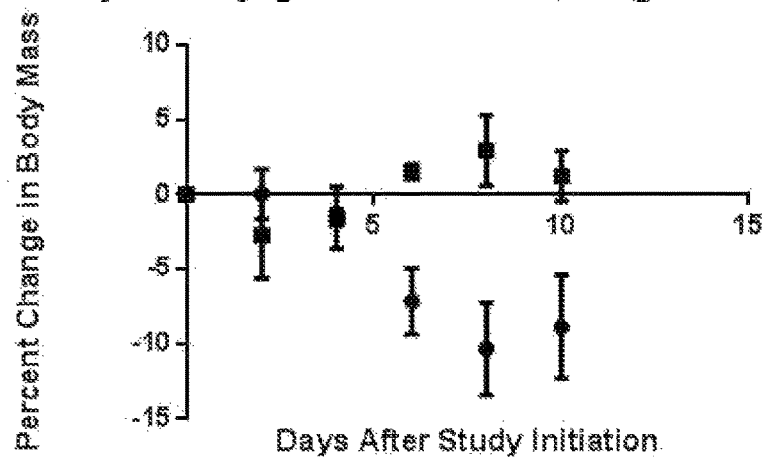
FIG. 12 shows whole body masses of HT-29 xenograft mice treated with Conjugate 12 showing that there was not more than 10 percent body mass loss at 6 days into the treatment. The competition group was treated with 100-fold excess of Compound 3, where n=3 for Conjugate 12 group and n=2 for competition group.
Figure 13:
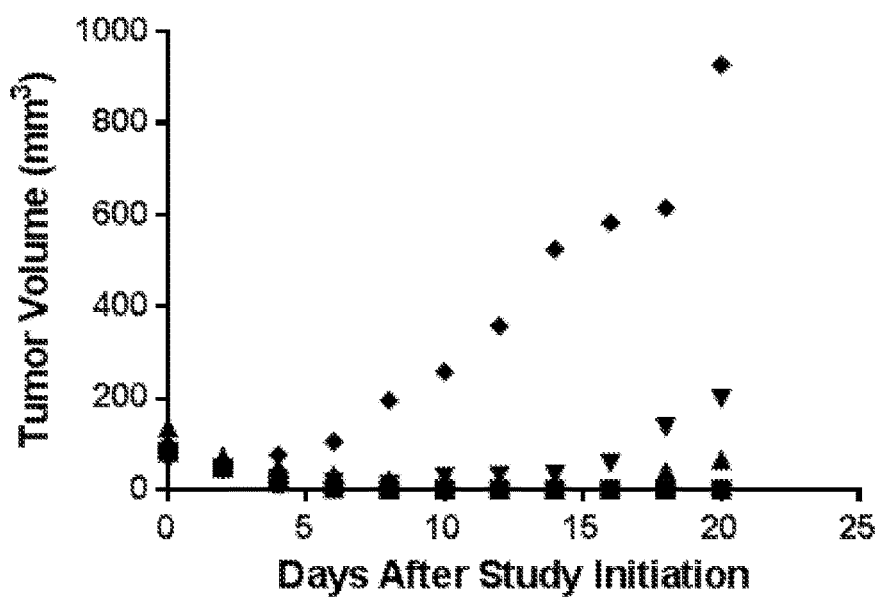
FIG. 13 shows dose escalation in vivo efficacy of Conjugate 14 in HT-29 xenografts (n=1 in for each dose), where after a tumor disappeared, the mice were treated with one additional dose, and the last treatment was Day 6, 8, 12 and 14 for Mouse 1, 2, 3, and 4/5, respectively, doses 2, 1.5, and 1 umole/kg all shrank tumors, but 1 umole/kg showed tumor reemergence starting on day 16. Mouse dose levels: (●) 2 µmole/kg; (■) 1.5 µmole/kg; (▲) 1 µmole/kg; (▼) 0.5 µmole/kg; (♦) 0.25 µmole/kg.
Figure 14:
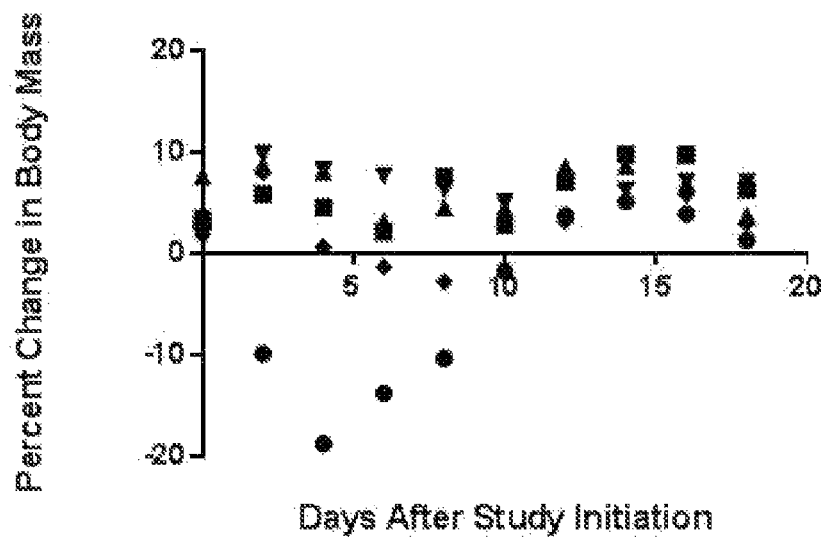
FIG. 14 shows whole body masses of HT-29 xenograft mice treated with various doses of Conjugate 14 (n=1 in for each dose), where the highest dose of Conjugate 14 still showed loss of body mass to Conjugate 12 (FIG. 10) but the other doses show acceptable body mass profiles. Mouse dose levels: (●) 2 µmole/kg; (■) 1.5 µmole/kg; (▲) 1 µmole/kg; (▼) 0.5 µmole/kg; (♦) 0.25 mole/kg.
Figure 15:
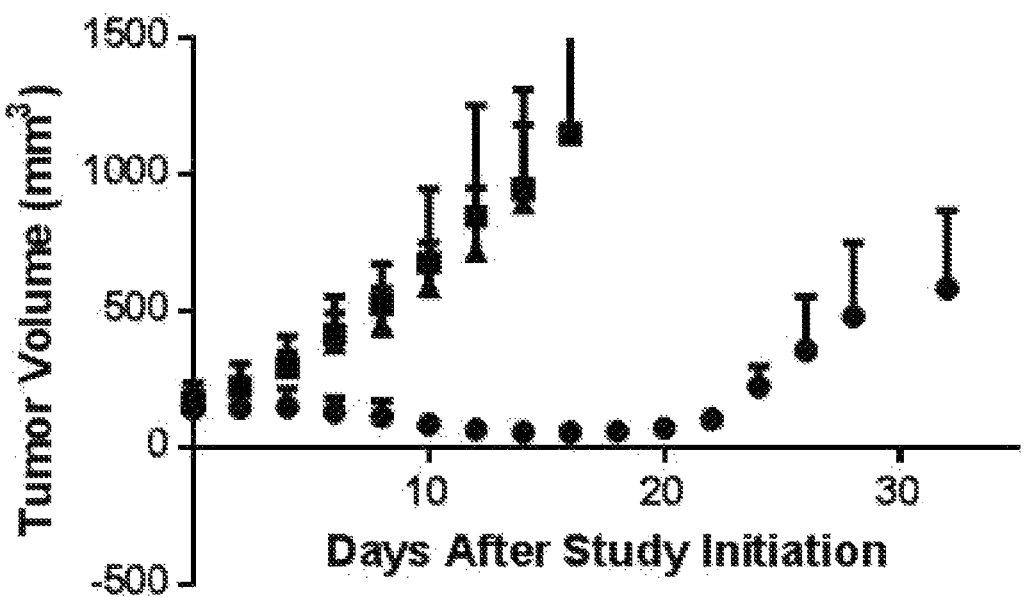
FIG. 15 shows in vivo efficacy of Conjugate 14 in HT-29 xenografts (n=5 in each group), where treatment was administered TIW for three weeks at 1.25 umole/kg of Conjugate 14 and the competition group 1.25 umole/kg of Conjugate 14 with 100-fold excess of Compound 15, where the competition and tumor only group were sacrificed as per the study's humane guidelines on Day 16, and where the treatment group displayed stable tumor regression and stable disease until treatment cessation. (●) Conjugate 14; (■) Competition; (▲) Tumor only.
Figure 16:
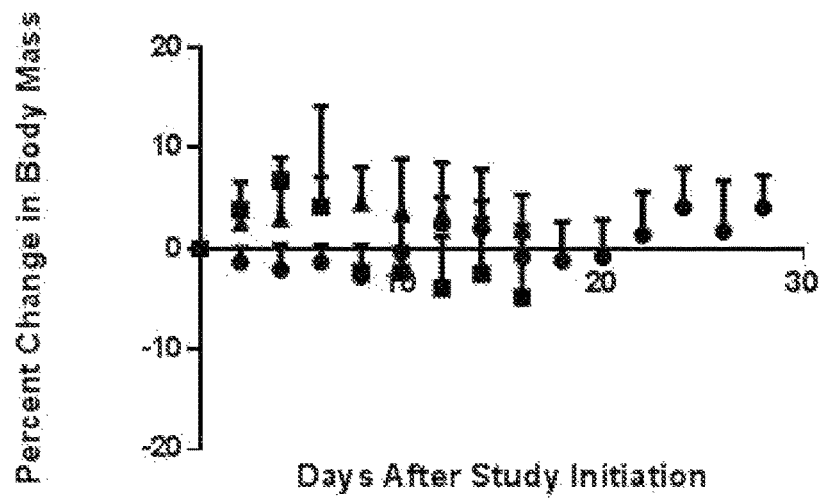
FIG. 16 shows whole body masses of HT-29 xenograft mice treated with 1.25 umole/kg of Conjugate 14 and the competition group 1.25 umole/kg of Conjugate 14 with 100-fold excess of Compound 15. (●) Conjugate 14; (■) Competition; (▲) Tumor only.

Cells, HT-29 cells (4.25×10$^6$) were subcutaneously injected into the shoulders of 5-6 week old female nu/nu mice. Tumors were measured in two perpendicular directions thrice weekly with vernier calipers and their volumes were calculated as 0.5×L×W$^2$, where L is the longest axis (in millimeters), and W is the axis perpendicular to L (in millimeters). Dosing of Conjugate 12 was initiated when the subcutaneous tumors reached ~100-275 mm$^3$ in volume. Dosing solutions were prepared in saline and filtered through a 0.22 μm filter. Solutions were administered via tail vein injection or intraperitoneally. Each mouse received 2 μmol/kg Conjugate 12 per injection. Injections were given every two days and the mice were weighed concurrently. Results are shown in FIGS. 11-12. As shown in FIG. 11, the treatment mice halted tumor growth and the xenograft is in the process of shrinking at the time of this disclosure. In all cases, no gross toxicity was observed and less than 10 percent loss of weight was observed at this dosing level (FIG. 12).

Figure 17:
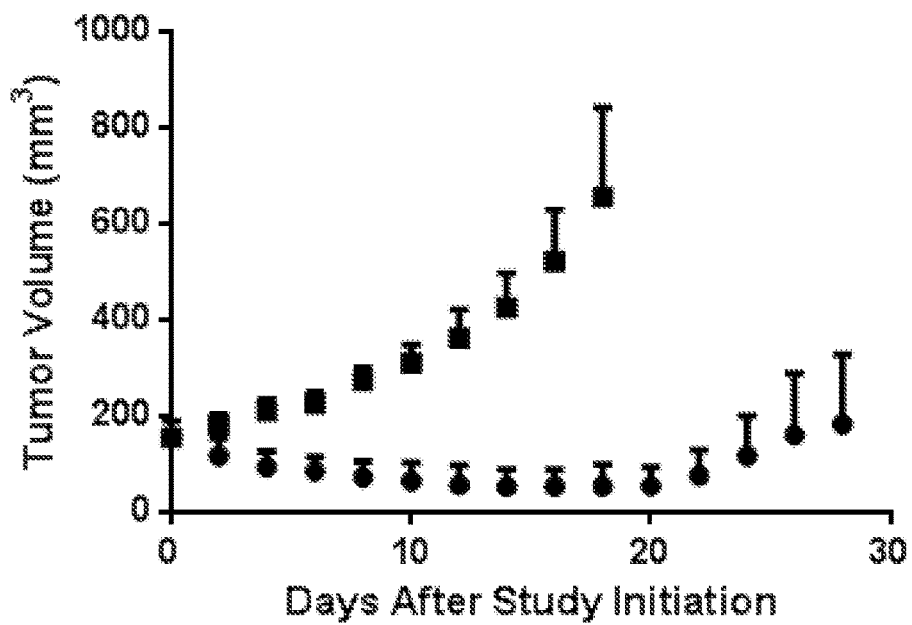
FIG. 17 shows in vivo efficacy of Conjugate 14 in A549 xenografts, where treatment was administered TIW for three weeks at 1.25 umole/kg of Conjugate 14 and the competition group 1.25 umole/kg of Conjugate 14 with 100-fold excess of Compound 15, where the competition and tumor only group were sacrificed as per the study's humane guidelines on Day 16, and where the treatment group displayed stable tumor regression and stable disease until treatment cessation. (♦) Conjugate 14; (■) Competition.
Figure 18:
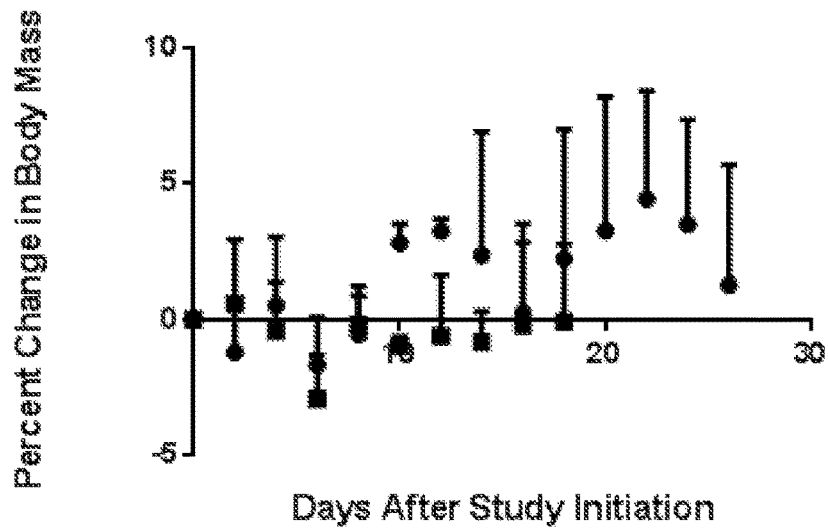
FIG. 18 shows whole body masses of A549 xenograft mice treated with 1.25 umole/kg of Conjugate 14 and the competition group 1.25 umole/kg of Conjugate 14 with 100-fold excess of Compound 15. (●) Conjugate 14; (■) Competition.

Similar experiments were performed using Conjugate 14 instead of Conjugate 12, as shown in FIGS. 13-16. Similar experiments were performed using Conjugate 14 with A549 cells instead of HT-29 cells (FIGS. 17 and 18).

Example 21

Whole-Body Imaging and Biodistribution of Radiolabeled 17 in Mouse Xenograft Models SKRC52, HT29, or A549 cells (~3×10$^6$ cells per mouse) were injected subcutaneously into the shoulders of female athymic nu/nu mice. Growth of the tumors was measured in two perpendicular directions and the volumes of the tumors were calculated as 0.5×L×W$^2$ (L=longest axis and W=axis perpendicular to L in millimeters). Once tumors reached a minimum of 500 mm$^3$ in volume, animals were injected with radiolabeled Conjugate 17 (250 μCi) in PBS (100 μL, pH 7.4) via tail vein injection. To obtain whole-body images, mice were anesthetized with isoflurane and images were acquired with a Kodak Imaging Station (In-Vivo FX, Eastman Kodak Company) in combination with CCD camera and Kodak molecular imaging software (version 4.0) with the kidneys shielded. Radioimages were acquired using the following parameters: radio isotope illumination source, 3 min acquisition time, f-stop=4, focal plane=5, FOV=160, binning=8. White light images were acquired using the following parameters: white light transillumination illumination source, 0.175 s acquisition time, f-stop=16, focal plane=5, FOV=160, and no binning. After acquiring the whole-body imaging, the mice were sacrificed with $CO_2$ asphyxiation and, following necropsy, the tissues were placed into preweighed γ-counter tubes. The radioactivity of the tissues and a fraction of the injected dose was measured in a γ-counter (Packard, Packard Instrument Company). Count per minute (CPM) values were corrected for decay times, and the results were calculated as percent of the injected dose per gram (% ID/g) of wet tissue.

Figure 19:
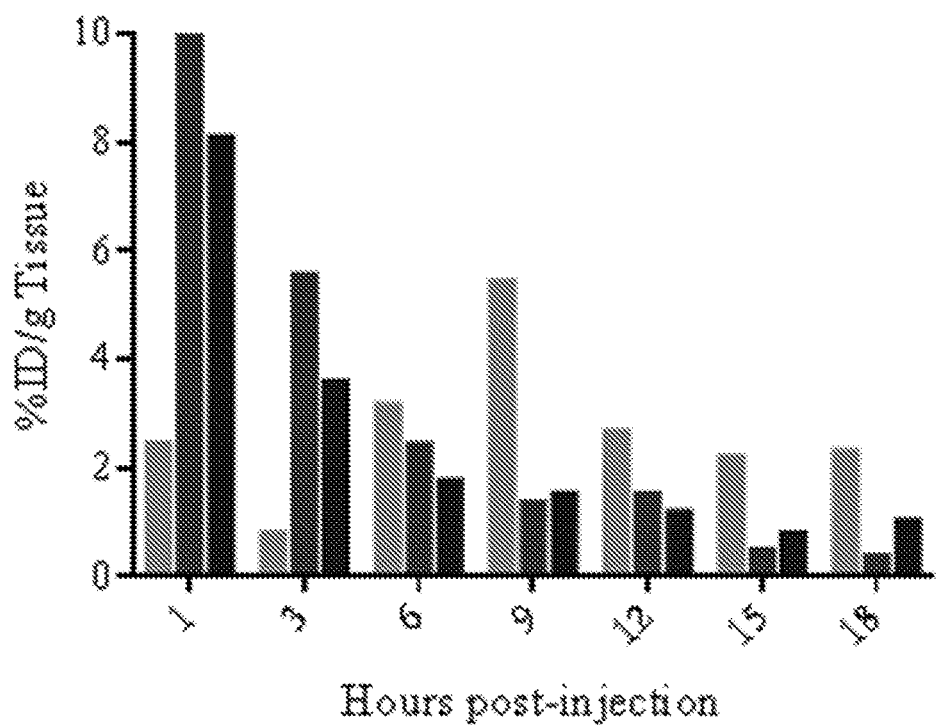
FIG. 19 shows a biodistribution time-course study of radiolabeled Conjugate 17 in mice with A549 xenografts. For each time point post-injection, left bar=tumor; center bar=stomach; right bar=kidney.

250 μCi of radiolabeled Conjugate 17 was injected into the tail vein of mice bearing xenografts derived from the A549 cell line. At various time points shown in Table 3, the tissues were removed from the mice (n=1 per time point), weighed, and the radioactivity was quantified on a gamma counter. Because copper-64 emits gamma radiation at 511 keV in 36% abundance, it is possible to use gamma detection methods. Results are shown in FIG. 19.

TABLE 3

Tumor-to-Tissue Ratios in a Time-Course Study of radiolabeled conjugate 17 in A549 Xengrafts

| Time (hr) | Tumor:Stomach | Tumor:Kidneys |
|---|---|---|
| 1 | 0.1 | 0.3 |
| 3 | 0.1 | 0.2 |
| 6 | 1.3 | 1.8 |
| 9 | 4.0 | 3.6 |
| 12 | 1.8 | 2.3 |
| 15 | 4.5 | 2.8 |
| 18 | 6.3 | 2.2 |

As can be seen in Table 3, initially the uptake of the conjugate was very high in the stomach and kidneys. After six hours post-injection, that the tumor began to show higher tissue uptake than the stomach and kidneys. The highest tumor-to-tissue ratio was shown at nine hours. At all other later times tested, the tumor maintained this higher uptake.

Figure 20:
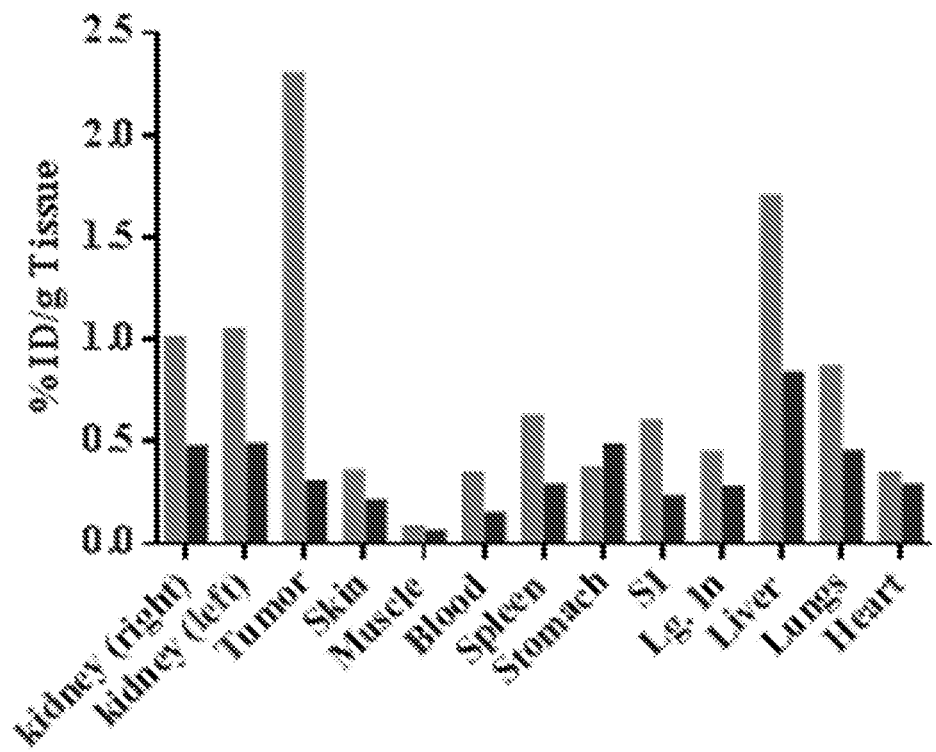
FIG. 20 shows a biodistribution study of radiolabeled Conjugate 17 in an A549 xenograft model. For each tissue type shown in graph, left bar=Conjugate 17; right bar=Competition.

The full tissue biodistribution of radiolabeled Conjugate 17 is shown in FIG. 20 at 18 hours post injection. This experiment was performed at 18 hours primarily for logistical ease after verifying that the tissue uptake values between 6 and 18 hours do not drastically change. The high tumor uptake is still maintained at 18 hours and, most importantly, the competition mouse (mice co-injected with 250 Xi of radiolabeled Conjugate 17+100-fold molar excess of the competition molecule) has a much lower radiation count at the tumor site than the non-competition mouse.

Without being bound by theory, this indicates that radiolabeled Conjugate 17 binds specifically to the tumor cells in a receptor-mediated manner.

Figure 21:
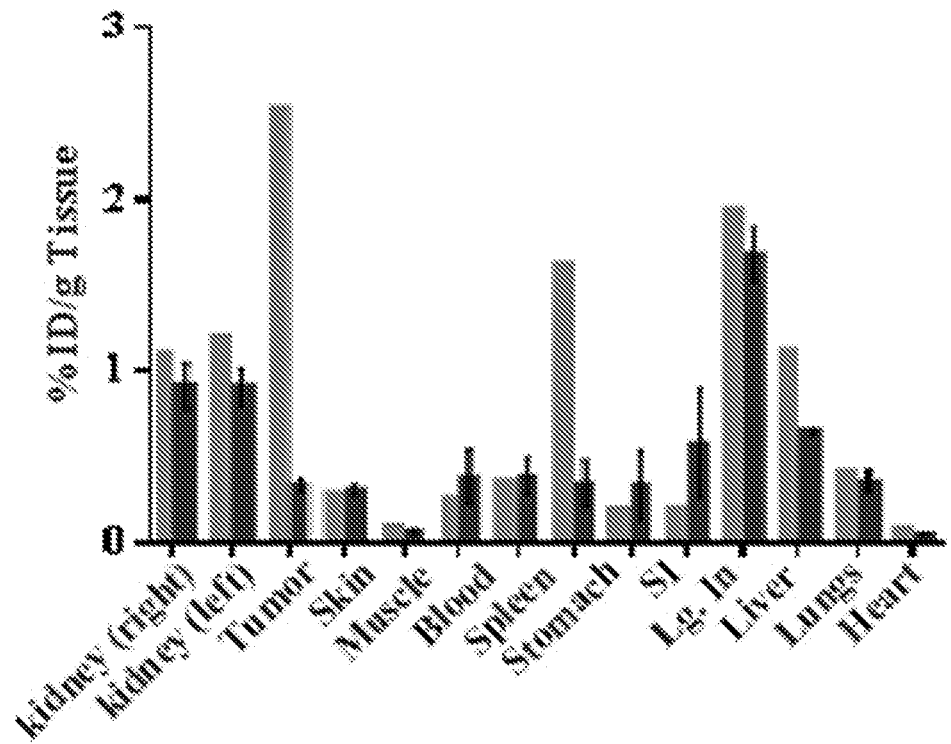
FIG. 21 shows a biodistribution of radiolabeled Conjugate 17 in a SKRC52 xenograft model. For each tissue type shown in graph, left bar=Conjugate 17; right bar=Competition.
Figure 22:
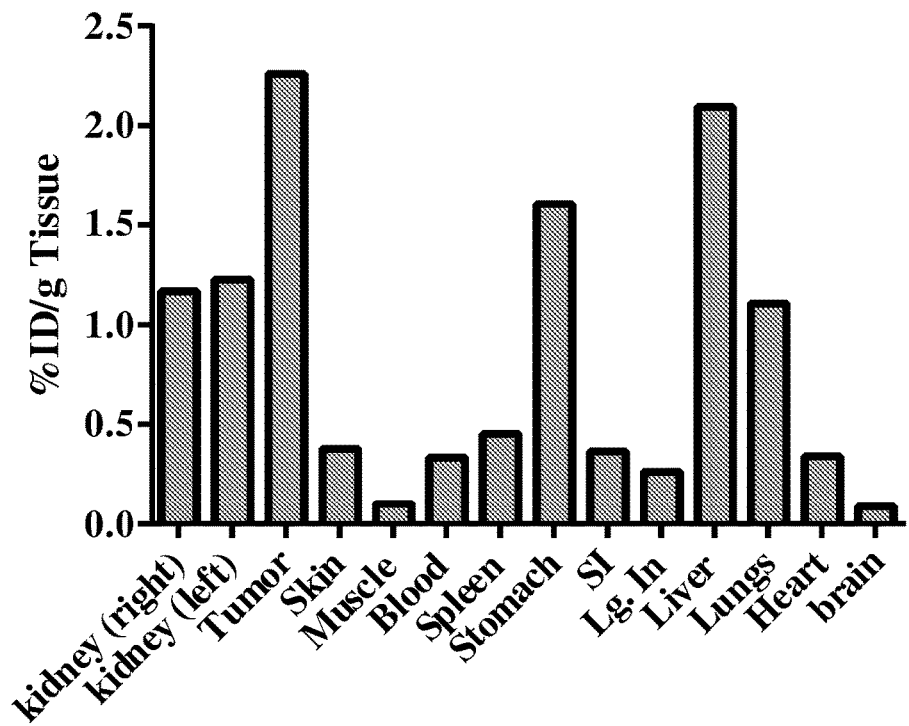
FIG. 22 shows a biodistribution of radiolabeled Conjugate 17 in a HT29 xenograft model.

FIG. 21 and FIG. 22 show the biodistribution data from these experiments using SKRC52 and HT29 xenografts at 18 hours after injection. The SKRC52 experiment was performed with a competition control that indicated the radioactivity at the tumor was receptor mediated. The HT29 xenografts were not tested with the competition control. Because the HT29 cells express many fewer CAIX receptors on the cell surface, the tumor to tissue background ratios are not very good at 18 hours.

Figure 23A:
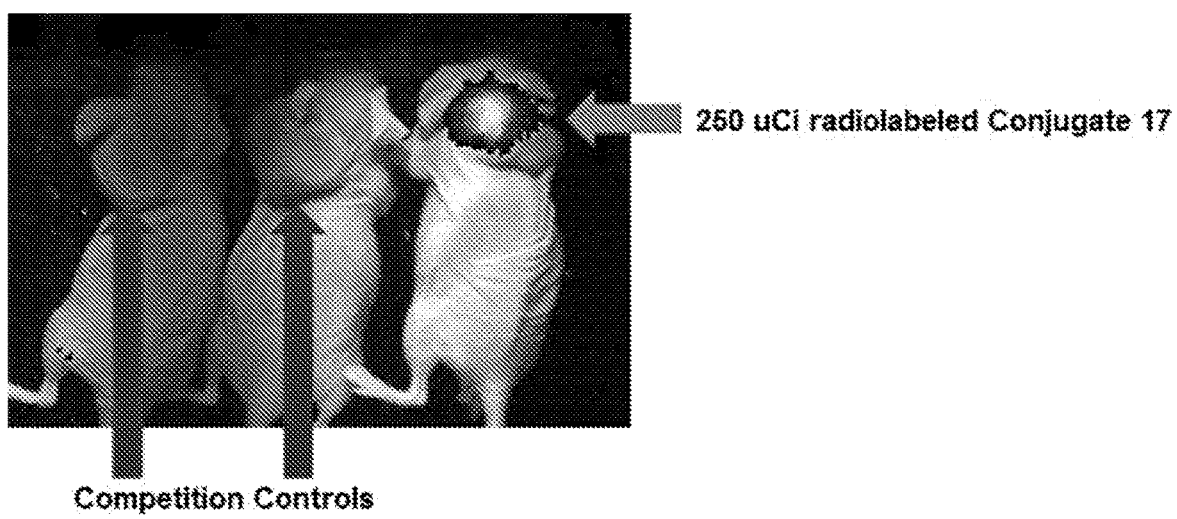
FIGS. 23A and 23B show PET/CT of radiolabeled Conjugate 17 in a SKRC52 xenograft model.
Figure 23B:
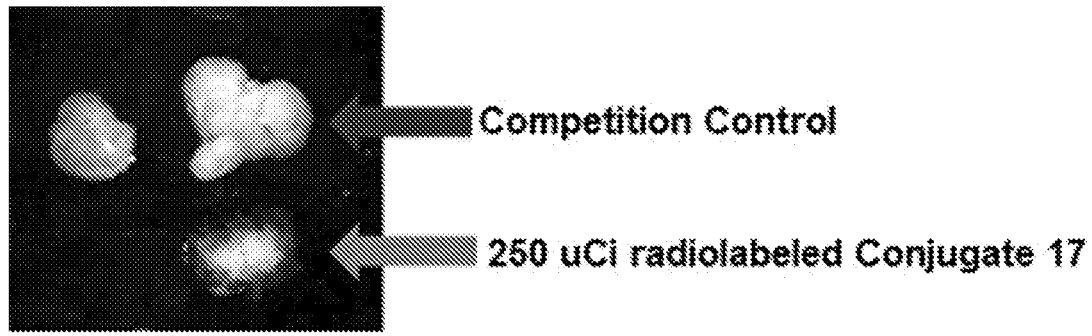

FIGS. 23A and 23B show the whole-body images of mice bearing with CAIX-positive xenografts using after injecting radiolabeled 17. In particular, it shows a competition experiment performed with mice bearing SKRC52 xenografts after injecting 250 µCi of radiolabeled Conjugate 17 and acquiring the whole-body images of the anesthetized mice five hours after injections. In the case of the experiment shown in FIG. 23A, the mouse injected with the targeted PET imaging conjugate shows bright uptake at the tumor site. However the two mice shown on the left injected with 100-fold excess of the competition ligand (FBSA-COOH) in conjugation of the 250 µCi of radiolabeled Conjugate 17 do not exhibit any tumor uptake at the threshold selected for this image. The tumors were removed from the mice and are shown in FIG. 23B, and again show higher tumor uptake in the targeted mouse versus the competition mice.

Figure 24:
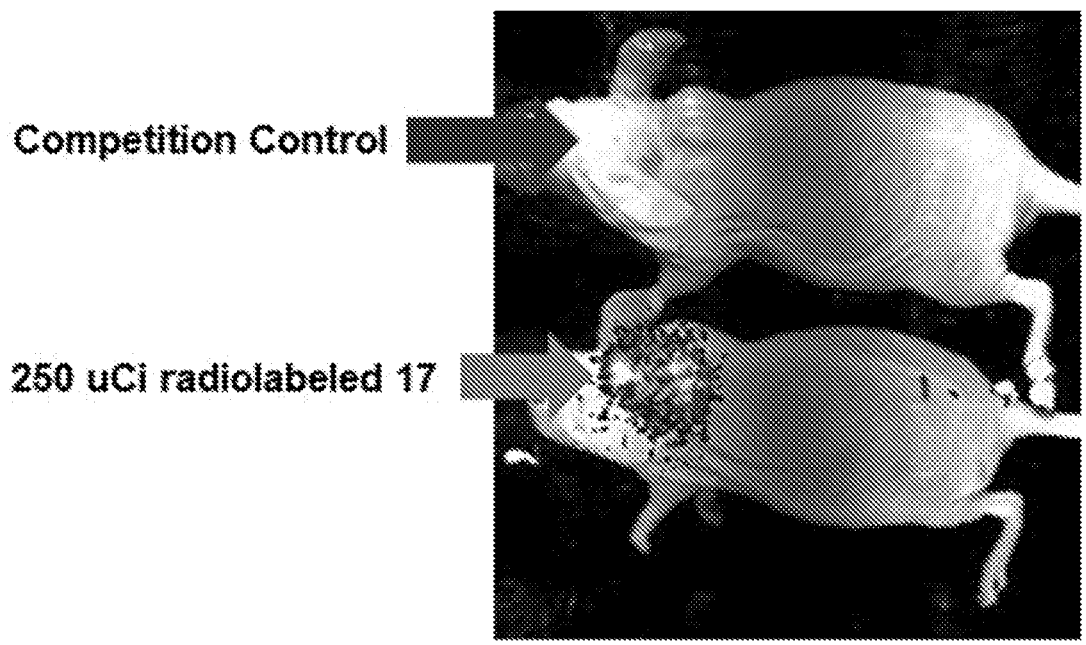
FIG. 24 shows PET/CT of radiolabeled Conjugate 17 in an A549 xenograft model.

The efficacy of radiolabeled Conjugate 17 was also shown in other tumor models using the methods described above, and acquiring the whole-body images. For example, as shown in FIG. 24, the targeted mouse shows much higher tumor uptake than that of the competition mouse. This data was also demonstrated in mice bearing HT29 xenografts (data not shown).

What is claimed is:

1. A conjugate of the formula B-L-A, or a pharmaceutically acceptable salt thereof, wherein B is a carbonic anhydrase IX ligand of the formula

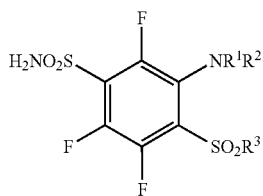

wherein
R$^3$ is C$_1$-C$_{10}$ alkyl substituted with one substituent selected from the group consisting of —C(O)—* and —C(O)N(R$^5$)—*;
each of R$^1$, R$^2$, and R$^5$ is independently selected from the group consisting of H, C$_1$-C$_6$ alkyl, C$_2$-C$_6$ alkenyl, C$_2$-C$_6$ alkynyl, and C$_3$-C$_9$ cycloalkyl;
L is an optional linker;
A is a therapeutic agent or an imaging agent;
m is an integer from 1 to 5; and
* represents a point of attachment to L or A.

2. The conjugate of claim 1, or a pharmaceutically acceptable salt thereof, wherein the carbonic anhydrase IX ligand is

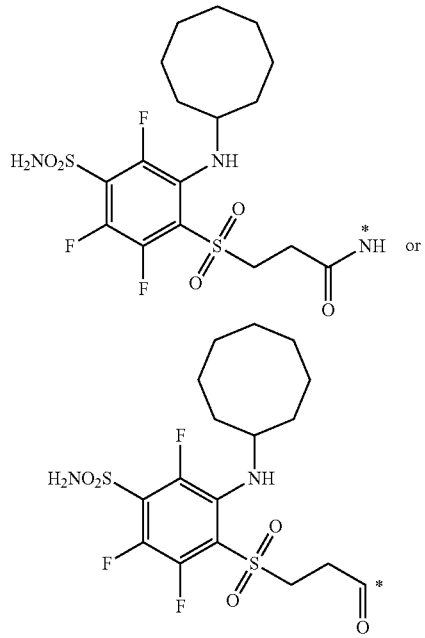

wherein * represents a point of attachment to the rest of the conjugate.

3. The conjugate of claim 2, or a pharmaceutically acceptable salt thereof, wherein the linker comprises a portion selected from the group consisting of —C(O)(C$_1$-C$_{12}$ alkyl)C(O)—, —NH—C$_1$-C$_{12}$ alkyl-NH—, —N(C$_1$-C$_6$ alkyl)-C$_1$-C$_{12}$ alkyl-N(C$_1$-C$_6$ alkyl)-, —C(O)CH$_2$CH$_2$(OCH$_2$CH$_2$)$_q$NH—, —C(O)CH$_2$CH$_2$(OCH$_2$CH$_2$)$_q$N(C$_1$-C$_6$ alkyl)-, —(CH$_2$CH$_2$O)$_q$CH$_2$CH$_2$C(O)—, —NH(CH$_2$CH$_2$O)$_q$CH$_2$CH$_2$C(O)—, and —N(C$_1$-C$_6$ alkyl)(CH$_2$CH$_2$O)$_q$CH$_2$CH$_2$C(O)—; wherein q is an integer from 1 to 40.

4. The conjugate of claim 2, or a pharmaceutically acceptable salt thereof, wherein the linker comprises at least one amino acid selected from the group consisting of 3-aminoalanine, aspartic acid, cysteine, and arginine.

5. The conjugate of claim 1, or a pharmaceutically acceptable salt thereof, wherein the linker comprises a linker portion of the formula

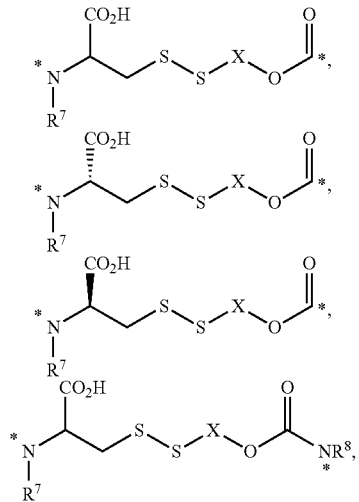

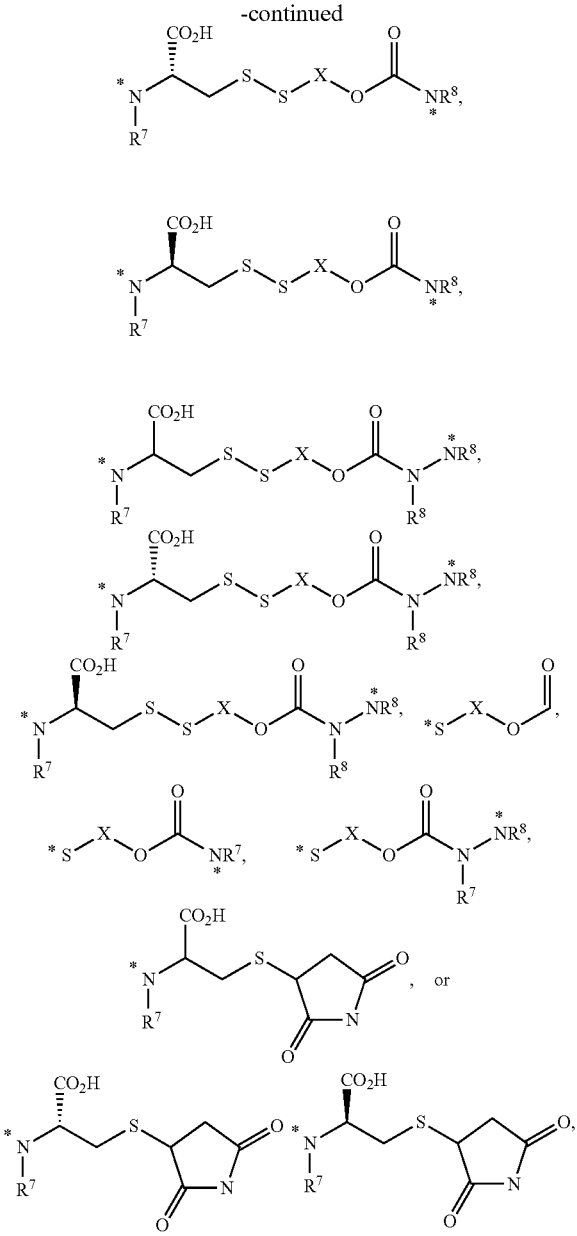

wherein each $R^7$ and $R^8$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$OC(O)NR^9R^{10}$, —$OS(O)R^9$, —$OS(O)_2R^9$, —$SR^9$, —$S(O)R^9$, —$S(O)_2R^9$, —$S(O)NR^9R^{10}$, —$S(O)_2NR^9R^{10}$, —$OS(O)NR^9R^{10}$, —$OS(O)_2NR^9R^{10}$, —$NR^9R^{10}$, —$NR^9C(O)R^{10}$, —$NR^9C(O)OR^{10}$, —$NR^9C(O)NR^{11}R^{12}$, —$NR^9S(O)R^{10}$, —$NR^9S(O)_2R^{10}$, —$NR^9S(O)NR^{11}R^{12}$, —$NR^9S(O)_2NR^{11}R^{12}$, —$C(O)R^9$, —$C(O)OR^9$ or —$C(O)NR^9R^{10}$;

each X is independently $C_1$-$C_6$ alkyl or $C_6$-$C_{10}$ aryl-($C_1$-$C_6$ alkyl), wherein each hydrogen atom in $C_1$-$C_6$ alkyl and $C_6$-$C_{10}$ aryl-($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^9$, —$OC(O)R^9$, —$OC(O)NR^9R^{10}$, —$OS(O)R^9$, —$OS(O)_2R^9$, —$SR^9$, —$S(O)R^9$, —$S(O)_2R^9$, —$S(O)NR^9R^{10}$, —$S(O)_2NR^9R^{10}$, —$OS(O)NR^9R^{10}$, —$OS(O)_2NR^9R^{10}$, —$NR^9R^{10}$, —$NR^9C(O)R^{10}$, —$NR^9C(O)OR^{10}$, —$NR^9C(O)NR^{11}R^{12}$, —$NR^9S(O)R^{10}$, —$NR^9S(O)_2R^{10}$, —$NR^9S(O)NR^{11}R^{12}$, —$NR^9S(O)_2NR^{11}R^{12}$, —$C(O)R^9$, —$C(O)OR^9$ or —$C(O)NR^9R^{10}$;

each $R^9$, $R^{10}$, $R^{11}$ and $R^{12}$ is independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and each * represents a covalent bond to the rest of the conjugate.

6. The conjugate of claim 2, or a pharmaceutically acceptable salt thereof, comprising the formula

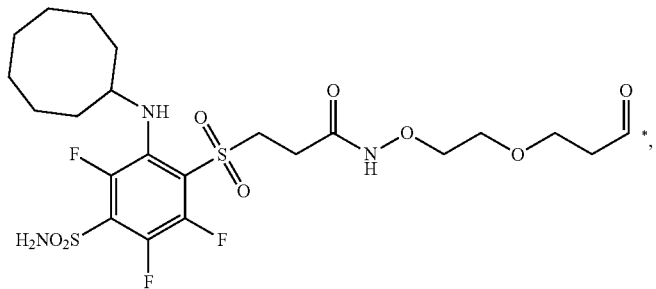

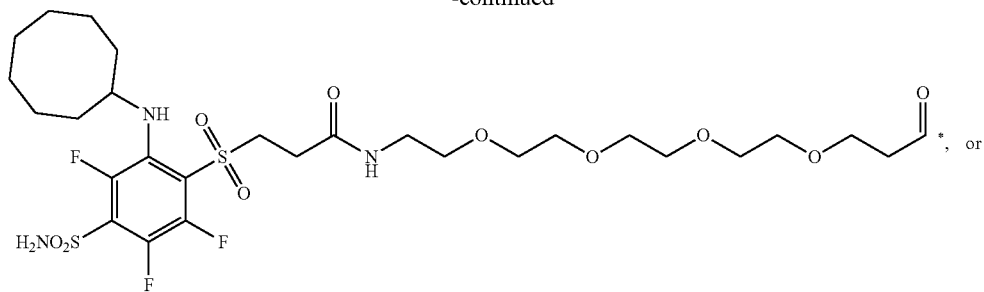

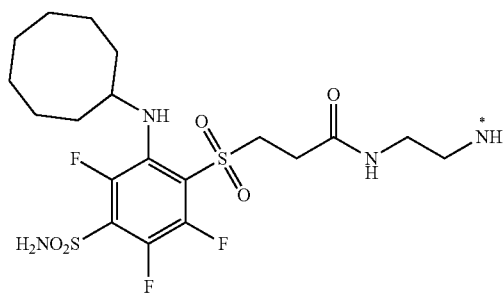

wherein * represents a point of attachment to the rest of the conjugate.

7. The conjugate of claim 1, or a pharmaceutically acceptable salt thereof, comprising a linker portion having the amino acid sequence 3-amino-alanine-Asp-Cys, or Asp-Arg-Asp-3-amino-alanine-Asp-Cys.

8. The conjugate of claim 1, or a pharmaceutically acceptable salt thereof, wherein A is a fluorescent dye.

9. The conjugate of claim 1, selected from the group consisting of

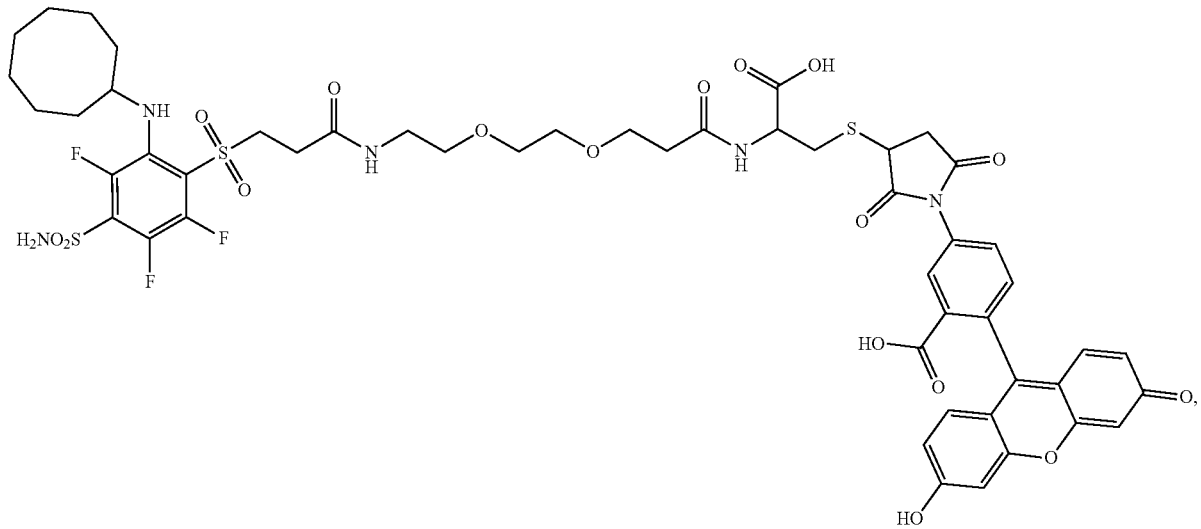

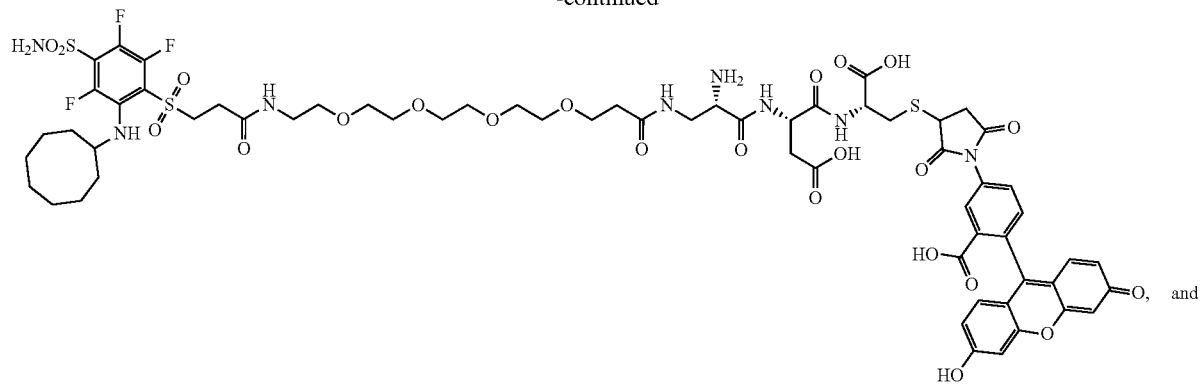

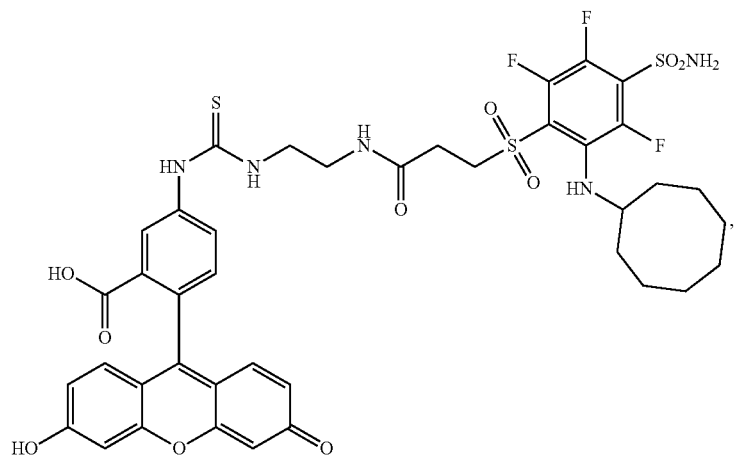

or a pharmaceutically acceptable salt thereof.

10. The conjugate of claim 1, or a pharmaceutically acceptable salt thereof, wherein A is a radio-imaging agent.

11. The conjugate of claim 1, or a pharmaceutically acceptable salt thereof, wherein A comprises radioactive isotope of a metal coordinated to a chelating group.

12. The conjugate of claim 1, or a pharmaceutically acceptable salt thereof, comprising the formula

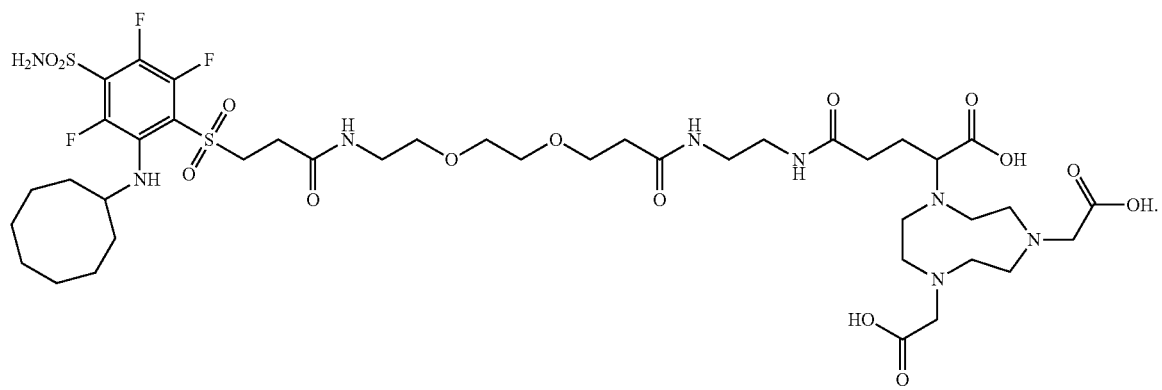 [SMILES: NS(=O)(=O)c1c(F)c(F)c(S(=O)(=O)CCC(=O)NCCOCCOCCC(=O)NCCNC(=O)CCC(C(=O)O)N2CCN(CC(=O)O)CCN(CC(=O)O)CC2)c(NC2CCCCCCC2)c1F]

13. The conjugate of claim 1, or a pharmaceutically acceptable salt thereof, wherein A is a therapeutic agent.

14. The conjugate of claim 1, or a pharmaceutically acceptable salt thereof, wherein the therapeutic agent is a tubulysin or a maytansine.

15. The conjugate of claim 1, selected from the group consisting of

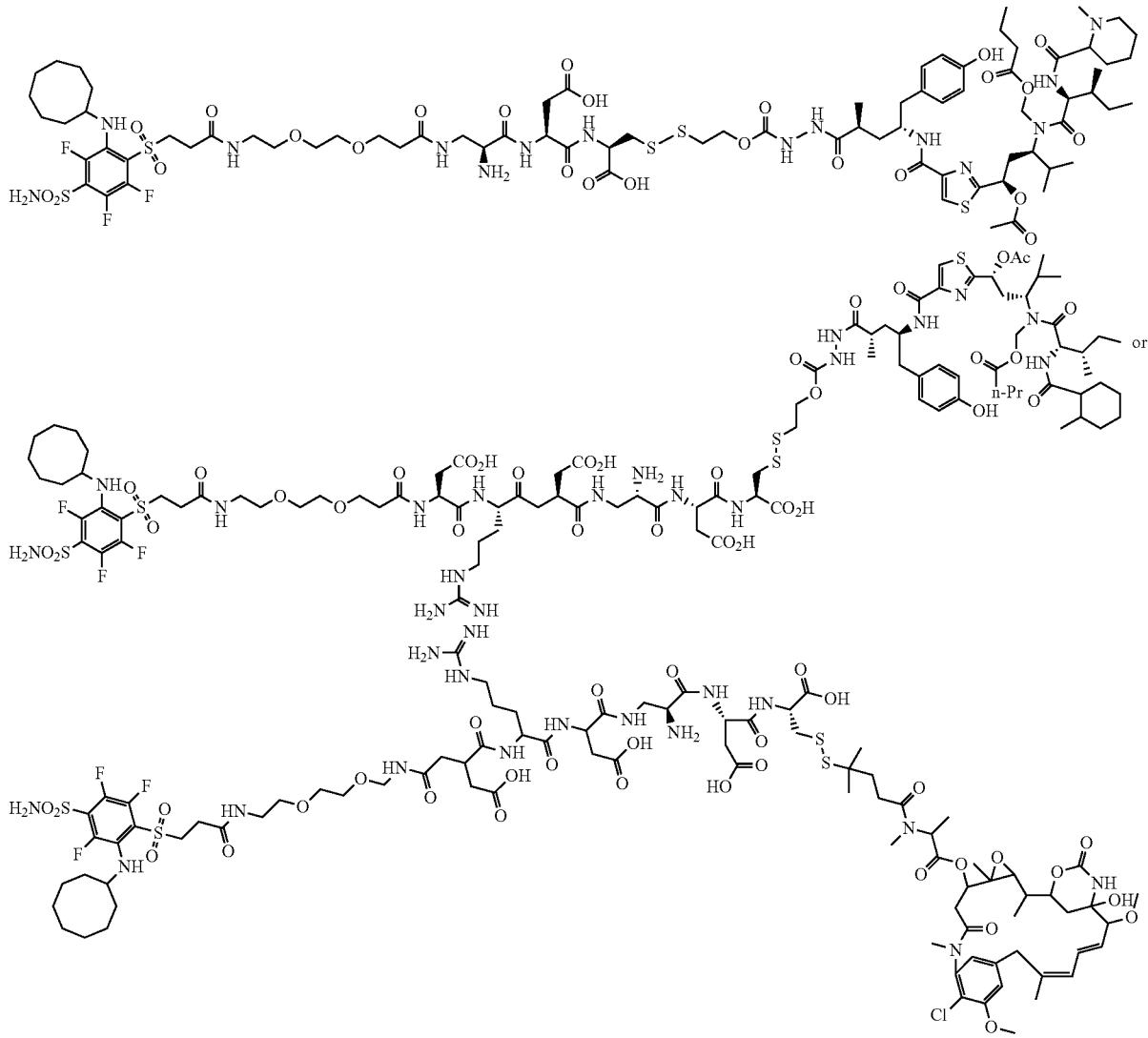

or a pharmaceutically acceptable salt thereof.

16. A method of imaging a population of cells in a subject, comprising
   a. administering to the subject an effective amount of a conjugate of the formula B-L-A, wherein B is a carbonic anhydrase IX ligand of the formula

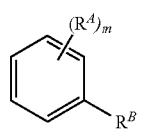

wherein
   each $R^A$ is independently selected from the group consisting of H, halogen, —$OR^1$, —$OC(O)R^1$, —$OC(O)NR^1R^2$, —$OS(O)R^1$, —$OS(O)_2R^1$, —$SR^1$, —$S(O)R^1$, —$S(O)_2R^1$, —$S(O)NR^1R^2$, —$S(O)_2NR^1R^2$, —$OS(O)NR^1R^2$, —$OS(O)_2NR^1R^2$, —$NR^1R^2$, —$NR^1C(O)R^1$, —$NR^1C(O)OR^2$, —$NR^1C(O)NR^1R^2$, —$NR^1S(O)R^2$, —$NR^1S(O)_2R^2$, —$NR^1S(O)NR^1R^2$, —$NR^1S(O)_2NR^1R^2$, —$C(O)R^1$, —$C(O)OR^1$, and —$C(O)NR^1R^2$;

$R^B$ is —$OR^3$, —$SR^3$, —$NR^3R^4$, —$S(O)_2R^3$, —$NR^4C(O)R^3$ or —$NR^4C(O)NR^3R^4$;

$R^3$ is independently $C_1$-$C_{10}$ alkyl, $C_2$-$C_{10}$ alkenyl or phenyl, each independently substituted with one substituent selected from the group consisting of —$NR^5$—*, —N(R$^5$)—C$_1$-C$_6$ alkyl-N(R$^6$)—*, —OC(O)—*, —OC(O)N(R$^5$)—*, —C(O)—*, —C(O)O—*, and —C(O)N(R$^5$)—*;

each R$^1$, R$^2$, R$^4$, R$^5$ and R$^6$ is independently selected from the group consisting of H, C$_1$-C$_6$ alkyl, C$_2$-C$_6$ alkenyl, C$_2$-C$_6$ alkynyl, and C$_3$-C$_9$ cycloalkyl;

L is an optional linker;

A is a therapeutic agent or an imaging agent;

m is an integer from 1 to 5; and

* represents a point of attachment to L or A.

17. A composition comprising a conjugate according to claim 1, or a pharmaceutically acceptable salt thereof, and optionally at least one pharmaceutically acceptable excipient.

18. A method of treating cancer in a subject comprises administering to the subject a therapeutically effective amount of a conjugate of claim 1.

19. A method of imaging a population of cells in vitro, comprising a. contacting the cells with a conjugate of claim 1, to provide labelled cells, and b. visualizing the labelled cells with a fluorescent light source or a suitable detector.

* * * * *